United States Patent
Mai et al.

(10) Patent No.: US 12,195,534 B2
(45) Date of Patent: Jan. 14, 2025

(54) BINDING MOLECULES

(71) Applicant: Immunocore Limited, Abingdon (GB)

(72) Inventors: Nicole Mai, Abingdon (GB); Arnaud Techine, Abingdon (GB); Jakub Jaworski, Abingdon (GB); Kate Atkin, Abingdon (GB); Nathaniel Liddy, Abingdon (GB); Vijaykumar Karuppiah, Abingdon (GB); Ana Pereira Ribeiro, Abingdon (GB); Ana Penas, Abingdon (GB); Andrew Creese, Abingdon (GB); Emma Grant, Abingdon (GB); Stephen Harper, Abingdon (GB); Chandramouli Chillakuri, Abingdon (GB); Eduardo Mateos-Diaz, Abingdon (GB); Tamara Aleksic, Abingdon (GB); Pedro Cuadrado Rodenas, Abingdon (GB)

(73) Assignee: IMMUNOCORE LIMITED, Abingdon (GB)

( * ) Notice: Subject to any disclaimer, the term of this patent is extended or adjusted under 35 U.S.C. 154(b) by 0 days.

(21) Appl. No.: 18/405,977

(22) Filed: Jan. 5, 2024

(65) Prior Publication Data
US 2024/0254228 A1    Aug. 1, 2024

(30) Foreign Application Priority Data

Jan. 6, 2023 (GB) ..................... 2300226
Aug. 18, 2023 (GB) ..................... 2312621

(51) Int. Cl.
| | | |
|---|---|---|
| *C07K 16/28* | (2006.01) | |
| *A61K 38/00* | (2006.01) | |
| *A61P 35/00* | (2006.01) | |
| *C07K 14/725* | (2006.01) | |

(52) U.S. Cl.
CPC .......... *C07K 16/2809* (2013.01); *A61P 35/00* (2018.01); *C07K 14/7051* (2013.01); *A61K 38/00* (2013.01); *C07K 2319/30* (2013.01)

(58) Field of Classification Search
CPC ............ C07K 16/2809; C07K 14/7051; C07K 2319/30; A61P 35/00; A61K 38/00
See application file for complete search history.

(56) References Cited

U.S. PATENT DOCUMENTS

2018/0346515 A1* 12/2018 Powlesland ...... C07K 14/70539

FOREIGN PATENT DOCUMENTS

| EP | 2155783 B1 | 2/2010 |
|---|---|---|
| WO | 1998/039482 A1 | 9/1998 |
| WO | 1999/018129 A1 | 4/1999 |
| WO | 2000/032039 A1 | 6/2000 |
| WO | 2001/062908 A2 | 8/2001 |
| WO | 2003/020763 A2 | 3/2003 |
| WO | 2004/033685 A1 | 4/2004 |
| WO | 2010/133828 A1 | 11/2010 |
| WO | 2014/096803 A1 | 6/2014 |
| WO | 2015/136072 A1 | 9/2015 |
| WO | 2017/046198 A1 | 3/2017 |
| WO | 2017/046201 A1 | 3/2017 |
| WO | 2017/089771 A1 | 6/2017 |
| WO | 2019/012138 A1 | 1/2019 |
| WO | 2019/012141 A1 | 1/2019 |
| WO | 2020/082130 A1 | 4/2020 |
| WO | 2020/157210 A1 | 8/2020 |
| WO | 2021/078774 A1 | 4/2021 |
| WO | 2022/233957 A1 | 11/2022 |
| WO | 2022/236050 A1 | 11/2022 |

OTHER PUBLICATIONS

Agirre et al., "The *CCP4* suite: integrative software for macromolecular crystallography." Acta. Crystal. Sect. D, Struct. Biol. 79, 449-461 (2023).
Aleksic et al., "Different affinity windows for virus and cancer-specific T-cell receptors: implications for therapeutic strategies," Eur J Immunol. 42(12):3174-9 (2012).
Atwell et al., "Stable heterodimers from remodeling the domain interface of a homodimer using a phage display library," J Mol Biol 270(1):26-35 (1997).
Bossi et al., "Examining the presentation of tumor-associated antigens on peptide-pulsed T2 cells," Oncoimmunol. 1;2 (11) :e26840 (2013).
Boulter et al., "Stable, soluble T-cell receptor molecules for crystallization and therapeutics," Protein Eng. 16, 707-711 (2003).
Bragado et al., "Allelic polymorphism in the coding region of human TCR Cα gene and characterization of structural variability in the a chain constant domain," International Immunology 6(2):223-30 (1994).
Cameron et al., "Identification of a Titin-derived HLA-A1-presented peptide as a cross-reactive target for engineered MAGE A3-directed T cells," Sci Transl. Med. 5 (197): 197ra103 (2013).
Dong et al., "Critical Roles of PIWIL1 in Human Tumors: Expression, Functions, Mechanisms, and Potential Clinical Implications," Front. Cell Dev. Biol., 9:1-11, doi.org/10.3389/fcell.2021.656993 (2021).
Emsley et al., "Features and development of *Coot*," Acta Crystal. Sect D Biological Crystallogr. 66, 486-501 (2010).
Epel et al., "A functional recombinant single-chain T cell receptor fragment capable of selectively targeting antigen-presenting cells," Cancer Immunol Immunother 51(10):565-73 (2002).
Gao, et al., "PIWI-like protein 1 upregulation promotes gastric cancer invasion and metastasis," Onco Targets Ther. 11: 8783-8789. doi: 10.2147/OTT.S186827 (2018).

(Continued)

*Primary Examiner* — Brad Duffy
*Assistant Examiner* — Carol Ann Chase
(74) *Attorney, Agent, or Firm* — MEDLER FERRO WOODHOUSE & MILLS PLLC

(57) ABSTRACT

The present invention relates to binding molecules that comprise T cell receptor (TCR) variable domains and which can bind to a PIWIL1 peptide-HLA complex. The invention also relates to the use of such molecules for the treatment of malignant diseases.

22 Claims, 11 Drawing Sheets
Specification includes a Sequence Listing.

(56) References Cited

OTHER PUBLICATIONS

Garboczi et al., "HLA-A2-peptide complexes: Refolding and crystallization of molecules expressed in *Escherichia coli* and complexed with single antigenic peptides," Proc. Natl. Acad. Sci. USA 89(8): 3429-3433 (1992).
Grochola et al., "The stem cell-associated Hiwi gene in human adenocarcinoma of the pancreas: expression and risk of tumour-related death," Br J Cancer 99(7): 1083-8 (2008).
He et al., "Expression of HIWI in human esophageal squamous cell carcinoma is significantly associated with poorer prognosis," BMC Cancer, 9:426 (2009).
Holler et al., "In vitro evolution of a T cell receptor with high affinity for peptide/MHC," Proc. Natl. Acad. Sci. U S A. 97(10):5387-92 (2000).
Hoo et al., "Characterization of a single-chain T-cell receptor expressed in *Escherichia coli*," Proc. Natl. Acad. Sci. U S A 89(10): 4759-4763 (1992).
Kabsch, "XDS," Acta. Crystal. Sect D Biological Crystallogr. 66, 125-132 (2010).
Kovalevskiy et al., "Overview of refinement procedures within REFMAC5: utilizing data from different sources," Acta. Crystal. Sect. D, Struct. Biol. 74, 215-227 (2018).
Li et al., "Directed evolution of human T-cell receptors with picomolar affinities by phage display," Nat Biotechnol. 23(3):349-54 (2005).
Li et al., "The universal overexpression of a cancer testis antigen hiwi is associated with cancer angiogenesis," Oncol Rep. 23(4):1063-1068 (2010).
Liddy et al., "Monoclonal TCR-redirected tumor cell killing," Nat Med. 18(6):980-7 (2012).
Mareeva et al., "How a T Cell Receptor-like Antibody Recognizes Major Histocompatibility Complex-bound Peptide," JBC 283(43):29053-29059 (2008).
McCoy et al., "*Phaser* crystallographic software," J. Appl. Crystallogr. 40, 658-674 (2007).
Merchant et al., "An efficient route to human bispecific IgG," Nat Biotechnol 16(7):677-81 (1998).
O'Callaghan et al., "BirA enzyme: production and application in the study of membrane receptor-ligand interactions by site-specific biotinylation," Anal Biochem 266(1): 9-15 (1999).
Purbhoo et al., "Quantifying and Imaging NY-ESO-1/LAGE-1-Derived Epitopes on Tumor Cells Using High Affinity T Cell Receptors," J Immunol 176(12): 7308-7316 (2006).
Ridgway et al., "'Knobs-into-holes' engineering of antibody CH3 domains for heavy chain heterodimerization," Prot Engineering 9:617 (1996).
Rudolph et al., "How TCRs bind MHCs, peptides, and coreceptors," Annu Rev Immunol. 24, 419-466 (2006).
Schodin et al., Mol Immunol 33(9): 819-829 (1996).
Shearman et al., "Construction, expression and characterization of humanized antibodies directed against the human alpha/beta T cell receptor," J Immunol. 147, 4366-73 (1991).
Taubert et al., "Expression of the stem cell self-renewal gene Hiwi and risk of tumourrelated death in patients with soft-tissue sarcoma," Oncogene. 26(7):1098-100 (2007).
Vonrhein et al., "Data processing and analysis with the *autoPROC* toolbox," Acta. Crystal. Sect D Biological Crystallogr. 67, 293-302 (2011).
Weidanz et al., "Display of functional $\alpha\beta$ single-chain T-cell receptor molecules on the surface of bacteriophage," J Immunol Methods. 221(1-2):59-76 (1998).
Willuda et al., "Tumor Targeting of Mono-, Di-, and Tetravalent Anti-p185$^{HER-2}$ Miniantibodies Multimerized by Self-associating Peptides," J. Biol. Chem. 276 (17) 14385-14392 (2001).
Wilson et al., "Specificity and degeneracy of T cells ," Mol Immunol. 40(14-15):1047-55 (2004).
Winter et al., "DIALS: Implementation and evaluation of a new integration package," Acta. Cryst. Sect D Struct Biology. 74, 85-97 (2018).
Winter, "xia2: an expert system for macromolecular crystallography data reduction," J Appl. Crystal. 43, 186-190 (2010).
Wooldridge et al., "A single autoimmune T cell receptor recognizes more than a million different peptides," J Biol Chem. 287(2):1168-77 (2012).
Zeng et al., "HIWI expression profile in cancer cells and its prognostic value for patients with colorectal cancer," Chin Med J (Engl). 124(14):2144-9 (2011).
Zhao et al., "High-affinity TCRs generated by phage display provide CD4+ T cells with the ability to recognize and kill tumor cell lines," J Immunol. 179(9):5845-54 (2007).
Zhu et al., "Identification of heavy chain residues in a humanized anti-CD3 antibody important for efficient antigen binding and T cell activation," J Immunol. 155, 1903-1910 (1995).
International Search Report in PCT/EP2024/050194, dated Mar. 20, 2024.

\* cited by examiner

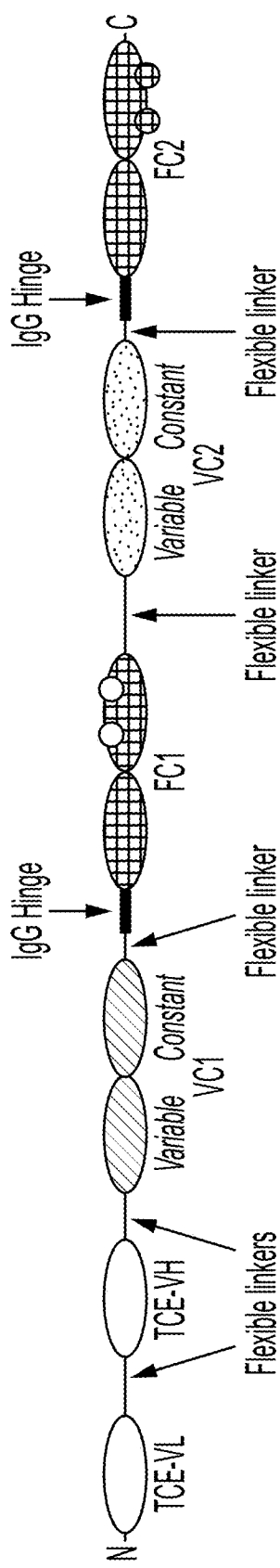
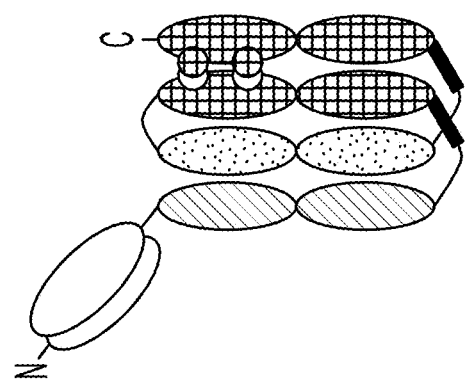
FIG. 5A
FIG. 5B

SEQUENCE LISTING

```
Sequence total quantity: 119
SEQ ID NO: 1            moltype = AA  length = 9
FEATURE                 Location/Qualifiers
REGION                  1..9
                        note = Synthetic: PIWIL1
source                  1..9
                        mol_type = protein
                        organism = synthetic construct
SEQUENCE: 1
SLSNRLYYL                                                                9

SEQ ID NO: 2            moltype = AA  length = 195
FEATURE                 Location/Qualifiers
REGION                  1..195
                        note = Synthetic: aWT of S8
source                  1..195
                        mol_type = protein
                        organism = synthetic construct
SEQUENCE: 2
LAKTTQPISM DSYEGQEVNI TCSHNNIATN DYITWYQQFP SQGPRFIIQG YKTKVTNEVA         60
SLFIPADRKS STLSLPRVSL SDTAVYYCLA WGGTDKLIFG TGTRLQVFPN IQNPDPAVYQ        120
LRDSKSSDKS VCLFTDFDSQ TNVSQSKDSD VYITDKCVLD MRSMDFKSNS AVAWSNKSDF        180
ACANAFNNSI IPEDT                                                        195

SEQ ID NO: 3            moltype = AA  length = 109
FEATURE                 Location/Qualifiers
REGION                  1..109
                        note = Synthetic: vd aWT of S8
source                  1..109
                        mol_type = protein
                        organism = synthetic construct
SEQUENCE: 3
LAKTTQPISM DSYEGQEVNI TCSHNNIATN DYITWYQQFP SQGPRFIIQG YKTKVTNEVA         60
SLFIPADRKS STLSLPRVSL SDTAVYYCLA WGGTDKLIFG TGTRLQVFP                   109

SEQ ID NO: 4            moltype = AA  length = 86
FEATURE                 Location/Qualifiers
REGION                  1..86
                        note = Synthetic: cd aWT of S8
source                  1..86
                        mol_type = protein
                        organism = synthetic construct
```

```
SEQUENCE: 4
NIQNPDPAVY QLRDSKSSDK SVCLFTDFDS QTNVSQSKDS DVYITDKCVL DMRSMDFKSN    60
SAVAWSNKSD FACANAFNNS IIPEDT                                        86

SEQ ID NO: 5              moltype = AA   length = 7
FEATURE                   Location/Qualifiers
REGION                    1..7
                          note = Synthetic: CDR1 aWT of S8
source                    1..7
                          mol_type = protein
                          organism = synthetic construct
SEQUENCE: 5
NIATNDY                                                              7

SEQ ID NO: 6              moltype = AA   length = 5
FEATURE                   Location/Qualifiers
REGION                    1..5
                          note = Synthetic: CDR2 aWT of S8
source                    1..5
                          mol_type = protein
                          organism = synthetic construct
SEQUENCE: 6
GYKTK                                                                5

SEQ ID NO: 7              moltype = AA   length = 10
FEATURE                   Location/Qualifiers
REGION                    1..10
                          note = Synthetic: CDR3 aWT of S8
source                    1..10
                          mol_type = protein
                          organism = synthetic construct
SEQUENCE: 7
LAWGGTDKLI                                                          10

SEQ ID NO: 8              moltype = AA   length = 25
FEATURE                   Location/Qualifiers
REGION                    1..25
                          note = Synthetic: FR1 aWT of S8
source                    1..25
                          mol_type = protein
                          organism = synthetic construct
SEQUENCE: 8
LAKTTQPISM DSYEGQEVNI TCSHN                                         25

SEQ ID NO: 9              moltype = AA   length = 17
FEATURE                   Location/Qualifiers
REGION                    1..17
                          note = Synthetic: FR2 aWT of S8
source                    1..17
                          mol_type = protein
                          organism = synthetic construct
SEQUENCE: 9
ITWYQQFPSQ GPRFIIQ                                                  17

SEQ ID NO: 10             moltype = AA   length = 34
FEATURE                   Location/Qualifiers
REGION                    1..34
                          note = Synthetic: FR3 aWT of S8
source                    1..34
                          mol_type = protein
                          organism = synthetic construct
SEQUENCE: 10
VTNEVASLFI PADRKSSTLS LPRVSLSDTA VYYC                               34

SEQ ID NO: 11             moltype = AA   length = 11
FEATURE                   Location/Qualifiers
REGION                    1..11
                          note = Synthetic: FR4 aWT of S8
source                    1..11
                          mol_type = protein
                          organism = synthetic construct
SEQUENCE: 11
FGTGTRLQVF P                                                        11

SEQ ID NO: 12             moltype = AA   length = 246
FEATURE                   Location/Qualifiers
REGION                    1..246
                          note = Synthetic: bWT of S8
source                    1..246
```

```
                         mol_type = protein
                         organism = synthetic construct
SEQUENCE: 12
EAGVAQSPRY KIIEKRQSVA FWCNPISGHA TLYWYQQILG QGPKLLIQFQ NNGVVDDSQL    60
PKDRFSAERL KGVDSTLKIQ PAKLEDSAVY LCASSLDWVG SGETQYFGPG TRLLVLEDLK   120
NVFPPEVAVF EPSEAEISHT QKATLVCLAT GFYPDHVELS WWVNGKEVHS GVCTDPQPLK   180
EQPALNDSRY ALSSRLRVSA TFWQDPRNHF RCQVQFYGLS ENDEWTQDRA KPVTQIVSAE   240
AWGRAD                                                              246

SEQ ID NO: 13            moltype = AA   length = 116
FEATURE                  Location/Qualifiers
REGION                   1..116
                         note = Synthetic: vd bWT of S8
source                   1..116
                         mol_type = protein
                         organism = synthetic construct
SEQUENCE: 13
EAGVAQSPRY KIIEKRQSVA FWCNPISGHA TLYWYQQILG QGPKLLIQFQ NNGVVDDSQL    60
PKDRFSAERL KGVDSTLKIQ PAKLEDSAVY LCASSLDWVG SGETQYFGPG TRLLVL       116

SEQ ID NO: 14            moltype = AA   length = 130
FEATURE                  Location/Qualifiers
REGION                   1..130
                         note = Synthetic: cd bWT of S8
source                   1..130
                         mol_type = protein
                         organism = synthetic construct
SEQUENCE: 14
EDLKNVFPPE VAVFEPSEAE ISHTQKATLV CLATGFYPDH VELSWWVNGK EVHSGVCTDP    60
QPLKEQPALN DSRYALSSRL RVSATFWQDP RNHFRCQVQF YGLSENDEWT QDRAKPVTQI   120
VSAEAWGRAD                                                          130

SEQ ID NO: 15            moltype = AA   length = 5
FEATURE                  Location/Qualifiers
REGION                   1..5
                         note = Synthetic: CDR1 bWT of S8
source                   1..5
                         mol_type = protein
                         organism = synthetic construct
SEQUENCE: 15
SGHAT                                                                5

SEQ ID NO: 16            moltype = AA   length = 6
FEATURE                  Location/Qualifiers
REGION                   1..6
                         note = Synthetic: CDR2 bWT of S8
source                   1..6
                         mol_type = protein
                         organism = synthetic construct
SEQUENCE: 16
FQNNGV                                                               6

SEQ ID NO: 17            moltype = AA   length = 14
FEATURE                  Location/Qualifiers
REGION                   1..14
                         note = Synthetic: CDR3 bWT of S8
source                   1..14
                         mol_type = protein
                         organism = synthetic construct
SEQUENCE: 17
ASSLDWVGSG ETQY                                                      14

SEQ ID NO: 18            moltype = AA   length = 26
FEATURE                  Location/Qualifiers
REGION                   1..26
                         note = Synthetic: FR1 bWT of S8
source                   1..26
                         mol_type = protein
                         organism = synthetic construct
SEQUENCE: 18
EAGVAQSPRY KIIEKRQSVA FWCNPI                                         26

SEQ ID NO: 19            moltype = AA   length = 17
FEATURE                  Location/Qualifiers
REGION                   1..17
                         note = Synthetic: FR2 bWT of S8
source                   1..17
                         mol_type = protein
                         organism = synthetic construct
```

```
SEQUENCE: 19
LYWYQQILGQ GPKLLIQ                                                       17

SEQ ID NO: 20           moltype = AA  length = 38
FEATURE                 Location/Qualifiers
REGION                  1..38
                        note = Synthetic: FR3 bWT of S8
source                  1..38
                        mol_type = protein
                        organism = synthetic construct
SEQUENCE: 20
VDDSQLPKDR FSAERLKGVD STLKIQPAKL EDSAVYLC                                 38

SEQ ID NO: 21           moltype = AA  length = 10
FEATURE                 Location/Qualifiers
REGION                  1..10
                        note = Synthetic: FR4 bWT of S8
source                  1..10
                        mol_type = protein
                        organism = synthetic construct
SEQUENCE: 21
FGPGTRLLVL                                                               10

SEQ ID NO: 22           moltype = AA  length = 109
FEATURE                 Location/Qualifiers
REGION                  1..109
                        note = Synthetic: a36
source                  1..109
                        mol_type = protein
                        organism = synthetic construct
SEQUENCE: 22
LAKTTQPISM DSYEGQEVNI TCSHNYIAAN DFITWYQQFP SQGPRFFIQG YKTNVQNEVA         60
SLFIPADRKS STLSLPRVSL SDTAVYYCLA WGGTDVLPFG TGTRLQVFP                    109

SEQ ID NO: 23           moltype = AA  length = 7
FEATURE                 Location/Qualifiers
REGION                  1..7
                        note = Synthetic: CDR1
source                  1..7
                        mol_type = protein
                        organism = synthetic construct
SEQUENCE: 23
YIAANDF                                                                  7

SEQ ID NO: 24           moltype = AA  length = 5
FEATURE                 Location/Qualifiers
REGION                  1..5
                        note = Synthetic: CDR2
source                  1..5
                        mol_type = protein
                        organism = synthetic construct
SEQUENCE: 24
GYKTN                                                                    5

SEQ ID NO: 25           moltype = AA  length = 10
FEATURE                 Location/Qualifiers
REGION                  1..10
                        note = Synthetic: CDR3
source                  1..10
                        mol_type = protein
                        organism = synthetic construct
SEQUENCE: 25
LAWGGTDVLP                                                               10

SEQ ID NO: 26           moltype = AA  length = 17
FEATURE                 Location/Qualifiers
REGION                  1..17
                        note = Synthetic: FR2
source                  1..17
                        mol_type = protein
                        organism = synthetic construct
SEQUENCE: 26
ITWYQQFPSQ GPRFFIQ                                                       17

SEQ ID NO: 27           moltype = AA  length = 34
FEATURE                 Location/Qualifiers
REGION                  1..34
                        note = Synthetic: FR3
source                  1..34
```

```
                            mol_type = protein
                            organism = synthetic construct
SEQUENCE: 27
VQNEVASLFI PADRKSSTLS LPRVSLSDTA VYYC                                          34

SEQ ID NO: 28               moltype = AA    length = 109
FEATURE                     Location/Qualifiers
REGION                      1..109
                            note = Synthetic: a40
source                      1..109
                            mol_type = protein
                            organism = synthetic construct
SEQUENCE: 28
LAKTTQPISM DSYEGQEVNI TCSHNYIAAN DFITWYQQFP SQGPRFFIQG YKTNVQNEVA              60
SLFIPADRKS STLSLPRVSL SDTAVYYCLA WGGTDLLPFG TGTRLQVFP                          109

SEQ ID NO: 29               moltype = AA    length = 10
FEATURE                     Location/Qualifiers
REGION                      1..10
                            note = Synthetic: CDR3
source                      1..10
                            mol_type = protein
                            organism = synthetic construct
SEQUENCE: 29
LAWGGTDLLP                                                                     10

SEQ ID NO: 30               moltype = AA    length = 109
FEATURE                     Location/Qualifiers
REGION                      1..109
                            note = Synthetic: a58
source                      1..109
                            mol_type = protein
                            organism = synthetic construct
SEQUENCE: 30
AAKTTQPISM DSYEGQEVNI TCSHNYIAAN DFITWYQQFP SQGPRFFIQG YKTNVQNEVA              60
SLFIPADRKS STLSLPRVSL SDTAVYYCLA WGGTDLLPFG TGTRLQVFP                          109

SEQ ID NO: 31               moltype = AA    length = 25
FEATURE                     Location/Qualifiers
REGION                      1..25
                            note = Synthetic: FR1
source                      1..25
                            mol_type = protein
                            organism = synthetic construct
SEQUENCE: 31
AAKTTQPISM DSYEGQEVNI TCSHN                                                    25

SEQ ID NO: 32               moltype = AA    length = 109
FEATURE                     Location/Qualifiers
REGION                      1..109
                            note = Synthetic: a61
source                      1..109
                            mol_type = protein
                            organism = synthetic construct
SEQUENCE: 32
LAKTTQPISM DSYEGQEVNI PCSHNYIAAN DFITWYQQFP SQGPRFFIQG YKTNVQNEVA              60
SLFISADRKS STLSLPRVSL SDTAVYYCLA WGGTDLLPFG TGTRLQVFP                          109

SEQ ID NO: 33               moltype = AA    length = 25
FEATURE                     Location/Qualifiers
REGION                      1..25
                            note = Synthetic: FR1
source                      1..25
                            mol_type = protein
                            organism = synthetic construct
SEQUENCE: 33
LAKTTQPISM DSYEGQEVNI PCSHN                                                    25

SEQ ID NO: 34               moltype = AA    length = 109
FEATURE                     Location/Qualifiers
REGION                      1..109
                            note = Synthetic: a67
source                      1..109
                            mol_type = protein
                            organism = synthetic construct
SEQUENCE: 34
AAKTTQPISM DSYEGQEVNI PCSHNYIAAN DFITWYQQFP SQGPRFFIQG YKTNVQNEVA              60
SLFISADRKS STLSLPRVSL SDTAVYYCLA WGGTDLLPFG TGTRLQVFP                          109
```

```
SEQ ID NO: 35            moltype = AA  length = 25
FEATURE                  Location/Qualifiers
REGION                   1..25
                         note = Synthetic: FR1
source                   1..25
                         mol_type = protein
                         organism = synthetic construct
SEQUENCE: 35
AAKTTQPISM DSYEGQEVNI PCSHN                                         25

SEQ ID NO: 36            moltype = AA  length = 116
FEATURE                  Location/Qualifiers
REGION                   1..116
                         note = Synthetic: b23
source                   1..116
                         mol_type = protein
                         organism = synthetic construct
SEQUENCE: 36
EAGVAQSPRY KIIEKRQSVA FWCNPISGHG TLYWYQQILG QGPKLLIQFH ENGVVDDSQL   60
PKDRFSAERL KGVDSTLKIQ PAKLEDSAVY LCASSVDWVG DGERQYFGPG TRLLVL      116

SEQ ID NO: 37            moltype = AA  length = 5
FEATURE                  Location/Qualifiers
REGION                   1..5
                         note = Synthetic: CDR1
source                   1..5
                         mol_type = protein
                         organism = synthetic construct
SEQUENCE: 37
SGHGT                                                                5

SEQ ID NO: 38            moltype = AA  length = 6
FEATURE                  Location/Qualifiers
REGION                   1..6
                         note = Synthetic: CDR2
source                   1..6
                         mol_type = protein
                         organism = synthetic construct
SEQUENCE: 38
FHENGV                                                               6

SEQ ID NO: 39            moltype = AA  length = 14
FEATURE                  Location/Qualifiers
REGION                   1..14
                         note = Synthetic: CDR3
source                   1..14
                         mol_type = protein
                         organism = synthetic construct
SEQUENCE: 39
ASSWDWVGDG ERQY                                                     14

SEQ ID NO: 40            moltype = AA  length = 116
FEATURE                  Location/Qualifiers
REGION                   1..116
                         note = Synthetic: b37
source                   1..116
                         mol_type = protein
                         organism = synthetic construct
SEQUENCE: 40
EAGVAQSPRY KIIEKRQSVA FWCNPISGHG TLYWYQQILG QGPKLLIQFH ENGVVDDSQL   60
PKDRFSAERL KGVDSTLKIQ PAKLEDSAVY LCASSWDWVG DGERQYFGPG TRLLVL      116

SEQ ID NO: 41            moltype = AA  length = 14
FEATURE                  Location/Qualifiers
REGION                   1..14
                         note = Synthetic: CDR3
source                   1..14
                         mol_type = protein
                         organism = synthetic construct
SEQUENCE: 41
ASSVDWVGDG ERQY                                                     14

SEQ ID NO: 42            moltype = AA  length = 116
FEATURE                  Location/Qualifiers
REGION                   1..116
                         note = Synthetic: b38
source                   1..116
                         mol_type = protein
                         organism = synthetic construct
```

```
SEQUENCE: 42
EAGVAQSPRY KIIEKRQSVA FWCNPITGHG TLYWYQQILG QGPKLLIQFH ENGVVDDSQL   60
PKDRFSAERL KGVDSTLKIQ PAKLEDSAVY LCASSVDWVG DGERQYFGPG TRLLVL      116

SEQ ID NO: 43           moltype = AA  length = 5
FEATURE                 Location/Qualifiers
REGION                  1..5
                        note = Synthetic: CDR1
source                  1..5
                        mol_type = protein
                        organism = synthetic construct
SEQUENCE: 43
TGHGT                                                              5

SEQ ID NO: 44           moltype = AA  length = 116
FEATURE                 Location/Qualifiers
REGION                  1..116
                        note = Synthetic: b63
source                  1..116
                        mol_type = protein
                        organism = synthetic construct
SEQUENCE: 44
EAGVAQSPRY KIIEKRQSVA FWCNPISGHG TLYWYQQILG QGPKLLIQFH EEGVVDDSQL   60
PKDRFSAERL KGVDSTLKIQ PAKLEDSAVY LCASSVDWVG DGERQYFGPG TRLLVL      116

SEQ ID NO: 45           moltype = AA  length = 6
FEATURE                 Location/Qualifiers
REGION                  1..6
                        note = Synthetic: CDR2
source                  1..6
                        mol_type = protein
                        organism = synthetic construct
SEQUENCE: 45
FHEEGV                                                             6

SEQ ID NO: 46           moltype = AA  length = 116
FEATURE                 Location/Qualifiers
REGION                  1..116
                        note = Synthetic: b68
source                  1..116
                        mol_type = protein
                        organism = synthetic construct
SEQUENCE: 46
EAGVAQSPRY KIIEKGQSVA FWCNPISGHG TLYWYQQILG QGPKLLIQFH ENGVVDDSQL   60
PKDRFSAERL KGVDSTLKIQ PAKLEDSAVY LCASSVDWVG DGERQYFGPG TRLLVL      116

SEQ ID NO: 47           moltype = AA  length = 26
FEATURE                 Location/Qualifiers
REGION                  1..26
                        note = Synthetic: FR1
source                  1..26
                        mol_type = protein
                        organism = synthetic construct
SEQUENCE: 47
EAGVAQSPRY KIIEKGQSVA FWCNPI                                       26

SEQ ID NO: 48           moltype = AA  length = 116
FEATURE                 Location/Qualifiers
REGION                  1..116
                        note = Synthetic: b72
source                  1..116
                        mol_type = protein
                        organism = synthetic construct
SEQUENCE: 48
EAGVAQSPRY KIIEKGQSVA FWCNPISGHG TLYWYQQILG QGPKLLIQFH EEGVVDDSQL   60
PKDRFSAERL KGVDSTLKIQ PAKLEDSAVY LCASSVDWVG DGERQYFGPG TRLLVL      116

SEQ ID NO: 49           moltype = AA  length = 195
FEATURE                 Location/Qualifiers
REGION                  1..195
                        note = Synthetic: a40
source                  1..195
                        mol_type = protein
                        organism = synthetic construct
SEQUENCE: 49
LAKTTQPISM DSYEGQEVNI TCSHNYIAAN DFITWYQQFP SQGPRFFIQG YKTNVQNEVA   60
SLFIPADRKS STLSLPRVSL SDTAVYYCLA WGGTDLLPFG TGTRLQVFPN IQNPDPAVYQ   120
LRDSKSSDKS VCLFTDFDSQ TNVSQSKDSD VYITDKCVLD MRSMDFKSNS AVAWSNKSDF   180
ACANAFNNSI IPEDT                                                   195
```

```
SEQ ID NO: 50           moltype = AA  length = 246
FEATURE                 Location/Qualifiers
REGION                  1..246
                        note = Synthetic: b23
source                  1..246
                        mol_type = protein
                        organism = synthetic construct
SEQUENCE: 50
EAGVAQSPRY KIIEKRQSVA FWCNPISGHG TLYWYQQILG QGPKLLIQFH ENGVVDDSQL    60
PKDRFSAERL KGVDSTLKIQ PAKLEDSAVY LCASSVDWVG DGERQYFGPG TRLLVLEDLK   120
NVFPPEVAVF EPSEAEISHT QKATLVCLAT GFYPDHVELS WWVNGKEVHS GVCTDPQPLK   180
EQPALNDSRY ALSSRLRVSA TFWQDPRNHF RCQVQFYGLS ENDEWTQDRA KPVTQIVSAE   240
AWGRAD                                                              246

SEQ ID NO: 51           moltype = AA  length = 195
FEATURE                 Location/Qualifiers
REGION                  1..195
                        note = Synthetic: a36
source                  1..195
                        mol_type = protein
                        organism = synthetic construct
SEQUENCE: 51
LAKTTQPISM DSYEGQEVNI TCSHNYIAAN DFITWYQQFP SQGPRFFIQG YKTNVQNEVA    60
SLFIPADRKS STLSLPRVSL SDTAVYYCLA WGGTDVLPFG TGTRLQVPPN IQNPDPAVYQ   120
LRDSKSSDKS VCLFTDFDSQ TNVSQSKDSD VYITDKCVLD MRSMDFKSNS AVAWSNKSDF   180
ACANAFNNSI IPEDT                                                    195

SEQ ID NO: 52           moltype = AA  length = 246
FEATURE                 Location/Qualifiers
REGION                  1..246
                        note = Synthetic: b38
source                  1..246
                        mol_type = protein
                        organism = synthetic construct
SEQUENCE: 52
EAGVAQSPRY KIIEKRQSVA FWCNPITGHG TLYWYQQILG QGPKLLIQFH ENGVVDDSQL    60
PKDRFSAERL KGVDSTLKIQ PAKLEDSAVY LCASSVDWVG DGERQYFGPG TRLLVLEDLK   120
NVFPPEVAVF EPSEAEISHT QKATLVCLAT GFYPDHVELS WWVNGKEVHS GVCTDPQPLK   180
EQPALNDSRY ALSSRLRVSA TFWQDPRNHF RCQVQFYGLS ENDEWTQDRA KPVTQIVSAE   240
AWGRAD                                                              246

SEQ ID NO: 53           moltype = AA  length = 246
FEATURE                 Location/Qualifiers
REGION                  1..246
                        note = Synthetic: b37
source                  1..246
                        mol_type = protein
                        organism = synthetic construct
SEQUENCE: 53
EAGVAQSPRY KIIEKRQSVA FWCNPISGHG TLYWYQQILG QGPKLLIQFH ENGVVDDSQL    60
PKDRFSAERL KGVDSTLKIQ PAKLEDSAVY LCASSWDWVG DGERQYFGPG TRLLVLEDLK   120
NVFPPEVAVF EPSEAEISHT QKATLVCLAT GFYPDHVELS WWVNGKEVHS GVCTDPQPLK   180
EQPALNDSRY ALSSRLRVSA TFWQDPRNHF RCQVQFYGLS ENDEWTQDRA KPVTQIVSAE   240
AWGRAD                                                              246

SEQ ID NO: 54           moltype = AA  length = 195
FEATURE                 Location/Qualifiers
REGION                  1..195
                        note = Synthetic: a58
source                  1..195
                        mol_type = protein
                        organism = synthetic construct
SEQUENCE: 54
AAKTTQPISM DSYEGQEVNI TCSHNYIAAN DFITWYQQFP SQGPRFFIQG YKTNVQNEVA    60
SLFIPADRKS STLSLPRVSL SDTAVYYCLA WGGTDLLPFG TGTRLQVPPN IQNPDPAVYQ   120
LRDSKSSDKS VCLFTDFDSQ TNVSQSKDSD VYITDKCVLD MRSMDFKSNS AVAWSNKSDF   180
ACANAFNNSI IPEDT                                                    195

SEQ ID NO: 55           moltype = AA  length = 246
FEATURE                 Location/Qualifiers
REGION                  1..246
                        note = Synthetic: b63
source                  1..246
                        mol_type = protein
                        organism = synthetic construct
SEQUENCE: 55
EAGVAQSPRY KIIEKRQSVA FWCNPISGHG TLYWYQQILG QGPKLLIQFH EEGVVDDSQL    60
PKDRFSAERL KGVDSTLKIQ PAKLEDSAVY LCASSVDWVG DGERQYFGPG TRLLVLEDLK   120
```

```
NVFPPEVAVF EPSEAEISHT QKATLVCLAT GFYPDHVELS WWVNGKEVHS GVCTDPQPLK   180
EQPALNDSRY ALSSRLRVSA TFWQDPRNHF RCQVQFYGLS ENDEWTQDRA KPVTQIVSAE   240
AWGRAD                                                             246

SEQ ID NO: 56            moltype = AA  length = 195
FEATURE                  Location/Qualifiers
REGION                   1..195
                         note = Synthetic: a61
source                   1..195
                         mol_type = protein
                         organism = synthetic construct
SEQUENCE: 56
LAKTTQPISM DSYEGQEVNI PCSHNYIAAN DFITWYQQFP SQGPRFFIQG YKTNVQNEVA   60
SLFISADRKS STLSLPRVSL SDTAVYYCLA WGGTDLLPFG TGTRLQVFPN IQNPDPAVYQ   120
LRDSKSSDKS VCLFTDFDSQ TNVSQSKDSD VYITDKCVLD MRSMDFKSNS AVAWSNKSDF   180
ACANAFNNSI IPEDT                                                   195

SEQ ID NO: 57            moltype = AA  length = 246
FEATURE                  Location/Qualifiers
REGION                   1..246
                         note = Synthetic: b68
source                   1..246
                         mol_type = protein
                         organism = synthetic construct
SEQUENCE: 57
EAGVAQSPRY KIIEKGQSVA FWCNPISGHG TLYWYQQILG QGPKLLIQFH ENGVVDDSQL   60
PKDRFSAERL KGVDSTLKIQ PAKLEDSAVY LCASSVDWVG DGERQYFGPG TRLLVLEDLK   120
NVFPPEVAVF EPSEAEISHT QKATLVCLAT GFYPDHVELS WWVNGKEVHS GVCTDPQPLK   180
EQPALNDSRY ALSSRLRVSA TFWQDPRNHF RCQVQFYGLS ENDEWTQDRA KPVTQIVSAE   240
AWGRAD                                                             246

SEQ ID NO: 58            moltype = AA  length = 195
FEATURE                  Location/Qualifiers
REGION                   1..195
                         note = Synthetic: a67
source                   1..195
                         mol_type = protein
                         organism = synthetic construct
SEQUENCE: 58
AAKTTQPISM DSYEGQEVNI PCSHNYIAAN DFITWYQQFP SQGPRFFIQG YKTNVQNEVA   60
SLFISADRKS STLSLPRVSL SDTAVYYCLA WGGTDLLPFG TGTRLQVFPN IQNPDPAVYQ   120
LRDSKSSDKS VCLFTDFDSQ TNVSQSKDSD VYITDKCVLD MRSMDFKSNS AVAWSNKSDF   180
ACANAFNNSI IPEDT                                                   195

SEQ ID NO: 59            moltype = AA  length = 246
FEATURE                  Location/Qualifiers
REGION                   1..246
                         note = Synthetic: b72
source                   1..246
                         mol_type = protein
                         organism = synthetic construct
SEQUENCE: 59
EAGVAQSPRY KIIEKGQSVA FWCNPISGHG TLYWYQQILG QGPKLLIQFH EEGVVDDSQL   60
PKDRFSAERL KGVDSTLKIQ PAKLEDSAVY LCASSVDWVG DGERQYFGPG TRLLVLEDLK   120
NVFPPEVAVF EPSEAEISHT QKATLVCLAT GFYPDHVELS WWVNGKEVHS GVCTDPQPLK   180
EQPALNDSRY ALSSRLRVSA TFWQDPRNHF RCQVQFYGLS ENDEWTQDRA KPVTQIVSAE   240
AWGRAD                                                             246

SEQ ID NO: 60            moltype = AA  length = 253
FEATURE                  Location/Qualifiers
REGION                   1..253
                         note = Synthetic: anti-CD3 scFv: U0
source                   1..253
                         mol_type = protein
                         organism = synthetic construct
SEQUENCE: 60
AIQMTQSPSS LSASVGDRVT ITCRASQDIR NYLNWYQQKP GKAPKLLIYY TSRLESGVPS   60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYTMNWVRQ APGKGLEWVA   180
LINPYKGVST YNQKFKDRFT ISVDKSKNTA YLQMNSLRAE DTAVYYCARS GYYGDSDWYF   240
DVWGQGTLVT VSS                                                     253

SEQ ID NO: 61            moltype = AA  length = 107
FEATURE                  Location/Qualifiers
REGION                   1..107
                         note = Synthetic: VL
source                   1..107
                         mol_type = protein
                         organism = synthetic construct
```

```
SEQUENCE: 61
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIK                 107

SEQ ID NO: 62            moltype = AA   length = 6
FEATURE                  Location/Qualifiers
REGION                   1..6
                         note = Synthetic: VL CDR1
source                   1..6
                         mol_type = protein
                         organism = synthetic construct
SEQUENCE: 62
QDIRNY                                                                6

SEQ ID NO: 63            moltype =      length =
SEQUENCE: 63
000

SEQ ID NO: 64            moltype = AA   length = 9
FEATURE                  Location/Qualifiers
REGION                   1..9
                         note = Synthetic: VL CDR3
source                   1..9
                         mol_type = protein
                         organism = synthetic construct
SEQUENCE: 64
QQGNTLPWT                                                             9

SEQ ID NO: 65            moltype = AA   length = 122
FEATURE                  Location/Qualifiers
REGION                   1..122
                         note = Synthetic: VH
source                   1..122
                         mol_type = protein
                         organism = synthetic construct
SEQUENCE: 65
EVQLVESGGG LVQPGGSLRL SCAASGYSFT GYTMNWVRQA PGKGLEWVAL INPYKGVSTY    60
NQKFKDRFTI SVDKSKNTAY LQMNSLRAED TAVYYCARSG YYGDSDWYFD VWGQGTLVTV   120
SS                                                                  122

SEQ ID NO: 66            moltype = AA   length = 8
FEATURE                  Location/Qualifiers
REGION                   1..8
                         note = Synthetic: VH CDR1 (1/2)
source                   1..8
                         mol_type = protein
                         organism = synthetic construct
SEQUENCE: 66
GYSFTGYT                                                              8

SEQ ID NO: 67            moltype = AA   length = 8
FEATURE                  Location/Qualifiers
REGION                   1..8
                         note = Synthetic: VH CDR2
source                   1..8
                         mol_type = protein
                         organism = synthetic construct
SEQUENCE: 67
INPYKGVS                                                              8

SEQ ID NO: 68            moltype = AA   length = 15
FEATURE                  Location/Qualifiers
REGION                   1..15
                         note = Synthetic: VH CDR3
source                   1..15
                         mol_type = protein
                         organism = synthetic construct
SEQUENCE: 68
ARSGYYGDSD WYFDV                                                     15

SEQ ID NO: 69            moltype = AA   length = 122
FEATURE                  Location/Qualifiers
REGION                   1..122
                         note = Synthetic: VH
source                   1..122
                         mol_type = protein
                         organism = synthetic construct
SEQUENCE: 69
EVQLVESGGG LVQPGGSLRL SCAASGYSFT GYAMNWVRQA PGKGLEWVAL INPYKGVSTY    60
```

```
NQKFKDRFTF SVDKSKNTAY LQMNSLRAED TAVYYCARSG YYGDSDWYFD VWGQGTLVTV  120
SS                                                                122

SEQ ID NO: 70            moltype = AA  length = 253
FEATURE                  Location/Qualifiers
REGION                   1..253
                         note = Synthetic: anti-CD3 scFv: U28
source                   1..253
                         mol_type = protein
                         organism = synthetic construct
SEQUENCE: 70
AIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIKGGG GSGGGGSGGG 120
GSGGGGSGGG SEVQLVESGG GLVQPGGSLR LSCAASGYSF TGYAMNWVRQ APGKGLEWVA 180
LINPYKGVST YNQKFKDRFT FSVDKSKNTA YLQMNSLRAE DTAVYYCARS GYYGDSDWYF 240
DVWGQGTLVT VSS                                                   253

SEQ ID NO: 71            moltype = AA  length = 8
FEATURE                  Location/Qualifiers
REGION                   1..8
                         note = Synthetic: VH (CDR1 2/2)
source                   1..8
                         mol_type = protein
                         organism = synthetic construct
SEQUENCE: 71
GYSFTGYA                                                            8

SEQ ID NO: 72            moltype = AA  length = 5
FEATURE                  Location/Qualifiers
REGION                   1..5
                         note = Synthetic: Linker
source                   1..5
                         mol_type = protein
                         organism = synthetic construct
SEQUENCE: 72
GGGGS                                                               5

SEQ ID NO: 73            moltype = AA  length = 504
FEATURE                  Location/Qualifiers
REGION                   1..504
                         note = Synthetic: b38U28
source                   1..504
                         mol_type = protein
                         organism = synthetic construct
SEQUENCE: 73
AIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIKGGG GSGGGGSGGG 120
GSGGGGSGGG SEVQLVESGG GLVQPGGSLR LSCAASGYSF TGYAMNWVRQ APGKGLEWVA 180
LINPYKGVST YNQKFKDRFT FSVDKSKNTA YLQMNSLRAE DTAVYYCARS GYYGDSDWYF 240
DVWGQGTLVT VSSGGGGSEA GVAQSPRYKI IEKRQSVAFW CNPITGHGTL YWYQQILGQG 300
PKLLIQFHEN GVVDDSQLPK DRFSAERLKG VDSTLKIQPA KLEDSAVYLC ASSVDWVGDG 360
ERQYFGPGTR LLVLEDLKNV FPPEVAVFEP SEAEISHTQK ATLVCLATGF YPDHVELSWW 420
VNGKEVHSGV CTDPQPLKEQ PALNDSRYAL SSRLRVSATF WQDPRNHFRC QVQFYGLSEN 480
DEWTQDRAKP VTQIVSAEAW GRAD                                       504

SEQ ID NO: 74            moltype = AA  length = 504
FEATURE                  Location/Qualifiers
REGION                   1..504
                         note = Synthetic: b37U28
source                   1..504
                         mol_type = protein
                         organism = synthetic construct
SEQUENCE: 74
AIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIKGGG GSGGGGSGGG 120
GSGGGGSGGG SEVQLVESGG GLVQPGGSLR LSCAASGYSF TGYAMNWVRQ APGKGLEWVA 180
LINPYKGVST YNQKFKDRFT FSVDKSKNTA YLQMNSLRAE DTAVYYCARS GYYGDSDWYF 240
DVWGQGTLVT VSSGGGGSEA GVAQSPRYKI IEKRQSVAFW CNPISGHGTL YWYQQILGQG 300
PKLLIQFHEN GVVDDSQLPK DRFSAERLKG VDSTLKIQPA KLEDSAVYLC ASSWDWVGDG 360
ERQYFGPGTR LLVLEDLKNV FPPEVAVFEP SEAEISHTQK ATLVCLATGF YPDHVELSWW 420
VNGKEVHSGV CTDPQPLKEQ PALNDSRYAL SSRLRVSATF WQDPRNHFRC QVQFYGLSEN 480
DEWTQDRAKP VTQIVSAEAW GRAD                                       504

SEQ ID NO: 75            moltype = AA  length = 504
FEATURE                  Location/Qualifiers
REGION                   1..504
                         note = Synthetic: b63U28
source                   1..504
                         mol_type = protein
```

```
                        organism = synthetic construct
SEQUENCE: 75
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSSGGGGSEA GVAQSPRYKI IEKRQSVAFW CNPISGHGTL YWYQQILGQG   300
PKLLIQFHEN GVVDDSQLPK DRFSAERLKG VDSTLKIQPA KLEDSAVYLC ASSWDWVGDG   360
ERQYFGPGTR LLVLEDLKNV FPPEVAVFEP SEAEISHTQK ATLVCLATGF YPDHVELSWW   420
VNGKEVHSGV CTDPQPLKEQ PALNDSRYAL SSRLRVSATF WQDPRNHFRC QVQFYGLSEN   480
DEWTQDRAKP VTQIVSAEAW GRAD                                         504

SEQ ID NO: 76           moltype = AA   length = 504
FEATURE                 Location/Qualifiers
REGION                  1..504
                        note = Synthetic: b68U28
source                  1..504
                        mol_type = protein
                        organism = synthetic construct
SEQUENCE: 76
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSSGGGGSEA GVAQSPRYKI IEKGQSVAFW CNPISGHGTL YWYQQILGQG   300
PKLLIQFHEN GVVDDSQLPK DRFSAERLKG VDSTLKIQPA KLEDSAVYLC ASSVDWVGDG   360
ERQYFGPGTR LLVLEDLKNV FPPEVAVFEP SEAEISHTQK ATLVCLATGF YPDHVELSWW   420
VNGKEVHSGV CTDPQPLKEQ PALNDSRYAL SSRLRVSATF WQDPRNHFRC QVQFYGLSEN   480
DEWTQDRAKP VTQIVSAEAW GRAD                                         504

SEQ ID NO: 77           moltype = AA   length = 504
FEATURE                 Location/Qualifiers
REGION                  1..504
                        note = Synthetic: b72U28
source                  1..504
                        mol_type = protein
                        organism = synthetic construct
SEQUENCE: 77
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSSGGGGSEA GVAQSPRYKI IEKGQSVAFW CNPISGHGTL YWYQQILGQG   300
PKLLIQFHEE GVVDDSQLPK DRFSAERLKG VDSTLKIQPA KLEDSAVYLC ASSVDWVGDG   360
ERQYFGPGTR LLVLEDLKNV FPPEVAVFEP SEAEISHTQK ATLVCLATGF YPDHVELSWW   420
VNGKEVHSGV CTDPQPLKEQ PALNDSRYAL SSRLRVSATF WQDPRNHFRC QVQFYGLSEN   480
DEWTQDRAKP VTQIVSAEAW GRAD                                         504

SEQ ID NO: 78           moltype = AA   length = 5
FEATURE                 Location/Qualifiers
REGION                  1..5
                        note = Synthetic: Linker
source                  1..5
                        mol_type = protein
                        organism = synthetic construct
SEQUENCE: 78
GGGSG                                                                5

SEQ ID NO: 79           moltype = AA   length = 5
FEATURE                 Location/Qualifiers
REGION                  1..5
                        note = Synthetic: Linker
source                  1..5
                        mol_type = protein
                        organism = synthetic construct
SEQUENCE: 79
GGSGG                                                                5

SEQ ID NO: 80           moltype = AA   length = 5
FEATURE                 Location/Qualifiers
REGION                  1..5
                        note = Synthetic: Linker
source                  1..5
                        mol_type = protein
                        organism = synthetic construct
SEQUENCE: 80
GSGGG                                                                5

SEQ ID NO: 81           moltype = AA   length = 6
```

```
FEATURE                 Location/Qualifiers
REGION                  1..6
                        note = Synthetic: Linker
source                  1..6
                        mol_type = protein
                        organism = synthetic construct
SEQUENCE: 81
GSGGGP                                                                    6

SEQ ID NO: 82           moltype = AA  length = 5
FEATURE                 Location/Qualifiers
REGION                  1..5
                        note = Synthetic: Linker
source                  1..5
                        mol_type = protein
                        organism = synthetic construct
SEQUENCE: 82
GGEPS                                                                     5

SEQ ID NO: 83           moltype = AA  length = 7
FEATURE                 Location/Qualifiers
REGION                  1..7
                        note = Synthetic: Linker
source                  1..7
                        mol_type = protein
                        organism = synthetic construct
SEQUENCE: 83
GGEGGGP                                                                   7

SEQ ID NO: 84           moltype = AA  length = 12
FEATURE                 Location/Qualifiers
REGION                  1..12
                        note = Synthetic: Linker
source                  1..12
                        mol_type = protein
                        organism = synthetic construct
SEQUENCE: 84
GGEGGGSEGG GS                                                            12

SEQ ID NO: 85           moltype = AA  length = 8
FEATURE                 Location/Qualifiers
REGION                  1..8
                        note = Synthetic: Linker
source                  1..8
                        mol_type = protein
                        organism = synthetic construct
SEQUENCE: 85
GGGSGGGG                                                                  8

SEQ ID NO: 86           moltype = AA  length = 24
FEATURE                 Location/Qualifiers
REGION                  1..24
                        note = Synthetic: Linker
source                  1..24
                        mol_type = protein
                        organism = synthetic construct
SEQUENCE: 86
GGGGSGGGGS GGGGSGGGGS GGGS                                               24

SEQ ID NO: 87           moltype = AA  length = 20
FEATURE                 Location/Qualifiers
REGION                  1..20
                        note = Synthetic: Linker
source                  1..20
                        mol_type = protein
                        organism = synthetic construct
SEQUENCE: 87
GGGGSGGGGS GGGGSGGGGS                                                    20

SEQ ID NO: 88           moltype = AA  length = 5
FEATURE                 Location/Qualifiers
REGION                  1..5
                        note = Synthetic: Linker
source                  1..5
                        mol_type = protein
                        organism = synthetic construct
SEQUENCE: 88
EAAAK                                                                     5
```

-continued

```
SEQ ID NO: 89              moltype = AA   length = 15
FEATURE                    Location/Qualifiers
REGION                     1..15
                           note = Synthetic: Linker
source                     1..15
                           mol_type = protein
                           organism = synthetic construct
SEQUENCE: 89
EAAAKEAAAK EAAAK                                                          15

SEQ ID NO: 90              moltype = AA   length = 109
FEATURE                    Location/Qualifiers
REGION                     1..109
                           note = Synthetic: a6
source                     1..109
                           mol_type = protein
                           organism = synthetic construct
SEQUENCE: 90
LAKTTQPISM DSYEGQEVNI TCSHNHIAAN DFITWYQQFP SQGPRFFIQG YKTNVSNEVA          60
SLFIPADRKS STLSLPRVSL SDTAVYYCLA WGGTDMLIFG TGTRLQVFP                    109

SEQ ID NO: 91              moltype = AA   length = 116
FEATURE                    Location/Qualifiers
REGION                     1..116
                           note = Synthetic: b6
source                     1..116
                           mol_type = protein
                           organism = synthetic construct
SEQUENCE: 91
EAGVAQSPRY KIIEKRQSVA FWCNPISGHG TLYWYQQILG QGPKLLIQFH NNGVVDDSQL          60
PKDRFSAERL KGVDSTLKIQ PAKLEDSAVY LCASSLDWVG DGERQYFGPG TRLLVL            116

SEQ ID NO: 92              moltype = AA   length = 116
FEATURE                    Location/Qualifiers
REGION                     1..116
                           note = Synthetic: b3
source                     1..116
                           mol_type = protein
                           organism = synthetic construct
SEQUENCE: 92
EAGVAQSPRY KIIEKRQSVA FWCNPIAGHG TLYWYQQILG QGPKLLIQFH ENRVVDDSQL          60
PKDRFSAERL KGVDSTLKIQ PAKLEDSAVY LCASSLDWVG SGETQYFGPG TRLLVL            116

SEQ ID NO: 93              moltype = AA   length = 1187
FEATURE                    Location/Qualifiers
REGION                     1..1187
                           note = Synthetic: a40b23U28-mol93
source                     1..1187
                           mol_type = protein
                           organism = synthetic construct
SEQUENCE: 93
AIQMTQSPSS LSASVGDRVT ITCRASQDIR NYLNWYQQKP GKAPKLLIYY TSRLESGVPS          60
RFSGSGSGTD YTLTISSLQP EDFATYYCQQ GNTLPWTFGQ GTKVEIKGGG GSGGGGSGGG         120
GSGGGGSGGG SEVQLVESGG GLVQPGGSLR LSCAASGYSF TGYAMNWVRQ APGKGLEWVA         180
LINPYKGVST YNQKFKDRFT FSVDKSKNTA YLQMNSLRAE DTAVYYCARS GYYGDSDWYF         240
DVWGQGTLVT VSSGGGGSEA GVAQSPRYKI IEKRQSVAFW CNPISGHGTL YWYQQILGQG         300
PKLLIQFHEN GVVDDSQLPK DRFSAERLKG VDSTLKIQPA KLEDSAVYLC ASSVDWGDG          360
ERQYFGPGTR LLVLEDLKNV FPPEVAVFEP SEAEISHTQK ATLVCLATGF YPDHVELSWW         420
VNGKEVHSGV CTDPQPLKEQ PALQDSRYAL SSRLRVSATF WQDPRNHFRC QVQFYGLSEN         480
DEWTQDRAKP VTQIVSAEAW GRADGGGSGG GGEPKSSDKT HTCPPCPAPE LLGGPSVFLF         540
PPKPKDTLMI SRTPEVTCVV VDVSHEDPEV KFNWYVDGVE VHNAKTKPRE EQYGSTYRVV         600
SVLTVLHQDW LNGKEYKCKV SNKALPAPIE KTISKAKGQP REPQVYTLPP SRDELTKNQV         660
SLSCAVKGFY PSDIAVEWES NGQPENNYKT TPPVLDSDGS FFLVSKLTVD KSRWQQGNVF         720
SCSVMHEALH NHYTQKSLSL SPGKGGGSGG GGLAKTTQPI SMDSYEGQEV NITCSHNYIA         780
ANDFITWYQQ FPSQGPRFFI QGYKTNVQNE VASLFIPADR KSSTLSLPRV SLSDTAVYYC         840
LAWGGTDLLP FGTGTRLQVF PNIQNPDPAV YQLRDSKSSD KSVCLFTDFD SQTQVSQSKD         900
SDVYITDKCV LDMRSMDFKS NSAVAWSQKS DFACANAFQN SIIPEDTGGG SGGGGEPKSS         960
DKTHTCPPCP APELLGGPSV FLFPPKPKDT LMISRTPEVT CVVVDVSHED PEVKFNWYVD        1020
GVEVHNAKTK PREEQYGSTY RVVSVLTVLH QDWLNGKEYK CKVSNKALPA PIEKTISKAK        1080
GQPREPQVYT LPPSRDELTK NQVSLWCLVK GFYPSDIAVE WESNGQPENN YKTTPPVLDS        1140
DGSFFLYSKL TVDKSRWQQG NVFSCSVMHE ALHNHYTQKS LSLSPGK                    1187

SEQ ID NO: 94              moltype = AA   length = 15
FEATURE                    Location/Qualifiers
REGION                     1..15
                           note = Synthetic: Fc hinge
source                     1..15
                           mol_type = protein
                           organism = synthetic construct
```

```
SEQUENCE: 94
EPKSSDKTHT CPPCP                                                         15

SEQ ID NO: 95           moltype = AA  length = 217
FEATURE                 Location/Qualifiers
REGION                  1..217
                        note = Synthetic: first Fc domain
source                  1..217
                        mol_type = protein
                        organism = synthetic construct
SEQUENCE: 95
APELLGGPSV FLFPPKPKDT LMISRTPEVT CVVVDVSHED PEVKFNWYVD GVEVHNAKTK          60
PREEQYGSTY RVVSVLTVLH QDWLNGKEYK CKVSNKALPA PIEKTISKAK GQPREPQVYT         120
LPPSRDELTK NQVSLSCAVK GFYPSDIAVE WESNGQPENN YKTTPPVLDS DGSFFLVSKL         180
TVDKSRWQQG NVFSCSVMHE ALHNHYTQKS LSLSPGK                                  217

SEQ ID NO: 96           moltype = AA  length = 217
FEATURE                 Location/Qualifiers
REGION                  1..217
                        note = Synthetic: second Fc domain
source                  1..217
                        mol_type = protein
                        organism = synthetic construct
SEQUENCE: 96
APELLGGPSV FLFPPKPKDT LMISRTPEVT CVVVDVSHED PEVKFNWYVD GVEVHNAKTK          60
PREEQYGSTY RVVSVLTVLH QDWLNGKEYK CKVSNKALPA PIEKTISKAK GQPREPQVYT         120
LPPSRDELTK NQVSLWCLVK GFYPSDIAVE WESNGQPENN YKTTPPVLDS DGSFFLYSKL         180
TVDKSRWQQG NVFSCSVMHE ALHNHYTQKS LSLSPGK                                  217

SEQ ID NO: 97           moltype = AA  length = 9
FEATURE                 Location/Qualifiers
REGION                  1..9
                        note = Synthetic: DOCK11
source                  1..9
                        mol_type = protein
                        organism = synthetic construct
SEQUENCE: 97
MLDKYSHYL                                                                  9

SEQ ID NO: 98           moltype =     length =
SEQUENCE: 98
000

SEQ ID NO: 99           moltype =     length =
SEQUENCE: 99
000

SEQ ID NO: 100          moltype =     length =
SEQUENCE: 100
000

SEQ ID NO: 101          moltype = AA  length = 7
FEATURE                 Location/Qualifiers
REGION                  1..7
                        note = Synthetic: TCRa CDR1
VARIANT                 2
                        note = I or V or L
VARIANT                 3
                        note = A or G
VARIANT                 6
                        note = D or E
source                  1..7
                        mol_type = protein
                        organism = synthetic construct
SEQUENCE: 101
YXXANXF                                                                    7

SEQ ID NO: 102          moltype =     length =
SEQUENCE: 102
000

SEQ ID NO: 103          moltype =     length =
SEQUENCE: 103
000

SEQ ID NO: 104          moltype = AA  length = 10
FEATURE                 Location/Qualifiers
REGION                  1..10
                        note = Synthetic: TCRa CDR3
```

```
source                  1..10
                        mol_type = protein
                        organism = synthetic construct
SEQUENCE: 104
XXXGGTDXXX                                                                          10

SEQ ID NO: 105          moltype = AA  length = 10
FEATURE                 Location/Qualifiers
REGION                  1..10
                        note = Synthetic: TCRa CDR3
VARIANT                 8
                        note = K or V or L
VARIANT                 10
                        note = I or P
source                  1..10
                        mol_type = protein
                        organism = synthetic construct
SEQUENCE: 105
XXXGGTDXXX                                                                          10

SEQ ID NO: 106          moltype = AA  length = 10
FEATURE                 Location/Qualifiers
REGION                  1..10
                        note = Synthetic: TCRa CDR3
VARIANT                 1
                        note = V or I or L
VARIANT                 2
                        note = A or G
VARIANT                 3
                        note = Y or W or F
VARIANT                 8
                        note = K or V or L
VARIANT                 9
                        note = V or I or L
VARIANT                 10
                        note = I or P
source                  1..10
                        mol_type = protein
                        organism = synthetic construct
SEQUENCE: 106
XXXGGTDXXX                                                                          10

SEQ ID NO: 107          moltype = AA  length = 10
FEATURE                 Location/Qualifiers
REGION                  1..10
                        note = Synthetic: TCRa CDR3
VARIANT                 1
                        note = V or I or L
VARIANT                 2
                        note = A or G
VARIANT                 3
                        note = Y or W or F
VARIANT                 9
                        note = V or I or L
source                  1..10
                        mol_type = protein
                        organism = synthetic construct
SEQUENCE: 107
XXXGGTDLXP                                                                          10

SEQ ID NO: 108          moltype =   length =
SEQUENCE: 108
000

SEQ ID NO: 109          moltype =   length =
SEQUENCE: 109
000

SEQ ID NO: 110          moltype =   length =
SEQUENCE: 110
000

SEQ ID NO: 111          moltype =   length =
SEQUENCE: 111
000

SEQ ID NO: 112          moltype =   length =
SEQUENCE: 112
000
```

```
SEQ ID NO: 113         moltype =   length =
SEQUENCE: 113
000

SEQ ID NO: 114         moltype = AA  length = 14
FEATURE                Location/Qualifiers
REGION                 1..14
                       note = Synthetic: TCRb CDR3
VARIANT                1
                       note = A or G
VARIANT                2
                       note = S or T
VARIANT                3
                       note = S or T
VARIANT                6
                       note = Y or W or F
VARIANT                9
                       note = S or D
VARIANT                10
                       note = A or G
VARIANT                11
                       note = D or E
VARIANT                13
                       note = Q or N
VARIANT                14
                       note = Y or W or F
source                 1..14
                       mol_type = protein
                       organism = synthetic construct
SEQUENCE: 114
XXXVDXVGXX XRXX                                                           14

SEQ ID NO: 115         moltype = AA  length = 14
FEATURE                Location/Qualifiers
REGION                 1..14
                       note = Synthetic: TCRb CDR3
VARIANT                1
                       note = A or G
VARIANT                2
                       note = S or T
VARIANT                3
                       note = S or T
VARIANT                6
                       note = Y or W or F
VARIANT                10
                       note = A or G
VARIANT                11
                       note = D or E
VARIANT                13
                       note = Q or N
VARIANT                14
                       note = Y or W or F
source                 1..14
                       mol_type = protein
                       organism = synthetic construct
SEQUENCE: 115
XXXVDXVGDX XRXX                                                           14

SEQ ID NO: 116         moltype = AA  length = 86
FEATURE                Location/Qualifiers
REGION                 1..86
                       note = Synthetic: aCD reduced glycosylation
source                 1..86
                       mol_type = protein
                       organism = synthetic construct
SEQUENCE: 116
NIQNPDPAVY QLRDSKSSDK SVCLFTDFDS QTQVSQSKDS DVYITDKCVL DMRSMDFKSN          60
SAVAWSQKSD FACANAFQNS IIPEDT                                              86

SEQ ID NO: 117         moltype = AA  length = 130
FEATURE                Location/Qualifiers
REGION                 1..130
                       note = Synthetic: bCD reduced glycosylation
source                 1..130
                       mol_type = protein
                       organism = synthetic construct
SEQUENCE: 117
EDLKNVFPPE VAVFEPSEAE ISHTQKATLV CLATGFYPDH VELSWWVNGK EVHSGVCTDP          60
```

```
QPLKEQPALQ DSRYALSSRL RVSATFWQDP RNHFRCQVQF YGLSENDEWT QDRAKPVTQI    120
VSAEAWGRAD                                                         130

SEQ ID NO: 118          moltype = AA  length = 34
FEATURE                 Location/Qualifiers
REGION                  1..34
                        note = Synthetic: FR3
source                  1..34
                        mol_type = protein
                        organism = synthetic construct
SEQUENCE: 118
VQNEVASLFI SADRKSSTLS LPRVSLSDTA VYYC                               34

SEQ ID NO: 119          moltype = AA  length = 504
FEATURE                 Location/Qualifiers
REGION                  1..504
                        note = Synthetic: b23U28
source                  1..504
                        mol_type = protein
                        organism = synthetic construct
SEQUENCE: 119
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSSGGGGSEA GVAQSPRYKI IEKRQSVAFW CNPISGHGTL YWYQQILGQG   300
PKLLIQFHEN GVVDDSQLPK DRFSAERLKG VDSTLKIQPA KLEDSAVYLC ASSVDWVGDG   360
ERQYFGPGTR LLVLEDLKNV FPPEVAVFEP SEAEISHTQK ATLVCLATGF YPDHVELSWW   420
VNGKEVHSGV CTDPQPLKEQ PALNDSRYAL SSRLRVSATF WQDPRNHFRC QVQFYGLSEN   480
DEWTQDRAKP VTQIVSAEAW GRAD                                         504
```

BINDING MOLECULES

REFERENCE TO ELECTRONIC SEQUENCE LISTING

The application contains a Sequence Listing which has been submitted electronically in .XML format and is hereby incorporated by reference in its entirety. Said .XML copy, created on Jan. 3, 2024, is named "0282-0006US1.xml" and is 158,419 bytes in size. The sequence listing contained in this .XML file is part of the specification and is hereby incorporated by reference herein in its entirety.

FIELD OF THE INVENTION

The present invention relates to binding molecules that comprise T cell receptor (TCR) variable domains and which can bind to a PIWIL1 peptide-HLA complex. The invention also relates to the use of such molecules for the treatment of malignant diseases.

BACKGROUND TO THE INVENTION

T cell receptors (TCRs) are naturally expressed by CD4+ and CD8+ T cells. TCRs are designed to recognize short peptide antigens that are displayed on the surface of antigen presenting cells in complex with Major Histocompatibility Complex (MHC) molecules (in humans, MHC molecules are also known as Human Leukocyte Antigens, or HLA) (Davis et al., Annu Rev Immunol. 1998; 16:523-44). CD8+ T cells, which are also termed cytotoxic T cells, have TCRs that specifically recognize peptides bound to MHC class I molecules. CD8+ T cells are generally responsible for finding and mediating the destruction of diseased cells, including cancerous and virally infected cells. The affinity of cancer-specific TCRs in the natural repertoire for their corresponding antigen is typically low as a result of thymic selection, meaning that cancerous cells frequently escape detection and destruction. Novel immunotherapeutic approaches aimed at promoting cancer recognition by T cells offer a highly promising strategy for the development of effective anticancer treatments.

PIWIL1 (also known as piwi-like protein 1 or HIWI and having Uniprot accession number Q96J94) is associated with meiotic division and plays a central role during spermatogenesis. PIWIL and PIWIL-like proteins are known to be involved in oncogenic processes, such as cell renewal, cell migration, and cell invasion, and in disease progression. Expression of PIWIL1 has been reported in various tumours, including those in the colon and oesophagus, while expression in normal tissues is restricted to testis (He et al. BMC Cancer. 2009 Dec. 8; 9:426; Grochola et al. Br J Cancer. 2008 Oct. 7; 99(7):1083-8; Taubert et al. Oncogene. 2007 Feb. 15; 26(7):1098-100; Li et al. Oncol Rep. 2010 April; 23(4):1063-8; Zeng et al. Chin Med J (Engl). 2011 July; 124(14):2144-9; WO2000032039). Overexpression of PIWIL has been associated with various tumour types, and PIWIL expression has been linked to poor prognosis in colorectal and gastric cancers (Dong et al. (2021), Critical Roles of PIWIL1 in Human Tumours: Expression, Functions, Mechanisms, and Potential Clinical Implications, *Front. Cell Dev. Biol.,* 9:1-11, doi.org/10.3389/fcell.2021.656993; Gao, et al. (2018) PIWI-like protein 1 upregulation promotes gastric cancer invasion and metastasis. Onco Targets Ther. 11, 8783-8789. doi: 10.2147/OTT.S186827).

The peptide SLSNRLYYL (SEQ ID NO: 1) corresponds to amino acids 853-861 of the full length PIWIL protein and is presented on the cell surface in complex with HLA-A2 (also referred to as "HLA-A*02"). As used herein, "HLA-A*02" or its synonym "HLA-A2" are generally referring to HLA-A*02:01. This peptide-HLA complex provides a useful target for TCR-based immunotherapeutic intervention.

The identification of particular TCR sequences that bind to the SLSNRLYYL (SEQ ID NO: 1) in complex with HLA-A2 with high affinity and high specificity is advantageous for the development of novel immunotherapies. Therapeutic TCRs may be used, for example, as soluble targeting agents for the purpose of delivering cytotoxic agents to the tumour site or activating immune effector functions against the tumour cells (Lissin, et al., "High-Affinity Monoclonal T-cell receptor (mTCR) Fusions" in Fusion Protein Technologies for Biopharmaceuticals: Applications and Challenges. 2013. S. R. Schmidt, Wiley; Boulter et al., Protein Eng. 2003 September; 16(9):707-11; Liddy, et al., Nat Med. 2012 June; 18(6):980-7, or alternatively they may be used to engineer T cells for adoptive therapy (Fesnak et al., Nat Rev Cancer. 2016 Aug. 23; 16(9):566-81).

TCRs that bind to SLSNRLYYL (SEQ ID NO: 1) in complex with HLA-A2 have been reported previously (WO 2017/089771). However, these TCRs have not been engineered or characterised for use as therapeutic TCRs; indeed no affinity data are provided. As explained further herein, the production of a TCR engineered to have high affinity, particularly when balanced with other desirable features is not straightforward, and typically has a high attrition rate.

There is therefore a need for binding molecules, such as TCRs, capable of binding with high affinity and specificity to SLSNRLYYL (SEQ ID NO: 1) in complex with HLA-A2 for the development of new immunotherapies.

In the first instance, the skilled person needs to identify a suitable starting, or scaffold, sequence. Typically, such sequences may be obtained from natural sources e.g. from antigen responding T cells extracted from donor blood. Given the rarity of cancer specific T cells in the natural repertoire, it is often necessary to screen many donors, for example 20 or more, before a responding T cell may be found. The screening process may take several weeks or months, and even where a responding T cell is found, it may be unsuitable for immunotherapeutic use. For example, the response may be too weak and/or may not be specific for the target antigen. Alternatively, it may not be possible to generate a clonal T cell population, nor expand or maintain a given T cell line to produce sufficient material to identify the correct TCR chain sequences. TCR sequences that are suitable as starting, or scaffold, sequences should have one or more of the following properties: a good affinity for the target peptide-HLA complex, for example 200 µM or stronger; a high level of target specificity, e.g. relatively weak or no binding to alternative peptide-HLA complexes; be amenable to use in display libraries, such as phage display; be able to be refolded and purified at high yield; and maintain stability in purified form. Given the degenerate nature of TCR recognition, it is exceptionally hard even for skilled practitioners to be able to determine whether a particular scaffold TCR sequence has a specificity profile that would make it eligible for engineering for therapeutic use (Wooldridge, et al., J Biol Chem. 2012 Jan. 6; 287(2):1168-77).

The next challenge is to engineer the TCR to have a higher affinity towards the target antigen whilst retaining desirable characteristics such as specificity and yield. TCRs, as they exist in nature, have weak affinity for target antigen (low micromolar range) compared with antibodies, and TCRs against cancer antigens typically have weaker antigen recognition than viral specific TCRs (Aleksic, et al. Eur J Immunol. 2012 December; 42(12):3174-9). This weak affinity coupled with HLA down-regulation on cancer cells means that therapeutic TCRs for cancer immunotherapy typically require engineering to increase their affinity for target antigen and thus generate a more potent response. Such affinity increases are essential for soluble TCR-based reagents. In such cases, antigen-binding affinities in the nanomolar to picomolar range, with binding half-lives of several hours, are desirable. The improved potency generated by high affinity antigen recognition at low epitope numbers is exemplified in FIGS. 1e and 1f of Liddy et al. (Liddy, et al., Nat Med. 2012 June; 18(6):980-7). The affinity maturation process, typically involves the skilled person having to engineer specific mutations, including but not limited to substitutions, insertions and/or deletions, on to the starting TCR sequence in order to increase the strength of antigen recognition. Affinity maturation techniques are known in the art, for example the use of display libraries (Li et al., Nat Biotechnol. 2005 March; 23(3):349-54; Holler et al., Proc Natl Acad Sci USA. 2000 May 9; 97(10):5387-92). However, to produce significant increases in the affinity of a given TCR against a given target, the skilled person may have to engineer mutations from a large pool of possible alternatives. The specific mutations that produce significant increases in affinity are not predictable and there is a high attrition rate. In many cases, it may not be possible to achieve significant increases in affinity with a given TCR starting sequence.

The affinity maturation process must also take account of the necessity of maintaining TCR antigen specificity. Increasing the affinity of a TCR for its target antigen brings a substantial risk of revealing cross reactivity with other unintended targets as a result of the inherent degeneracy of TCR antigen recognition (Wooldridge, et al., J Biol Chem. 2012 Jan. 6; 287(2):1168-77; Wilson, et al., Mol Immunol. 2004 February; 40(14-15):1047-55; Zhao et al., J Immunol. 2007 Nov. 1; 179(9):5845-54). At a natural level of affinity, the recognition of the cross reactive antigen may be too low to produce a response. If a cross reactive antigen is displayed on normal healthy cells, there is a strong possibility of off-target binding in vivo which may manifest in clinical toxicity. Thus, in addition to increasing antigen binding strength, the skilled person must also engineer mutations and or combinations of mutations that allow the TCR to retain a high specificity for target antigen and demonstrate a good safety profile in preclinical testing. Again, suitable mutations and/or combinations of mutations are not predictable. The attrition rate at this stage is even higher and in many cases may not be achievable at all from a given TCR starting sequence.

DESCRIPTION OF THE INVENTION

As described further below, the present invention provides novel and potent binding molecules, comprising TCR variable domains, that are suitable for immunotherapeutic use against PIWIL1 positive tumour cells expressing HLA-A2, and thus providing an opportunity for treatment of relevant cancers, including cancers such as colon cancer. The identification of the binding molecule of the present invention required extensive engineering efforts with over fifteen TCR affinity maturation series explored. Even once a particular affinity maturation series was selected for further study, additional multiple rounds of affinity maturation were performed. Subsequent to this, further stability enhancements were engineered into the molecule, all of which were introduced while maintaining appropriate potency and affinity. These stability enhancements are advantageous for a TCR-based binding molecule to be capable of use in vivo, particularly in a patient, and are also critical for such a molecule to be manufactured for such use. Furthermore, the inventors have found low PIWIL1 peptide-HLA-A2 density in primary tumour tissues. Surprisingly, in spite of this low target density, binding molecules of the invention demonstrated good killing potency against PIWIL1-positive cell lines.

Binding Molecules

In a first aspect, the present invention provides a binding molecule comprising a TCR alpha chain variable domain and a TCR beta chain variable domain, wherein the binding molecule has the property of binding to SLSNRLYYL (SEQ ID NO: 1) in complex with HLA-A*02, wherein each of the alpha chain variable domain and the beta chain variable domain comprises FR1-CDR1-FR2-CDR2-FR3-CDR3-FR4, where FR is a framework region and CDR is a complementarity determining region, and (a) wherein the binding molecule contacts at least N4, R5, Y7 and Y8 of SLSNRLYYL (SEQ ID NO: 1); and/or (b) wherein the alpha chain CDR1 comprises the sequence X-X-X-X-N-X-Y/F (SEQ ID NO: 98), the alpha chain CDR3 comprises the sequence X-X-X-G-G-T-D-X-X-X (SEQ ID NO: 104), the beta chain CDR3 comprises the sequence X-X-X-X-D-X-V-G-S/D-X-X-X-X-X (SEQ ID NO: 112), where X is an amino acid.

SEQ ID NOs: 98, 104 and 112 referred to above are consensus sequences based on the inventors' identification of key CDR residues that contact the target peptide when the binding molecule is bound to SLSNRLYYL (SEQ ID NO: 1) in complex with HLA-A*02, as described in Example 7. The sequences are shown in the section below entitled "Description of the sequences".

The inventors have surprisingly identified binding molecules, comprising TCR variable domains, with a particularly high affinity (picomolar range), and a high degree of antigen specificity for the SLSNRLYYL (SEQ ID NO: 1)/HLA-A*02 complex, despite the difficulties described above. Said molecules demonstrate potent killing of PIWIL positive cancer cells when prepared as soluble reagents fused to a T cell redirecting moiety. The molecules of the invention thus have a particularly suitable profile for therapeutic use. Particular binding molecules of the invention were engineered from a suitable scaffold (e.g., "wildtype") TCR sequence into which a number of mutations were introduced to enhance affinity and/or stability, while maintaining high specificity.

In a second aspect, the present invention provides a binding molecule comprising a TCR alpha chain variable domain and a TCR beta chain variable domain, wherein the binding molecule has the property of binding to SLSNRLYYL (SEQ ID NO: 1) in complex with HLA-A*02, wherein each of the alpha chain variable domain and the beta chain variable domain comprises FR1-CDR1-FR2-CDR2-FR3-CDR3-FR4, where FR is a framework region and CDR is a complementarity determining region, and wherein (a) the alpha chain CDRs comprise or have the following sequences:

CDR1—YIAANDF (SEQ ID NO: 23), optionally with one, two or three mutations therein, CDR2—GYKTN (SEQ ID NO: 24), optionally with one, two or three mutations therein,
CDR3—LAWGGTDLLP (SEQ ID NO: 29), optionally with one, two, three or four mutations therein,
(b) the beta chain CDRs comprise or have the following sequences:
CDR1—SGHGT (SEQ ID NO: 37), optionally with one, two or three mutations therein,
CDR2—FHEEGV (SEQ ID NO: 45), optionally with one, two or three mutations therein,
CDR3—ASSVDWVGDGERQY (SEQ ID NO: 41), optionally with one, two, three, four or five mutations therein.

In a third aspect, the present invention provides a binding molecule comprising a TCR alpha chain variable domain and a TCR beta chain variable domain, wherein the binding molecule has the property of binding to SLSNRLYYL (SEQ ID NO: 1) in complex with HLA-A*02,
wherein each of the alpha chain variable domain and the beta chain variable domain comprises FR1-CDR1-FR2-CDR2-FR3-CDR3-FR4, where FR is a framework region and CDR is a complementarity determining region, and
wherein
(a) the alpha chain CDRs comprise or have the following sequences:
CDR1—NIATNDY (SEQ ID NO: 5), optionally with one, two or three mutations therein,
CDR2—GYKTK (SEQ ID NO: 6), optionally with one, two or three mutations therein,
CDR3—LAWGGTDKLI (SEQ ID NO: 7), optionally with one, two, three or four mutations therein,
(b) the beta chain CDRs comprise or have the following sequences:
CDR1—SGHAT (SEQ ID NO: 15), optionally with one, two or three mutations therein,
CDR2—FQNNGV (SEQ ID NO: 16), optionally with one, two or three mutations therein,
CDR3—ASSLDWVGSGETQY (SEQ ID NO: 17), optionally with one, two, three, four or five mutations therein.

In a fourth aspect, the present invention provides a binding molecule that specifically binds to, or has the property of binding to, a SLSNRLYYL (SEQ ID NO: 1)-HLA-A*02 complex, wherein the binding molecule comprises a TCR alpha chain variable domain and a TCR beta chain variable domain, wherein each variable domain comprises three complementarity determining regions designated CDR1, CDR2, and CDR3, and
(a) wherein the binding molecule contacts N4, R5, Y7 and Y8 of SLSNRLYYL (SEQ ID NO: 1); and/or
(b) wherein
the alpha chain CDR1 comprises the sequence X-X-X-X—N-X-Y/F (SEQ ID NO: 98),
the alpha chain CDR3 comprises the sequence X-X-X-G-G-T-D-X-X-X (SEQ ID NO: 104),
the beta chain CDR3 comprises the sequence X-X-X-X-D-X-V-G-S/D-X-X-X-X-X (SEQ ID NO: 112), where X is any amino acid.

As used herein, "the binding molecule" or "the binding molecule of the invention" refer to each of the binding molecules of the first, second, third and fourth aspects above, unless clearly indicated otherwise.

As used herein, the term "binding molecule" generally refers to a molecule capable of binding to a target antigen. The binding molecules of the invention comprise a TCR alpha chain variable domain and a TCR beta chain variable domain, which associate together to form a TCR binding site which is capable of binding to the SLSNRLYYL (SEQ ID NO: 1)-HLA-A*02 complex. As used herein, the phrase "binding to the SLSNRLYYL (SEQ ID NO: 1)-HLA-A*02 complex" is used interchangeably with "binding to SLSNRLYYL (SEQ ID NO: 1) in complex with HLA-A*02". The binding molecules of the invention may adopt a number of different formats as discussed herein. Furthermore, fragments of the binding molecules of the invention are also envisioned. A fragment refers to a portion of the binding molecule that retains binding to the target antigen.

The binding molecules of the invention comprise TCR variable domains, which may correspond to those from a native TCR, or more preferably the TCR variable domains may be engineered (i.e., contain mutations relative to the native sequence). Native TCR variable domains may also be referred to as wild-type, natural, parental, unmutated or scaffold domains. The binding molecules of the invention may have ideal therapeutic properties such as supra-physiological affinity for target, long binding half-life, high specificity for target and good stability. The invention also includes multispecific (e.g., bispecific), or multifunctional (e.g., bifunctional), or fusion, molecules that incorporate TCR variable domains described herein and a therapeutic moiety such as, for example, a T cell redirecting moiety. Such molecules can mediate a potent and specific response against PIWIL positive cancer cells by re-directing and activating T-cells. Furthermore, the use of binding molecules with supra-physiological affinity facilitates recognition of such cancer cells presenting low levels of the target peptide-HLA complex. Alternatively, the binding molecules may further comprise (e.g., by fusion) other therapeutic agents, and or diagnostic agents, and or be incorporated into engineered T cells for adoptive therapy.

The binding molecule of the invention may be in the form of a TCR, which comprises the TCR alpha chain variable domain and the TCR beta chain variable domain. The TCR may be a soluble TCR, i.e. a TCR that does not comprise a transmembrane domain and does not comprise an intracellular/cytoplasmic domain. The TCR domain sequences may be defined with reference to IMGT nomenclature which is widely known and accessible to those working in the TCR field. For example, see: LeFranc and LeFranc, (2001). "T cell Receptor Factsbook", Academic Press; Lefranc, (2011), Cold Spring Harb Protoc 2011(6): 595-603; Lefranc, (2001), Curr Protoc Immunol Appendix 1: Appendix 100; and Lefranc, (2003), Leukemia 17(1): 260-266. Briefly, aPTCRs consist of two disulphide linked chains. Each chain (alpha and beta) is generally regarded as having two domains, namely a variable and a constant domain. A short joining region connects the variable and constant domains and is typically considered part of the alpha variable domain. Additionally, the beta chain usually contains a short diversity region next to the joining region, which is also typically considered part of the beta variable domain. The variable domain of each chain is located N-terminally and comprises three Complementarity Determining Regions (CDRs) embedded in a framework sequence (FR). The CDRs comprise the recognition site for peptide-MHC binding. There are several genes coding for alpha chain variable (Vα) domains and several genes coding for beta chain variable (Vβ) domains, which are distinguished by their framework, CDR1 and CDR2 sequences, and by a partly defined CDR3 sequence. The Vα and Vβ genes are referred to in IMGT nomenclature by the prefix TRAV and TRBV respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000), Exp Clin Immunogenet 17(2): 107-114; Scaviner and Lefranc, (2000), Exp Clin Immunogenet 17(2): 97-106; LeFranc and LeFranc, (2001), "T cell Receptor Factsbook", Academic Press). The huge diversity of T cell receptor chains results from combinatorial rearrangements between the various V, J and D genes, which include allelic variants, and junctional diversity (Arstila, et al., (1999), Science 286(5441): 958-961; Robins et al., (2009), Blood 114(19): 4099-4107.) The constant, or C, domains of TCR alpha and beta chains are referred to as TRAC and TRBC respectively (Lefranc, (2001), Curr Protoc Immunol Appendix 1: Appendix 10).

Certain binding molecules of the invention preferably have a $K_D$ for the SLSNRLYYL (SEQ ID NO: 1)-HLA-A*02 complex of greater than (i.e. stronger than) the native TCR (also referred to as the non-mutated, or scaffold TCR). A higher affinity refers to a lower numerical value for $K_D$ and indicates stronger binding. The $K_D$ may be, for example, in the range of 1 µM to 50 µM. Binding molecules of the invention may have a $K_D$ for the target complex of from about (i.e. +/−10%) 1 µM to about 400 nM, from about 1 µM to about 1000 µM, from about 1 µM to about 500 µM or from about 1 µM to about 100 µM. Said binding molecules may additionally, or alternatively, have a binding half-life (T½) for the complex in the range of from about 0.5 min to about 50 h, from about 20 min to about 30 h, or from about 20 min to about 25 h. Preferably, binding molecules of the invention have a $K_D$ for the SLSNRLYYL (SEQ ID NO: 1)-HLA-A*02 complex of from about 1 µM to about 500 µM and/or a binding half-life from about 20 min to about 25 h. Such high-affinity is preferable for binding molecules in soluble format when associated with therapeutic agents and/or detectable labels. The affinity of a binding molecule may be measured at 25° C. Methods for determining affinity of binding molecules are described herein.

Binding molecules of the invention comprising native TCR variable domains may have a $K_D$ for the complex of from about 1 µM to about 200 µM, or from about 1 µM to about 100 µM. Such binding molecules may be preferable for adoptive therapy applications.

Certain preferred mutated binding molecules have a binding affinity for, and/or a binding half-life for, the SLSNRLYYL (SEQ ID NO: 1)-HLA-A*02 complex that is substantially higher than that of the native TCR. Increasing the binding affinity of a native TCR may reduce the specificity of the TCR for its peptide-MHC ligand; this is demonstrated in Zhao et al., (2007) J.Immunol, 179:9, 5845-5854. However, certain binding molecules of the invention surprisingly demonstrate a high level of specificity for the SLSNRLYYL (SEQ ID NO: 1)-HLA-A*02 complex, despite having substantially higher binding affinity than the native TCR.

The binding molecules of the invention preferably have the property of specifically binding to the SLSNRLYYL (SEQ ID NO: 1)-HLA-A*02 complex. As used herein, "specific" binding refers to a binding molecule that binds to the SLSNRLYYL (SEQ ID NO: 1)-HLA-A*02 complex with higher affinity than to other peptide-HLA complexes. Highly specific binding molecules of the invention are particularly suitable for therapeutic use due to the reduced risk of off-target effects. Specificity in the context of binding molecules of the invention can be determined according to their ability to recognise target cells that are antigen positive, whilst having minimal ability to recognise target cells that are antigen negative.

Specificity can be measured in vitro, for example, in cellular assays, such as ELISpot assays, such as those described herein e.g., in Examples 4, 5 and 6. To test specificity, the binding molecules may be in soluble form and associated with an immune effector, and/or may be expressed on the surface of cells, such as T cells. Specificity may be determined by measuring the level of T cell activation in the presence of antigen positive and antigen negative target cells as defined above. Minimal recognition of antigen negative target cells is defined as a level of T cell activation of less than 20%, preferably less than 10%, preferably less than 5%, and more preferably less than 1%, of the level produced in the presence of antigen positive target cells, when measured under the same conditions (i.e. using the same lots of target and effector cells) and at a therapeutically relevant TCR concentration. For soluble TCRs associated with an immune effector, a therapeutically relevant concentration may be defined as a concentration of $10^{-9}$ M or below, and/or a concentration of up to 100, preferably up to 1000, fold greater than the corresponding EC50 or IC50 value. Preferably, for soluble binding molecules associated with an immune effector there is at least a 10 fold difference, at least a 100 fold, at least 1000 fold, at least 10000 fold difference in EC50 or IC50 value between T cell activation against antigen positive cells relative to antigen negative cells—this difference may be referred to as a therapeutic window. Additionally or alternatively the therapeutic window may be calculated based on lowest effective concentrations ("LOEL") observed for normal cells and an infected cell. Antigen positive cells may be obtained by peptide-pulsing using a suitable peptide concentration to obtain a level of antigen presentation comparable to wt peptide presentation, or, they may naturally present said peptide. Preferably, both antigen positive and antigen negative cells are human cells.

Specificity may additionally, or alternatively, relate to the ability of a binding molecule to bind to the SLSNRLYYL (SEQ ID NO: 1)-HLA-A*02 complex and not to a panel of alternative peptide-HLA complexes. This may, for example, be determined by the Surface Plasmon Resonance (SPR) method described herein e.g., in Example 2. Said panel may contain at least 2, at least 3, at least 5, or at least 10, alternative peptide-HLA complexes. The alternative peptides may share a low level of sequence identity with SEQ ID NO: 1 and may be naturally or artificially presented. Alternative peptides are preferably derived from commonly expressed proteins and or proteins expressed in healthy human tissues. Binding of the binding molecule to the SLSNRLYYL (SEQ ID NO: 1)-HLA-A*02 complex may be at least 2 fold greater than to other naturally or artificially-presented peptide HLA complexes, more preferably at least 10 fold, or at least 50 fold or at least 100 fold greater, even more preferably at least 1000 fold greater. Natural variants of SLSNRLYYL (SEQ ID NO: 1) peptide may be excluded from the definition of alternative peptide-HLA complexes.

An alternative or additional approach to determine binding molecule specificity may be to identify the peptide recognition motif of the binding molecule using sequential mutagenesis, e.g. alanine scanning, of the target peptide. Residues that form part of the binding motif are those that are not permissible to substitution. Non-permissible substitutions may be defined as those peptide positions in which the binding affinity of the binding molecule is reduced by at least 50%, or preferably at least 80% relative to the binding affinity for the non-mutated peptide. Such an approach is further described in Cameron et al., (2013), Sci Transl Med. 2013 Aug. 7; 5 (197): 197ra103 and WO2014096803. Binding molecule specificity in this case may be determined by identifying alternative motif containing peptides, particularly alternative motif containing peptides in the human proteome, and testing these peptides for binding to the binding molecule. Binding of the binding molecule to one or more alternative peptides may indicate a lack of specificity. In this case further testing of binding molecule specificity via cellular assays may be required. A low tolerance for (alanine) substitutions in the central part of the peptide indicate that the TCR has a high specificity and therefore presents a low risk for cross-reactivity with alternative peptides.

A binding molecule having the property of specifically binding to the SLSNRLYYL (SEQ ID NO: 1)-HLA-A*02 complex may bind to this complex with higher affinity relative to another peptide-HLA-A*02 complex. The MLDKYSHYL (SEQ ID NO: 97)-HLA-A*02 complex is a mimetic of the target antigen (the SLSNRLYYL (SEQ ID NO: 1)-HLA-A*02 complex). In spite of having a particularly high affinity (picomolar range), certain binding molecules of the invention surprisingly retain a high degree of antigen specificity and do not bind to the MLDKYSHYL (SEQ ID NO: 97)-HLA-A*02 complex, or bind to said complex with a significantly lower affinity. In particular, the affinity window between binding to target and binding to mimetic may be at least 100 fold, at least 500 fold, at least 1000 fold, at least 2000 fold, at least 3000 fold, at least 4000 fold and preferably at least 5000 fold. The binding molecule may bind to the SLSNRLYYL (SEQ ID NO: 1)-HLA-A*02 complex with an affinity which is at least two-fold, at least three-fold, at least four-fold, at least five-fold, at least 6-fold, at least 10-fold, at least 100-fold, or at least 1000-fold higher than its affinity for a MLDKYSHYL (SEQ ID NO: 97)-HLA-A*02. Such specificity surprisingly be achieved by a mutation of the native S residue at position 101 of the beta chain. The S residue may mutated to D.

Certain binding molecules of the invention are able to generate a highly potent T cell response in vitro against antigen positive cells, in particular those cells presenting low levels of antigen (i.e. in the order of 5-100). Such binding molecules may be in soluble form and linked to an immune effector such as an anti-CD3 antibody. The T cell response that is measured may be the release of T cell activation markers such as Interferon γ or Granzyme B, or target cell killing, or other measure of T cell activation, such as T cell proliferation. Preferably a highly potent response is one with $EC_{50}$ value in the pM range, i.e. 1000 μM or lower.

The term 'mutations' encompasses designed substitutions, insertions and deletions (e.g., engineered or designed substitutions, insertions and deletions). Mutations to a native (also referred to as parental, natural, unmutated, wild type, or scaffold) binding molecule may confer beneficial therapeutic properties, such as higher affinity, higher stability, higher specificity and/or high potency. For example, mutations may include those that increase the binding affinity ($k_D$) and/or binding half life (T1/2) of the binding molecule to the SLSNRLYYL (SEQ ID NO: 1)-HLA-A*02 complex.

The term "stability" in the context of the present invention refers to physical and chemical stability and can be evaluated qualitatively and/or quantitatively using various analytical techniques that are described in the art and are reviewed in for example Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Such methods include the evaluation of aggregate formation (for example using size exclusion chromatography (SEC)), by measuring turbidity (for example by dynamic light scattering (DLS) or light obscuration (LO)) and/or by visual inspection (for example by determining colour and clarity).

The binding molecule of the invention may make contact, such as hydrogen bond contact, to at least N4, R5, Y7 and Y8 of SLSNRLYYL (SEQ ID NO: 1) in complex with HL-A-A*02. A binding "contact", as used herein, is a reference to a (e.g., non-covalent) interaction between atoms from one molecule and atoms from another molecule when the two molecules are bound together. For example, a peptide residue binding "contact" is a binding interaction formed between amino acid residues of the SLSNRLYYL (SEQ ID NO: 1) peptide, not the HLA, and amino acid residues of the binding molecule. The binding molecule, when bound to the SLSNRLYYL (SEQ ID NO: 1) HLA-A*02 complex, may contact at least residues N4, R5, Y7 and Y8 of the SLSNRLYYL (SEQ ID NO: 1) peptide. The binding molecule, when bound to the SLSNRLYYL (SEQ ID NO: 1) HLA-A*02 complex, may contact all of the peptide residues in positions 1 to 9 of the SLSNRLYYL (SEQ ID NO: 1) peptide. Binding contacts (i.e., non-covalent interactions between atoms from one molecule and atoms from another molecule when the two molecules are bound together) can be identified using any method known in the art, including X-ray crystallography and structural modelling as described herein.

Certain angles can be used to define the binding geometry of the interaction between a binding molecule of the invention and SLSNRLYYL (SEQ ID NO: 1) in complex with HLA-A*02. For example, the binding molecule may bind to SLSNRLYYL (SEQ ID NO: 1) in complex with HLA-A*02 with a crossing angle in the range of 53° to 75°, or preferably in the range of 59° to 68°. The binding molecule may bind to SLSNRLYYL (SEQ ID NO: 1) in complex with HLA-A*02 with a tilt angle in the range of −38° to −18°, preferably in the range of −32° to −24°. The binding molecule may bind to SLSNRLYYL (SEQ ID NO: 1) in complex with HLA-A*02 with a roll angle in the range of −25° to −5°, preferably in the range of −20° to −10°. Binding geometry of a binding molecule, such as crossing, tilt and roll angles, can be identified using any method known in the art, including x-ray crystallography and structural modelling as described herein. For example, methods of calculating these angles are described in Rudolph et al. (2006). Annu Rev Immunol. 24, 419-466.

In the binding molecules of the invention, there may be at least one mutation in the TCR alpha chain variable domain. There may be one, two, three, four, five, six, seven, eight, nine, ten, or more, mutations in the alpha chain CDRs (i.e. in total across all three CDRs). For example, there may be six mutations in the alpha chain CDRs. There may be three mutations in the alpha chain CDR1 and/or one mutation in the alpha chain CDR2 and/or two mutations in the alpha chain CDR3.

The binding molecule of the first aspect of the invention may comprise an alpha chain CDR1 comprising the sequence of any one of SEQ ID NOs: 98, 99, 100 and 101.

The binding molecule of the first aspect of the invention may comprise an alpha chain CDR3 comprising the sequence of any one of SEQ ID Nos: 104, 105, 106 and 107.

The binding molecule of the first aspect of the invention may comprise a beta chain CDR3 comprising the sequence of any one of SEQ ID Nos: 112, 113, 114 and 115.

The binding molecule of the first aspect of the invention may comprise
- an alpha chain CDR1 comprising the sequence of SEQ ID NO: 99,
- an alpha chain CDR3 comprising the sequence SEQ ID NO: 105, and
- a beta chain CDR3 comprising the sequence SEQ ID NO: 113.

The binding molecule of the first aspect of the invention may comprise
- an alpha chain CDR1 comprising the sequence Y/N-I/N/L-A/G-A/T-N-D/E-Y/F (SEQ ID NO: 100),
- an alpha chain CDR3 comprising the sequence V/I/L-A/G-Y/W/F-G-G-T-D-KN/L-V/I/L-I/P (SEQ ID NO: 106), and
- a beta chain CDR3 comprising the sequence A/G-S/T-S/T-V-D-Y/W/F-V-G-S/D-A/G-D/E-R-Q/N-Y/W/F (SEQ ID NO: 114).

The binding molecule of the first aspect of the invention may comprise
- an alpha chain CDR1 comprising the sequence Y-I//L-A/G-A-N-D/E-F (SEQ ID NO: 101),
- an alpha chain CDR3 comprising the sequence V/I/L-A/G-Y/W/F-G-G-T-D-L-V/I/L-P (SEQ ID NO: 107), and
- a beta chain CDR3 comprising the sequence A/G-S/T-S/T-V-D-Y/W/F-V-G-D-A/G-D/E-R-Q/N-Y/W/F (SEQ ID NO: 115).

The binding molecule of the first aspect of the invention may comprise
- an alpha chain CDR1 comprising the sequence Y/N-I/N/L-A/G-A/T-N-D/E-Y/F (SEQ ID NO: 100),
- an alpha chain CDR2 comprising the sequence G/A-Y/W/F-K/R/H-T/S-N(SEQ ID NO: 103),
- an alpha chain CDR3 comprising the sequence V/I/L-A/G-Y/W/F-G-G-T-D-KN/L-V/I/L-I/P (SEQ ID NO: 106),
- a beta chain CDR1 comprising the sequence S-A/G-K/R/H-G-S/T (SEQ ID NO: 109).
- a beta chain CDR2 comprising the sequence Y/W/F-H-E-E-A/G-V/I/L (SEQ ID NO: 111), and
- a beta chain CDR3 comprising the sequence A/G-S/T-S/T-V-D-Y/W/F-V-G-S/D-A/G-D/E-R-Q/N-Y/W/F (SEQ ID NO: 114).

The binding molecule of the first aspect may comprise
- an alpha chain CDR1 comprising the sequence YIAANDF (SEQ ID NO: 23), optionally with one, two or three mutations at any of positions 1-4 and 6 of SEQ ID NO: 23 (i.e. the mutations exclude N at position 7 and F at position 8 numbered according to SEQ ID NO: 3),
- an alpha chain CDR3 comprising the sequence LAWGGTDLLP (SEQ ID NO: 29), optionally with one, two, three or four mutations at any of positions 1-3 and 8-10 of SEQ ID NO: 29 (i.e. the mutations exclude G at position 4, G at position 5, T at position 6 and D at position 7); and/or
- a beta chain CDR3 comprising the sequence ASSVDWVGDGERQY (SEQ ID NO: 41), optionally with one, two, three or four mutations at any of positions 1-4, 6 and 10$^{-14}$ of SEQ ID NO: 41 (i.e. the mutations exclude D at position 5, V at position 7, G at position 8 and D at position 9).

The binding molecule of the first aspect may comprise
- an alpha chain CDR1 comprising the sequence YIAANDF (SEQ ID NO: 23), optionally with one or two mutations at any of positions 1-4 and 6 of SEQ ID NO: 23,
- an alpha chain CDR3 comprising the sequence LAWGGTDLLP (SEQ ID NO: 29), optionally with one, two or three mutations at any of positions 1-3 and 8-10 of SEQ ID NO: 29; and/or
- a beta chain CDR3 comprising the sequence ASSVDWVGDGERQY (SEQ ID NO: 41), optionally with one, two or three mutations at any of positions 1-4, 6 and 10$^{-14}$ of SEQ ID NO: 41.

The binding molecule of the first aspect may comprise
- an alpha chain CDR1 comprising the sequence YIAANDF (SEQ ID NO: 23), optionally with one mutation at any of positions 1-4 and 6 of SEQ ID NO: 23,
- a alpha chain CDR3 comprising the sequence LAWGGTDLLP (SEQ ID NO: 29), optionally with one or two mutations at any of positions 1-3 and 8-10 of SEQ ID NO: 29; and/or
- a beta chain CDR3 comprising the sequence ASSVDWVGDGERQY (SEQ ID NO: 41), optionally with one or two mutations at any of positions 1-4, 6 and 10$^{-14}$ of SEQ ID NO: 41.

The binding molecule of the first aspect may comprise
- an alpha chain CDR1 comprising the sequence YIAANDF (SEQ ID NO: 23), optionally with one mutation at any of positions 1-4 and 6 of SEQ ID NO: 23,
- a alpha chain CDR3 comprising the sequence LAWGGTDLLP (SEQ ID NO: 29), optionally with one mutation at any of positions 1-3 and 8-10 of SEQ ID NO: 29; and/or
- a beta chain CDR3 comprising the sequence ASSVDWVGDGERQY (SEQ ID NO: 41), optionally with one mutation at any of positions 1-4, 6 and 10$^{-14}$ of SEQ ID NO: 41.

The binding molecule of the first aspect may comprise:
- an alpha chain CDR2 comprising the sequence GYKTN (SEQ ID NO: 24), optionally with one, two or three mutations therein,
- a beta chain CDR1 comprising sequence SGHGT (SEQ ID NO: 37), optionally with one, two or three mutations therein, and
- a beta chain CDR2 comprising the sequence FHEEGV (SEQ ID NO: 45), optionally with one, two or three mutations therein.

The binding molecule of the first aspect may comprise:
- an alpha chain CDR2 comprising the sequence GYKTN (SEQ ID NO: 24), optionally with one or two mutations therein,
- a beta chain CDR1 comprising sequence SGHGT (SEQ ID NO: 37), optionally with one or two mutations therein, and
- a beta chain CDR2 comprising the sequence FHEEGV (SEQ ID NO: 45), optionally with one or two mutations therein.

The binding molecule of the first aspect may comprise:
- an alpha chain CDR2 comprising the sequence GYKTN (SEQ ID NO: 24), optionally with one mutation therein,
- a beta chain CDR1 comprising sequence SGHGT (SEQ ID NO: 37), optionally with one mutation therein, and
- a beta chain CDR2 comprising the sequence FHEEGV (SEQ ID NO: 45), optionally with one mutation therein.

The binding molecule of the first aspect of the invention may comprise an alpha chain CDR2 comprising the sequence G/A-Y/W/F-K/R/H-T/S-N/K (SEQ ID NO: 102), a beta chain CDR1 comprising the sequence S/T-A/G-K/R/

H-A/G-S/T (SEQ ID NO: 108) and a beta chain CDR2 comprising the sequence Y/W/F-H/Q-N/E-N/E-A/G-V/I/L (SEQ ID NO: 110). The binding molecule of the first aspect of the invention may comprise an alpha chain CDR2 comprising the sequence G/A-Y/W/F-K/R/H-T/S-N(SEQ ID NO: 103), a beta chain CDR1 comprising the sequence S-A/G-K/R/H-G-S/T (SEQ ID NO: 109) and a beta chain CDR2 comprising the sequence Y/W/F-H-E-E-A/G-V/I/L (SEQ ID NO: 111).

In the sequences specified herein, "X" represents any amino acid. The forward slash ("/") represents "or", e.g., "S/T" indicates that the amino acid can be S (Ser) or T (Thr) at the specified position in the sequence.

In the binding molecule of the third aspect of the invention, the mutations in the alpha chain CDRs may be selected from:

| | |
|---|---|
| N26(CDR1) | Y |
| T29 (CDR1) | A |
| Y32 (CDR1) | F |
| K54 (CDR2) | N |
| K96 (CDR3) | L or V |
| I98 (CDR3) | P | numbered according to SEQ ID NO: 3. Thus, there may be any or all of these mutations, optionally in combination with other mutations. In particular, the binding molecule may comprise the following mutations in the alpha chain CDRs, numbered according to SEQ ID NO: 3:
CDR1: N26Y, T29A, Y32F;
CDR2: K54N; and
CDR3: K96V, I98P
or
CDR1: N26Y, T29A, Y32F;
CDR2: K54N; and
CDR3: K96L, I98P The second set of mutations listed above is preferred.

In the binding molecule of the invention, the mutations in the alpha chain CDRs may be conservative, semi-conservative, tolerated or other phenotypically silent mutations, as described herein. Other suitable conservative, semi-conservative, tolerated or other phenotypically silent mutations will be apparent to those skilled in the art. Additional mutations may be those corresponding to residues within alpha chain sequences disclosed herein, including e.g., Y26N, A29T, F32Y, N54K, L96K, P98I, numbered according to SEQ ID NO: 34.

A mutated alpha chain variable domain may be paired with any beta chain variable domain defined herein.

There may be at least one mutation in the TCR beta chain variable domain of the binding molecules of the invention. There may be one, two, three, four, five, six, seven, eight, nine, ten or more, mutations in the beta chain CDRs (i.e. in total across all three CDRs). For example, there may be six or seven mutations in the beta chain CDRs. There may be one or two mutations in the beta chain CDR1 and/or two or three mutations in the beta chain CDR2 and/or five mutations in the beta chain CDR3.

In the binding molecule of the third aspect of the invention, the mutation(s) in the beta chain CDRs may be selected from:

| | |
|---|---|
| S27 (CDR1) | T |
| A30 (CDR1) | G |
| Q50 (CDR2) | H |
| N51 (CDR2) | E |
| N52 (CDR2) | E |
| L96 (CDR3) | V or W |
| S101 (CDR3) | D |
| T104 (CDR3) | R | numbered according to SEQ ID NO: 13. Thus, there may be any or all of these mutations, optionally in combination with other mutations. In particular, the binding molecule may comprise the following mutations in the beta chain CDRs, numbered according to SEQ ID NO: 13:
CDR1: A30G;
CDR2: Q50H, N51E; and
CDR3: L96V, S101D, T104R
or
CDR1:A30G;
CDR2: Q50H, N51E; and
CDR3: L96W, S101D, T104R
or
CDR1: S27T, A30G;
CDR2: Q50H, N51E; and
CDR3: L96V, S101D, T104R
or
CDR1: A30G;
CDR2: Q50H, N51E, N52E; and
CDR3: L96V, S101D, T104R.

The A30G, Q50H, N51 E, N52E, L96V, S101D and T104R set of mutations listed above are preferred.

In the binding molecule of the invention, the mutations in the beta chain CDRs may be conservative, semi-conservative, tolerated or other phenotypically silent mutations, as described herein. Other suitable conservative, semi-conservative, tolerated or other phenotypically silent mutations will be apparent to those skilled in the art. Additional mutations may be those corresponding to residues within alpha chain sequences disclosed herein, including e.g., G30A, H50Q, E51N, E52N, V96L, D101S, numbered according to SEQ ID NO: 48.

A mutated beta chain variable domain may be paired with any alpha chain variable domain defined herein.

Mutation(s) within the CDRs, relative to a native sequence, may improve the binding affinity or stability of the binding molecule of the invention but may additionally or alternatively confer other advantages such as improved specificity or improved potency when fused to an immune effector. Mutations may also reduce the risk of destabilising post-translational modifications, such as deamidation. One example of such a mutation is N52E in the beta chain variable domain of SEQ ID NO: 13. Mutations at one or more positions may additionally or alternatively affect the interaction of an adjacent position with the cognate pMHC complex, for example by providing a more favourable angle for interaction. Mutations may include those that result in a reduction in non-specific binding, i.e. a reduction in binding to alternative antigens relative to the SLSNRLYYL (SEQ ID NO: 1)-HLA-A*02 complex. Mutations may include those that increase efficacy of folding and/or stability and/or manufacturability. Some mutations may contribute to each of these characteristics; others may contribute to affinity but not to specificity, for example, or to specificity but not to affinity, or to stability but not affinity, etc.

At least 3, at least 5 or at least 10 CDR mutations, relative to a wild type sequence, in total may be needed to obtain binding molecules with pM affinity for target antigen. Binding molecules with pM affinity for their target antigen are especially suitable as soluble therapeutics. Binding molecules for use in adoptive therapy applications may have lower affinity for target antigen and thus fewer CDR mutations, for example, up to 1, up to 2, up to 5, or more CDR mutations in total. In some cases, the native (also referred to as unmutated) binding molecule may have a sufficiently high affinity for target antigen without the need for mutation. The binding molecules of the present invention in their native form also have advantageously high affinity and specificity.

The binding molecules of the invention may comprise one of the following combinations of alpha chain CDRs and beta chain CDRs:

| Combi-nation | Alpha | | | Beta | | |
|---|---|---|---|---|---|---|
| | CDR1 | CDR2 | CDR3 | CDR1 | CDR2 | CDR3 |
| 1 | YIAANDF (SEQ ID NO: 23) | GYKTN (SEQ ID NO: 24) | LAWGGTDLLP (SEQ ID NO: 29) | SGHGT (SEQ ID NO: 37) | FHENGV (SEQ ID NO: 38) | ASSVDWVGDGERQY (SEQ ID NO: 41) |
| 2 | YIAANDF (SEQ ID NO: 23) | GYKTN (SEQ ID NO: 24) | LAWGGTDVLP (SEQ ID NO: 29) | TGHGT (SEQ ID NO: 43) | FHENGV (SEQ ID NO: 38) | ASSVDWVGDGERQY (SEQ ID NO: 41) |
| 3 | YIAANDF (SEQ ID NO: 23) | GYKTN (SEQ ID NO: 24) | LAWGGTDLLP (SEQ ID NO: 29) | SGHGT (SEQ ID NO: 37) | FHENGV (SEQ ID NO: 38) | ASSWDWVGDGERQY (SEQ ID NO: 41) |
| 4 | YIAANDF (SEQ ID NO: 23) | GYKTN (SEQ ID NO: 24) | LAWGGTDLLP (SEQ ID NO: 29) | SGHGT (SEQ ID NO: 37) | FHEEGV (SEQ ID NO: 45) | ASSVDWVGDGERQY (SEQ ID NO: 41) |
| 5 | YIAANDF (SEQ ID NO: 23) | GYKTN (SEQ ID NO: 24) | LAWGGTDLLP (SEQ ID NO: 29) | SGHGT (SEQ ID NO: 37) | FHENGV (SEQ ID NO: 38) | ASSVDWVGDGERQY (SEQ ID NO: 41) |
| 6 | YIAANDF (SEQ ID NO: 23) | GYKTN (SEQ ID NO: 24) | LAWGGTDLLP (SEQ ID NO: 29) | SGHGT (SEQ ID NO: 37) | FHEEGV (SEQ ID NO: 45) | ASSVDWVGDGERQY (SEQ ID NO: 41) |
| 7 | NIATNDY (SEQ ID NO: 5) | GYKTK (SEQ ID NO: 24) | LAWGGTDKLI (SEQ ID NO: 7) | SGHAT (SEQ ID NO: 15) | FQNNGV (SEQ ID NO: 16) | ASSLDWVGSGETQY (SEQ ID NO: 41) |

A preferred combination is combination 6 in the table above. These are the CDR sequences of the TCR referred to as "a67b72" in the Examples.

Mutations may additionally, or alternatively, be made outside the CDRs, within the framework regions; such mutations may result in improved therapeutic properties, such as improve affinity, and/or specificity, and/or stability, and/or the yield of a purified soluble form of the binding molecule. For example, the binding molecules of the invention may, additionally or alternatively, comprise one or more mutations at the N terminus of FR1, of one of both chains, relative to the canonical framework sequences for a given TRAV and TRBV chain. Such mutations may improve the efficiency of N-terminal methionine cleavage. The removal of an N-terminal initiation methionine is often crucial for the function and stability of proteins. Inefficient cleavage may be detrimental for a therapeutic, since it may result in a heterogeneous protein product, and or the presence of the initiation methionine may be immunogenic in humans. In some cases an initiation methionine may be present in the binding molecules of the invention. Mutations may be made to remove or modify glycosylation sites.

The alpha chain variable domain framework regions of the binding molecule of the invention may comprise the following sequences:

FR1—LAKTTQPISMDSYEGQEVNITCSHN (SEQ ID NO: 8), optionally with one, two or three mutations therein, FR2—ITWYQQFPSQGPRFIIQ (SEQ ID NO: 9), optionally with one, two or three mutations therein, FR3—VTNEVASLFIPADRKSSTLSLPRVSLSD-TAVYYC (SEQ ID NO: 10), optionally with one, two or three mutations therein, FR4—FGTGTRLQVFP(SEQ ID NO: 11), optionally with one, two or three mutations therein, and/or the beta chain variable domain framework regions comprise the following sequences:

FR1—EAGVAQSPRYKIIEKRQSVAFWCNPI (SEQ ID NO: 18), optionally with one, two or three mutations therein, FR2—LYWYQQILGQGPKLLIQ (SEQ ID NO: 19), optionally with one, two or three mutations therein, FR3—VDDSQLPKDRFSAERLKGVDSTLKIQPAK-LEDSAVYLC (SEQ ID NO: 20), optionally with one, two or three mutations therein, FR4—FGPGTRLLVL (SEQ ID NO: 21), optionally with one, two or three mutations therein.

The alpha chain framework regions FR1, FR2, and FR3 may comprise amino acid sequences corresponding to a TRAV4 chain and/or the beta chain framework regions FR1, FR2 and FR3, may comprise amino acid sequences corresponding to those of a TRBV11-2 chain.

The FR4 region may comprise the joining region of the alpha and beta variable chains (TRAJ and TRBJ, respectively). The TRAJ region may comprise amino acid sequences corresponding to those of TRAJ34-1. The TRBJ region may comprise amino acid sequences corresponding to those of TRBJ5-1.

The alpha chain variable domain framework regions may have one, two, three, four, five or more mutations in total, relative to the above sequences. The alpha chain variable domain framework regions may have five mutations, relative to the above sequences. The alpha chain variable domain framework regions may comprise one or more of the following mutations:

| | |
|---|---|
| L1 | A |
| T21 | P |
| I47 | F |
| T56 | Q |
| P65 | S | numbered according to SEQ ID NO: 3. The mutations to I47 and T56 may improve affinity. The mutations to L1, T21 and P65 may improve manufacturability and/or stability. The alpha chain variable domain framework region may comprise one of the following combinations of mutations:
  (a) I47F, T56Q
  (b) L1A, I47F, T56Q
  (c) T21P, I47F, T56Q, P65S
  (d) L1A, T21P, I47F, T56Q, P65S numbered according to SEQ ID NO: 3. A preferred combination is combination (d) above. The alpha chain variable domain framework regions may comprise no other mutations (other than those listed above).

The beta chain variable domain framework regions may have one, two, three, four, five or more mutations in total, relative to the above sequences. The beta chain variable domain framework regions may have one mutations, relative to the above sequences. The beta chain variable domain framework regions comprise the following mutation: R16G numbered according to SEQ ID NO: 13. This mutation may improve stability. The beta chain variable domain framework regions may comprise no other mutations relative to the above sequences.

The alpha chain variable domain of the binding molecule of the invention may comprise respective framework amino acid sequences that have at least 90%, at least 91%, at least 92%, at least 93%, at least 94%, at least 95%, at least 96%, at least 97%, at least 98% or at least 99% identity to SEQ ID NOs: 8, 9, 10 and 11. The beta chain variable domain of the binding molecule of the invention may comprise respective framework amino acid sequences that have at least 90%, at least 91%, at least 92%, at least 93%, at least 94%, at least 95%, at least 96%, at least 97%, at least 98% or at least 99% identity to SEQ ID NOs: 18, 19, 20 and 21. Alternatively, the stated percentage identity may be over the framework sequences when considered as a whole.

The alpha chain variable domain may comprise any one of the amino acid sequences of SEQ ID NOs: 3, 22, 28, 30, 32, 34, 49, 51, 54, 56, 58 or 90, or an amino acid sequence having at least 80%, at least 90%, at least 95% or at least 98% identity to any one of SEQ ID NOs: 3, 22, 28, 30, 32, 34, 49, 51, 54, 56, 58 or 90. The beta chain variable domain may comprise any one of the amino acid sequences of SEQ ID NOs: 13, 36, 40, 42, 44, 46, 48, 50, 52, 53, 55, 57, 59, 91 or 92, or an amino acid sequence having at least 80%, at least 90%, at least 95% or at least 98% identity to any one of SEQ ID NOs: 13, 36, 40, 42, 44, 46, 48, 50, 52, 53, 55, 57, 59, 91 or 92. As all alpha chain variable domains and beta chain variable domains are derived from the same scaffold TCR sequences (i.e., SEQ ID NO: 2 and SEQ ID NO: 12 respectively), it is expected that all alpha chain variable domain sequences are compatible with all beta chain variable domain sequences. Thus, the alpha chain variable domain may comprise an amino acid sequence provided in any one of SEQ ID NOs: 3, 22, 28, 30, 32, 34, 49, 51, 54, 56, 58 or 90, or an amino acid sequence with at least 90% identity thereto, and the beta chain variable domain may comprise an amino acid sequence provided in any one of SEQ ID NOs: 13, 36, 40, 42, 44, 46, 48, 50, 52, 53, 55, 57, 59, 91 or 92, or an amino acid sequence with at least 90% identity thereto.

The alpha chain variable domain may comprise any one of the amino acid sequences of SEQ ID NOs: 3, 22, 28, 30, 32 and 34, or an amino acid sequence having at least 80%, at least 90%, at least 95% or at least 98% identity to any one of SEQ ID NOs: 3, 22, 28, 30, 32 and 34. The beta chain variable domain may comprise any one of the amino acid sequences of SEQ ID NOs: 13, 36, 40, 44, 46 and 48, or an amino acid sequence having at least 80%, at least 90%, at least 95% or at least 98% identity to any one of SEQ ID NOs: 13, 36, 40, 44, 46 and 48. As all alpha chain variable domains and beta chain variable domains are derived from the same scaffold TCR sequences (i.e., SEQ ID NO: 2 and SEQ ID NO: 12 respectively), it is expected that all alpha chain variable domain sequences are compatible with all beta chain variable domain sequences. Thus, the alpha chain variable domain may comprise an amino acid sequence provided in any one of SEQ ID NOs: 3, 22, 28, 30, 32 and 34, or an amino acid sequence with at least 90% identity thereto, and the beta chain variable domain may comprise an amino acid sequence provided in any one of SEQ ID NOs: 13, 36, 40, 44, 46 and 48, or an amino acid sequence with at least 90% identity thereto.

The binding molecule may comprise one of the following combinations of alpha and beta chain variable domains:

| | Alpha chain variable domain SEQ ID NO | Beta chain variable domain SEQ ID NO |
|---|---|---|
| 1 | 22 | 42 |
| 2 | 28 | 36 |
| 3 | 28 | 40 |
| 4 | 30 | 44 |
| 5 | 32 | 46 |
| 6 | 34 | 48 |

Preferably, the alpha chain variable domain comprises the amino acid sequence of SEQ ID NO: 34 and the beta chain variable domain comprises the amino acid sequence of SEQ ID NO: 48. In this regard, the invention provides a binding molecule having the property of binding to SLSNRLYYL (SEQ ID NO: 1) in complex with HLA-A*02, wherein the binding molecule comprises an alpha chain variable domain comprising the amino acid sequence provided in SEQ ID NO: 34, or an amino acid sequence having at least 80%, at least 90%, at least 95% or at least 98% identity to SEQ ID NO: 34, and a beta chain variable domain comprising the amino acid sequence provided in SEQ ID NO: 48, or an amino acid sequence having at least 80%, at least 90%, at least 95% or at least 98% identity to SEQ ID NO: 48.

The alpha chain variable domain may comprise the amino acid sequence of SEQ ID NO: 28 [a40] and the beta chain variable domain comprises the amino acid sequence of SEQ ID NO: 36 [b23]. In this regard, the invention provides a binding molecule having the property of binding to SLSNR-LYYL (SEQ ID NO: 1) in complex with HLA-A*02, wherein the binding molecule comprises an alpha chain variable domain comprising the amino acid sequence provided in SEQ ID NO: 28, or an amino acid sequence having at least 80%, at least 90%, at least 95% or at least 98% identity to SEQ ID NO: 28, and a beta chain variable domain comprising the amino acid sequence provided in SEQ ID NO: 36, or an amino acid sequence having at least 80%, at least 90%, at least 95% or at least 98% identity to SEQ ID NO: 36.

In the binding molecules of the invention, the variable domains, and where present the constant domains and/or any other domains, may be organised in any suitable format/arrangement that allows antigen binding. As used herein, a "format" of an binding molecule specifies a defined spatial arrangement of domains, in particular variable and optionally constant domains. Characteristics of such protein formats are the number of polypeptide chains (single chain, double chain or multiple chains), the type and length of linkers connecting different domains, the number of antigen binding moieties (and thus the number of valences), the number of different antigen binding moieties (and thus the number of specificities for different antigens, e.g. bispecific, multispecific), and the order and orientation of variable domains (e.g. cross-over, parallel). For example, the variable domains may be arranged in monoclonal TCR format, in which the two chains are linked by a disulphide bond, either within the constant domains or variable domains, or in which the variable domains are fused to one or more dimerization domains. Alternatively the variable domains may be arranged in single chain format in the present or absence of one or more constant domains, or the variable domains may be arranged in diabody format. Other suitable formats may be used.

Binding molecules of the invention may comprise at least one TCR constant domain or fragment thereof, for example an alpha chain TRAC constant domain and/or a beta chain TRBC1 or TRBC2 constant domain. As will be appreciated by those skilled in the art the term TRAC and TRBC1/2 also encompasses natural polymorphic variants, for example N to K at position 4 of TRAC (Bragado et al International immunology. 1994 February; 6(2):223-30).

Where present, one or both of the constant domains may contain mutations, substitutions or deletions relative to native constant domain sequences. The constant domains may be truncated, i.e. having no transmembrane or cytoplasmic domains. Thus, the binding molecule of the invention may comprise the extracellular region of a TCR alpha chain constant domain and/or the extracellular region of a TCR beta chain constant domain. Alternatively, the constant domains may be full-length by which it is meant that extracellular, transmembrane and cytoplasmic domains are all present. The TRAC and TRBC domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may have an introduced disulphide bond between residues of the respective constant domains, as described, for example, in WO 03/020763. Thus, the binding molecule may comprise a non-native covalent disulphide bond that links a residue of the TCR alpha chain constant domain to a residue of the TCR beta chain constant domain. Preferably the alpha and beta constant domains may be modified by substitution of cysteine residues at position Thr 48 of TRAC and position Ser 57 of TRBC1 or TRBC2, the said cysteines forming a non-natural disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. One or both of the extracellular constant domains, e.g., present in an as heterodimer, may be further truncated at the C terminus or C termini, for example by up to 15, or up to 10, or up to 8 or fewer amino acids. One or both of the extracellular constant domains, e.g., present in an as heterodimer, may be truncated at the C terminus or C termini by, for example, up to 15, or up to 10 or up to 8 amino acids. The C terminus of the alpha chain extracellular constant domain may be truncated by 8 amino acids.

The alpha and or beta constant domain may additionally or alternatively contain mutations to improve manufacturability, for example to remove or alter glycosylation sites. Such mutations are typically required for production in mammalian systems such as CHO cells. SEQ ID NO 116 and SEQ ID NO: 117 provide respective alpha and beta constant domain sequences suitable for manufacturing in mammalian cells.

A binding molecule of the invention may comprise the extracellular region of a TCR alpha chain constant domain, optionally truncated at the C terminus by up to 15 amino acids, and/or the extracellular region of a TCR beta chain constant domain, optionally truncated at the C terminus by up to 15 amino acids.

The TCR alpha chain constant domain may comprise the amino acid sequence provided in SEQ ID NO: 4, or an amino acid sequence that has at least 90% identity to the sequence provided in SEQ ID NO: 4, and/or the TCR beta chain constant domain may comprise the amino acid sequence provided in SEQ ID NO: 14, or an amino acid sequence that has at least 90% identity to the sequence provided in SEQ ID NO:14.

The binding molecule may comprise the extracellular region of a TCR alpha chain constant domain comprising the amino acid sequence provided in SEQ ID NO: 4 and the extracellular region of a TCR beta chain constant domain comprising the amino acid sequence provided in SEQ ID NO: 14. The binding molecule may not comprise a transmembrane or cytoplasmic domain of a TCR.

Alternatively, rather than full-length or truncated constant domains there may be no TCR constant domains. Accordingly, the binding molecule of the invention may consist of the variable domains of the TCR alpha and beta chains, optionally with additional domains as described herein. Additional domains include but are not limited to immune effector domains (such as antibody domains), Fc domains or albumin binding domains, therapeutic agents or detectable labels.

The binding molecule may comprise the TCR alpha and beta chain variable domains in a single chain format. Single chain formats include, but are not limited to, as TCR polypeptides of the Vα-L-Vβ, Vβ-L-Vα, Vα-Ca-L-Vβ, Vα-L-Vβ-Cβ, or Vα-Cα-L-Vβ-Cβ types, wherein Vα and Vβ are TCR α and β variable domains respectively, Cα and Cβ are TCR α and β constant domains respectively, and L is a linker sequence (Weidanz et al., (1998) J Immunol Methods. December 1; 221 (1-2):59-76; Epel et al., (2002), Cancer Immunol Immunother. November; 51(10):565-73; WO 2004/033685; WO9918129).

The term "linker" as used herein refers to one or more amino acid residues inserted between domains, or a domain and an agent, to provide sufficient mobility for the domains or elements, for example the domains of the binding molecules of the invention to fold correctly to form the antigen binding sites. A linker may be inserted at the transition between variable domains or between variable domains and constant domains (or other domains), respectively, at the amino acid sequence level. The transition between domains can be identified because the approximate size of antibody domains as well as TCR domains is well understood by those skilled in the art. The precise location of a domain transition can be determined by locating peptide stretches that do not form secondary structural elements such as beta-sheets or alpha-helices as demonstrated by experimental data or as can be assumed by techniques of modeling or secondary structure prediction.

Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length, The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used in binding molecules of the invention include, but are not limited to: GGGGS (SEQ ID NO: 72), GGGSG (SEQ ID NO: 78), GGSGG (SEQ ID NO: 79), GSGGG (SEQ ID NO: 80), GSGGGP (SEQ ID NO: 81), GGEPS (SEQ ID NO: 82), GGEGGGP (SEQ ID NO: 83), GGEGGGSEGGGS (SEQ ID NO: 84), GGGSGGGG (SEQ ID NO: 85), GGGGSGGGGSGGGGSGGGGSGGGS (SEQ ID NO: 86), GGGGSGGGGSGGGGSGGGGS (SEQ ID NO: 87), EAAAK (SEQ ID NO: 88) and EAAAKEAAAKEAAAK (SEQ ID NO: 89). Where present, one or both of the constant domains may be full length, or they may be truncated and/or contain mutations as described above. Single chain TCRs may be soluble, i.e., they do not comprise a transmembrane domain. In certain embodiments single chain TCRs of the invention may have an introduced disulphide bond between residues of the respective constant domains, as described in WO 2004/033685. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

Alternatively the binding molecule may comprise two or more polypeptide chains, wherein the TCR alpha chain variable domain and the TCR beta chain variable domain are comprised in separate polypeptide chains.

The TCR variable domains may be arranged in diabody format. In the diabody format two single chain fragments dimerize in a head-to-tail orientation resulting in a compact molecule with a molecular mass similar to tandem scFv (~50 kDa).

Particularly suitable TCR alpha chain sequences include, but are not limited to, any one of SEQ ID NOs: 2, 49, 51, 54, 56, and 58. Particularly suitable TCR beta chain sequences include, but are not limited to, any one of SEQ ID NOs: 12, 50, 52, 53, 55, 57 and 59. Such sequences do not comprise transmembrane or cytoplasmic domains. It is expected that every alpha chain sequence (i.e., SEQ ID NOs: 2, 49, 51, 54, 56 and 58) is compatible with every beta chain sequence (i.e., SEQ ID NOs: 12, 50, 52, 53, 55, 57 and 59), as they are all derived from the same native (scaffold) TCR sequences (SEQ ID NOs: 2 and 12 respectively). Thus, the binding molecule of the invention may comprise a TCR alpha chain comprising an amino acid sequence as set forth in any one of SEQ ID NOs: 2, 49, 51, 54, 56 and 58, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in any one of SEQ ID NOs: 2, 49, 51, 54, 56 and 58, and a TCR beta chain comprising an amino acid sequence as set forth in any one of SEQ ID NOs: 12, 50, 52, 53, 55, 57 and 59, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in any one of SEQ ID NOs: 12, 50, 52, 53, 55, 57 and 59.

More specifically, the binding molecule may comprise (a) a TCR alpha chain comprising the amino acid sequence of SEQ ID NO: 49 and a TCR beta chain comprising the amino acid sequence of SEQ ID NO: 50;

(b) a TCR alpha chain comprising the amino acid sequence of SEQ ID NO: 51 and a TCR beta chain comprising the amino acid sequence of SEQ ID NO: 52;

(c) a TCR alpha chain comprising the amino acid sequence of SEQ ID NO: 49 and a TCR beta chain comprising the amino acid sequence of SEQ ID NO: 53;

(d) a TCR alpha chain comprising the amino acid sequence of SEQ ID NO: 54 and a TCR beta chain comprising the amino acid sequence of SEQ ID NO: 55;

(e) a TCR alpha chain comprising the amino acid sequence of SEQ ID NO: 56 and a TCR beta chain comprising the amino acid sequence of SEQ ID NO: 57; or (f) a TCR alpha chain comprising the amino acid sequence of SEQ ID NO: 58 and a TCR beta chain comprising the amino acid sequence of SEQ ID NO: 59.

Preferably, the binding molecule comprises a TCR alpha chain comprising the amino acid sequence of SEQ ID NO: 58 and a TCR beta chain comprising the amino acid sequence of SEQ ID NO: 59. In this regard, the invention provides a binding molecule having the property of binding to SLSNRLYYL (SEQ ID NO: 1) in complex with HLA-A*02, wherein the binding molecule comprises a TCR alpha chain comprising the amino acid sequence of SEQ ID NO: 58, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence of SEQ ID NO: 58, and a TCR beta chain comprising the amino acid sequence of SEQ ID NO: 59, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence of SEQ ID NO: 59.

Binding molecules of the invention are useful for delivering detectable labels or therapeutic agents to antigen presenting cells and tissues containing antigen presenting cells. They may therefore comprise or be associated (covalently or otherwise) with a detectable label (for diagnostic purposes wherein the binding molecule is used to detect the presence of cells presenting the cognate antigen); and or a therapeutic agent, including immune effectors; and or a pharmacokinetics (PK) modifying moiety.

Examples of PK modifying moieties include, but are not limited to, PEG (Dozier et al., (2015) Int J Mol Sci. October 28; 16(10):25831-64 and Jevsevar et al., (2010) Biotechnol J. January; 5(1):113-28), PASylation (Schlapschy et al., (2013) Protein Eng Des Sel. August; 26(8):489-501), albumin, and albumin binding domains, (Dennis et al., (2002) J Biol Chem. Sep. 20; 277(38):35035-43), and/or unstructured polypeptides (Schellenberger et al., (2009) Nat Biotechnol. December; 27(12):1186-90). Further PK modifying moieties include immunoglobulin Fc regions. PK modifying moieties may serve to extend the in vivo half-life of binding molecules of the invention.

Where an immunoglobulin Fc region is used, it may be any antibody Fc region. The Fc region is the tail portion of an antibody that interacts with cell surface Fc receptors and some proteins of the complement system. The Fc region typically comprises two polypeptide chains both having two or three heavy chain constant domains (termed CH2, CH3 and CH4), and a hinge region, the two chains being linked by disulphide bonds within the hinge region. Fc regions from immunoglobulin subclasses IgG1, IgG2 and IgG4 bind to and undergo FcRn mediated recycling, affording a long circulatory half-life (3-4 weeks). The interaction of IgG with FcRn has been localized in the Fc region covering parts of the CH2 and CH3 domain. Particularly suitable immunoglobulin Fc for use in the present invention include but are not limited to Fc regions from IgG1 or IgG4. The Fc region may be derived from human sequences.

A first Fc domain may comprise, or consist of, an amino acid sequence that is at least 80% identical to the sequence of SEQ ID NO: 95 and a second Fc domain may comprise, or consist of, an amino acid sequence that is at least 80% identical to the sequence of SEQ ID NO: 96. The first Fc domain may comprise, or consist of, an amino acid sequence that is at least 90%, at least 95%, or at least 98% identical to the sequence of SEQ ID NO: 95 and the domain Fc region may comprise, or consist of, an amino acid sequence that is at least 90%, at least 95%, or at least 98% identical to the sequence of SEQ ID NO: 96. Preferably, the first Fc domain comprises, or consists of, the amino acid sequence provided in SEQ ID NO: 95 and the second Fc domain comprises, or consists of, the amino acid sequence provided in SEQ ID NO: 96. As the skilled person would appreciate, the sequences provided above for the first and second Fc domains are suitable vice versa. For example, the first Fc domain may comprise, or consist of, the amino acid sequence provided in SEQ ID NO: 96 and the second Fc domain may comprise, or consist of, the amino acid sequence provided in SEQ ID NO: 95.

The Fc region may also preferably include KiH mutations which facilitate dimerization, as well as mutations to prevent interaction with activating receptors i.e. functionally silent molecules. The immunoglobulin Fc region may be fused to the C or N terminus of the other domains (i.e., the TCR variable domains and/or TCR constant domains and/or immune effector domains), in any suitable order or configuration. The immunoglobulin Fc may be fused to one or more of the other domains (i.e., the TCR variable domains and/or TCR constant domains and/or an immune effector domains) via a linker. Suitable linker sequences are known in the art and include those described herein. Where the immunoglobulin Fc is fused to the TCR, it may be fused to either the alpha or beta chains, with or without a linker. Furthermore, individual chains of the Fc may be fused to individual chains of the TCR.

The Fc region, if present, may comprise mutations relative to a wild-type or unmodified Fc sequence. Mutations include substitutions, insertions and deletions. Such mutations may be made for the purpose of introducing desirable therapeutic properties. The Fc region may comprise one or more amino acid substitutions which facilitate dimerisation of the respective Fc domains. For example, to facilitate heterodimerisation, knobs into holes (KiH) mutations maybe engineered into the CH3 domain. In this case, one chain is engineered to contain a bulky protruding residue (i.e. the knob), such as Y, and the other is chain engineered to contain a complementary pocket (i.e. the hole). Without wishing to be bound to theory, this is thought to stabilize a hetero-dimer of the respective Fc domains by favouring formation of the hetero-dimer over other species, for example homomultimers, thereby enhancing the stability and manufacturability Suitable positions for KiH mutations, and other mutations for facilitating dimerisation of Fc domains, are known in the art and include those described in Merchant et al., Nat Biotechnol 16:677 (1998) and Ridgway et al., Prot Engineering 9:617 (1996) and Atwell et al. J Mol Biol 270,1 (1997): 26-35. For example, the substitutions forming corresponding knobs and holes in two Fc domains may correspond to one or more pairs provided in the following table:

| CH3 of one of the first and second Fc domains | CH3 of the other of the first and second Fc domains |
| --- | --- |
| T366Y | Y407T |
| T366W | Y407A |
| T366W | T366S:L368A:Y407V |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

The substitutions in the table above are denoted by the original residue, followed by the position using the EU numbering system, and then the import residue (all residues are given in single-letter amino acid code). Multiple substitutions are separated by a colon.

The first and second Fc domains may comprise one or more substitutions in the table above. For example:
(i) one of the first Fc domain and the second Fc domain may comprise one or more amino acid substitutions selected from the group consisting of T366S, L368A, T394S, F405A, Y407A, Y407T and Y407V, according to the EU numbering scheme; and
(ii) the other of the first Fc domain and the second Fc domain may comprise one or more amino acid substitutions selected from the group consisting of T366W, T366Y, T366W, T394W and F405W according to the EU numbering scheme. The substitutions in (i) and (ii) are hole-forming and knob-forming substitutions respectively. The first Fc domain may comprise one or more of the substitutions in (i) and the second Fc domain may comprise one or more of the substitutions in (ii).

For example:
(i) one of the first Fc domain and the second Fc domain may comprise one or more amino acid substitutions selected from the group consisting of T366S, L368A, and Y407V, according to the EU numbering scheme; and (ii) the other of the first Fc domain and the second Fc domain may comprise a T366W amino acid substitution, according to the EU numbering scheme. The first Fc domain may comprise one or more of the substitutions in (i) and the second Fc domain may comprise the substitution in (ii).

Preferably, (i) one of the first and second Fc domains comprises T366S, L368A, and Y407V amino acid substitutions, according to the EU numbering scheme; and (ii) the other of the first and second Fc domains comprises a T366W amino acid substitution, according to the EU numbering scheme. For example, the first Fc domain may comprise T366S, L368A, and Y407V amino acid substitutions, according to the EU numbering scheme; and the second Fc domain may comprise a T366W amino acid substitution, according to the EU numbering scheme.

Additionally or alternatively mutations may be introduced that abrogate or reduce binding to Fcγ receptors and or increase binding to FcRn, and/or prevent Fab arm exchange, or remove protease sites. Additionally, or alternatively, mutations improve manufacturability for example to remove or alter glycosylation sites.

The Fc region may also comprise one or more mutations that attenuate an effector function of the Fc region. Exemplary effector functions include, without limitation, complement-dependent cytotoxicity (CDC) and/or antibody-dependent cellular cytotoxicity (ADCC). The modification to attenuate effector function may be a modification that alters the glycosylation pattern of the Fc region, e.g. a modification that results in an aglycosylated Fc region. Alternatively, the modification to attenuate effector function may be a modification that does not alter the glycosylation pattern of the Fc region. The modification to attenuate effector function may reduce or eliminate binding to human effector cells, binding to one or more Fc receptors, and/or binding to cells expressing an Fc receptor. For example, the Fc domain may comprise one or more amino acid substitutions selected from the group consisting of S228P, E233P, L234A, L235A, L235E, L235P, G236R, G237A, P238S, F241A, V264A D265A, H268A, D270A, N297A, N297G, N297Q, E318A, K322A, L328R, P329G, P329A, A330S, A330L, P331A and P331S, according to the EU numbering scheme. Particular modifications include a N297G or N297A substitution in the Fc region of human IgG1 (EU numbering). Other suitable modifications include L234A, L235A and P329G substitutions in the Fc region of human IgG1 (EU numbering), that result in attenuated effector function. The Fc domain may comprise a substitution at residue N297, numbering according to EU index. For example, the substitution may be an N297G or N297A substitution. Other suitable mutations (e.g., at residue N297) are known to those skilled in the art.

Fc variants having reduced effector function refers to Fc variants that reduce effector function (e.g., CDC, ADCC, and/or binding to FcR, etc. activities) by at least 10%, 20%, 30%, 40%, 50%, 60%, 70%, 80%, 90%, 95%, 97%, 98%, 99% or more as compared to the effector function achieved by a wild-type Fc region (e.g., an Fc region not having a mutation to reduce effector function, although it may have other mutations). The Fc variants having reduced effector function may be Fc variants that eliminate all detectable effector function as compared to a wild-type Fc region. Assays for measuring effector function are known in the art and described below. In vitro and/or in vivo cytotoxicity assays can be conducted to confirm the reduction/depletion of CDC and/or ADCC activities. For example, Fc receptor (FcR) binding assays can be conducted to ensure that the Fc region, domain or fusion protein lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)).

Substitutions may be introduced into the first and second Fc domains that abrogate or reduce binding to Fcγ receptors and/or to increase binding to FcRn, and/or prevent Fab arm exchange, and/or remove protease sites. In this regard, the or each Fc region may also comprise one or more amino acid substitutions which prevent or reduce binding to activating receptors. The half-life extending domain may comprise one or more amino acid substitutions which prevent or reduce binding to FcγR. For example, the first Fc domain and/or the second Fc domain may comprise a N297G amino acid substitution, according to the EU numbering scheme. Both the first and second Fc domain may comprise the N297G amino acid substitution.

The or each Fc domain may comprise one or more amino acid substitutions which promote binding to FcRn. Methods of measuring binding to FcRn are known (see, e.g., Ghetie and Ward, Immunol. Today 18: (12): 592-8 (1997); Ghetie et al., Nature Biotechnology 15 (7): 637-40 (1997); Hinton et al., J. Biol. Chem. 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody substitutions which improved or diminished binding to FcRs. See also, e.g., Shields et al., J. Biol. Chem. 9(2): 6591-6604 (2001). In particular, Mackness et al., MAbs. 11:1276-1288 (2019) describes suitable amino acid substitutions in antibody Fc regions for enhancing binding to FcRn.

Additionally or alternatively, mutations may be made for manufacturing reasons, for example to remove or replace amino acids that may be subject to post-translational modifications such as glycosylation, as described herein. The immunoglobulin Fc may be fused to the other domains in the molecule of the invention via a linker, and/or a hinge sequence as described herein. Alternatively no linker may be used.

Where present, the two Fc domains in the molecule of the invention may comprise CH2 and CH3 constant domains and all or part of a hinge sequence. The hinge sequence may correspond substantially or partially to a hinge region from IgG1, IgG2, IgG3 or IgG4. The hinge sequence may be an IgG1 hinge sequence, such as the amino acid sequence provided in SEQ ID NO: 94. The hinge may comprise all or part of a core hinge domain and all or part of a lower hinge region. The PK modifying moiety may also be albumin or an albumin-binding domain, which may also act to extend half-life. As is known in the art, albumin has a long circulatory half-life of 19 days, due in part to its size, being above the renal threshold, and by its specific interaction and recycling via FcRn. Attachment to albumin is a well-known strategy to improve the circulatory half-life of a therapeutic molecule in vivo. Albumin may be attached non-covalently, through the use of a specific albumin binding domain, or covalently, by conjugation or direct genetic fusion. Examples of therapeutic molecules that have exploited attachment to albumin for improved half-life are given in Sleep et al., Biochim Biophys Acta. 2013 December; 1830 (12):5526-34.

The albumin-binding domain may be any moiety capable of binding to albumin, including any known albumin-binding moiety. Albumin binding domains may be selected from endogenous or exogenous ligands, small organic molecules, fatty acids, peptides and proteins that specifically bind albumin. Examples of preferred albumin binding domains include short peptides, such as described in Dennis et al., J Biol Chem. 2002 Sep. 20; 277(38):35035-43 (for example the peptide QRLMEDICLPRWGCLWEDDF); proteins engineered to bind albumin such as antibodies, antibody fragments and antibody like scaffolds, for example Albudab® (O'Connor-Semmes et al., Clin Pharmacol Ther. 2014 December; 96(6):704-12), commercially provided by GSK and Nanobody® (Van Roy et al., Arthritis Res Ther. 2015 May 20; 17:135), commercially provided by Ablynx; and proteins based on albumin binding domains found in nature such as Streptococcal protein G Protein (Stork et al., Eng Des Sel. 2007 November; 20(11):569-76), for example Albumod® commercially provided by Affibody. Preferably, albumin is human serum albumin (HSA). The affinity of the albumin binding domain for human albumin may be in the range of picomolar to micromolar. Given the extremely high concentration of albumin in human serum (35-50 mg/ml, approximately 0.6 mM), it is calculated that substantially all of the albumin binding domains will be bound to albumin in vivo.

The albumin-binding moiety may be fused to the C or N terminus of the other domains (i.e., the TCR variable domains and/or TCR constant domains and/or an immune effector domain), in any suitable order or configuration. The albumin-binding moiety may be fused to one or more of the other domains (i.e., the TCR variable domains and/or TCR constant domains and/or an immune effector domain) via a linker. Suitable linkers are known in the art and include those described herein. Where the albumin-binding moiety is linked to the TCR, it may be linked to either the alpha or beta chains, with or without a linker.

Detectable labels for diagnostic purposes include for instance, fluorescent labels, radiolabels, enzymes, nucleic acid probes and contrast reagents.

For some purposes, the binding molecules of the invention may be aggregated into a complex comprising several binding molecules to form a multivalent binding molecule complex. There are a number of human proteins that contain a multimerisation domain that may be used in the production of multivalent binding molecule complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent binding molecule complex of the invention may have enhanced binding capability for the complex compared to a non-multimeric native (also referred to as parental, natural, unmutated wild type, or scaffold) T cell receptor heterodimer of the invention. Thus, multivalent complexes of binding molecules of the invention are also included within the invention. Such multivalent binding molecule complexes according to the invention are particularly useful for tracking or targeting cells presenting particular antigens in vitro or in vivo, and are also useful as intermediates for the production of further multivalent binding molecule complexes having such uses.

Therapeutic agents which may be associated with or comprised in the binding molecules of the invention include immune-modulators and effectors, radioactive compounds, enzymes (perforin for example) or chemotherapeutic agents (cis-platin for example). To ensure that the therapeutic effects are exercised in the desired location the agent could be inside a liposome or other nanoparticle structure linked to the binding molecule so that the compound is released slowly. This will prevent damaging effects during the transport in the body and ensure that the agent has maximum effect after binding of the binding molecule to the relevant antigen presenting cells.

Examples of suitable therapeutic agents include, but are not limited to:

antibodies, or fragments thereof, including anti-T cell or NK cell determinant antibodies (e.g. anti-CD3, anti-CD28 or anti-CD16)

alternative protein scaffolds with antibody-like binding characteristics (e.g. DARPins)

immuno-stimulants, i.e. immune effector molecules which stimulate immune response. For example, cytokines such as IL-2 and IFN-γ, chemokines such as IL-8, platelet factor 4, melanoma growth stimulatory protein, etc.

activators of the complement pathway or Fc receptors checkpoint inhibitors, such as those that target PD1 or PD-L1 small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate arbourate, auristatin E vincristine and doxorubicin peptide cytotoxins, i.e. proteins or fragments thereof with the ability to kill mammalian cells. For example, ricin, diphtheria toxin, pseudomonas bacterial exotoxin A, Dnase and Rnase;

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to TCRs, or multimers thereof;

superantigens and mutants thereof;

xenogeneic protein domains, allogeneic protein domains, viral/bacterial protein domains, viral/bacterial peptides Binding molecules of the invention may be multispecific. As used herein, the term "multispecific" refers to a binding molecule comprising two or more antigen binding moieties, including the TCR antigen binding moiety formed by the TCR alpha and beta chain variable domains. Such binding molecules are able to bind to the SLSNRLYYL (SEQ ID NO: 1)-HLA-A*02 complex and a further one or more different antigens. For example, the binding molecule may be bispecific. Such binding molecules comprise a TCR antigen binding moiety (formed by the alpha and beta chain variable domains) that binds to the SLSNRLYYL (SEQ ID NO: 1)-HLA-A*02 complex and one other antigen binding moiety (e.g., an antibody antigen binding moiety) that binds to a different antigen. This other antigen binding moiety may be referred to herein as the "second antigen binding moiety" and the antigen bound by the second antigen binding moiety may be referred to herein as the "second antigen". The second antigen binding moiety may be an immune cell engager. The term "antigen binding moiety" refers to a protein or region or domain thereof that is capable of binding to an antigen. For example, this term encompasses antigen binding sites of antibodies, including antigen binding sites from conventional and engineered antibodies.

A multispecific binding molecule may comprise an antigen-binding moiety of an antibody that is capable of binding to an antigen (i.e., the second antigen). In this regard, the binding molecule may comprise an antibody or a functional fragment or variant thereof. The term "antibody" as used herein is meant to include conventional/native antibodies and engineered antibodies, in particular functional antibody fragments, single chain antibodies, single domain antibodies, bispecific or multispecific antibodies. "Native" or "conventional" refers to an antibody that has the same type of domains and domain arrangements as an antibody found in nature and comprises antibody-derived CDR and FR sequences. In a native/conventional antibody, two heavy chains are linked to each other by disulfide bonds and each heavy chain is linked to a light chain by a disulfide bond. The variable domains of both light (VL) and heavy (VH) chains determine binding recognition and specificity to the antigen. Conventional antibody binding sites are made up of residues that are primarily from the "antibody complementarity determining regions" (CDRs) or hypervariable regions. Occasionally, residues from non-hypervariable or framework regions (FR) influence the overall domain structure and hence the binding site. CDRs refer to amino acid sequences that together define the binding affinity and specificity of the natural Fv region of a native antibody binding site. The light and heavy chains of a conventional antibody each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a VH and VL.

"Engineered" antibody formats include functional antibody fragments, single chain antibodies, single domain antibodies, and chimeric, humanized, bispecific or multispecific antibodies. Engineered antibody formats further include constructs in which TCR-derived CDRs, possibly including additional 3, 2 or 1 N and/or C terminal framework residues, or entire TCR-derived variable domains are grafted onto antibody heavy or light chains. A "functional antibody fragment" refers to a portion of a full-length antibody, or a protein that resembles a portion of a full-length antibody, that retains the ability to bind to its target antigen, in particular the antigen binding region or variable region of the full-length antibody. Examples of functional antibody "fragments" include Fv, Fab, F(ab')2, Fab', dsFv, (dsFv)2, scFv, sc(Fv)2 and diabodies. For example, a binding molecule of the invention may comprise a scFv. A functional antibody fragment may also be a single domain antibody, such as a heavy chain antibody. Thus, the binding molecule may comprise a VHH, for example. As is known in the art, the antigen binding site of a single domain antibody, such as a VHH, may comprise three CDRs (as opposed to six in a conventional antibody). The term "antigen binding moiety of an antibody", as used herein, encompasses such binding sites. Alternatively, or additionally, the binding molecule may comprise a Fab or Fv fragment. The term "Fab" denotes an antibody fragment having a molecular weight of about 50,000 Dalton and antigen binding activity, in which about a half of the N-terminal side of H chain and the entire L chain, among fragments obtained by treating IgG with a protease, e.g. papain, are bound together through a disulfide bond. The Fv fragment is the N-terminal part of the Fab fragment of an antibody and consists of the variable portions of one light chain and one heavy chain.

Binding molecules comprising antibody antigen-binding moieties, as described above, may be referred to as bispecific TCR-antibody molecules, i.e. binding molecules which comprise at least two antigen binding moieties, wherein one is derived from an antibody and the other is derived from a TCR. Such binding molecules may comprise an antibody heavy chain variable domain (VH) and an antibody light chain variable domain (VL), which associate to form the antibody antigen-binding moiety that is capable of binding to an antigen. Thus, the antigen binding moiety may comprise the VH and the VL. For example, the binding molecule may comprise a scFv comprising the VH and VL. Alternatively, the antigen binding moiety of the antibody may comprise a single variable domain (e.g., a VHH).

In such bispecific TCR-antibody molecules, the variable domains may be arranged e.g. as described for the different bispecific antibody formats discussed above. Techniques to produce such bispecific molecules are also disclosed in the above cited prior art and those skilled in the art can thus easily use the CDRs or the variable domains as herein defined to generate and produce the antigen binding proteins of the invention in the herein disclosed formats. In addition, further formats are possible, e.g. formats in which on each chain, the variable domains are separated by a constant domain that mediates dimerization, such that in the final molecule the two antigen binding sites are located on two sides of the dimerized constant domains. The skilled person is entirely capable of selecting suitable linkers to ensure folding in the desired conformation.

The second antigen binding moiety (e.g., an antibody antigen binding moiety comprising a VH and VL) may bind to an antigen of an effector cell. Such a binding molecule may be referred to as a "recruiter", as it recruits an effector cell to a tumour. In the context of the present invention, "effector cell" refers to a T cell or natural killer cell (NK cell). The second antigen binding moiety may be an immune cell engager. In particular, the antigen (i.e., the second antigen) may be a T cell surface antigen.

The antigen may be selected from the group consisting of CD2, CD3 (such as the CD3γ, CD3δ, and CD3ε chains), CD4, CD5, CD7, CD8, CD10, CD11b, CD11c, CD14, CD16, CD18, CD22, CD25, CD28, CD32a, CD32b, CD33, CD41, CD41 b, CD42a, CD42b, CD44, CD45RA, CD49, CD55, CD56, CD61, CD64, CD68, CD90, CD94, CD95, CD117, CD123, CD125, CD134, CD137, CD152, CD163, CD193, CD203c, CD235a, CD278, CD279, CD287, Nkp46, NKG2D, GITR, FCεRI, TCRα/β, TCRγ/δ, HLA-DR and 4-1 BB, or combinations thereof. "Combinations thereof" refers to complexes of two or more of said antigens, e.g. a TCRα/β CD3 complex. Preferably, the antigen is CD3.

Suitable antigen binding moieties for binding to CD3 include binding domains derived from the CD3-specific, humanized antibody hUCHU (Zhu et al., Identification of heavy chain residues in a humanized anti-CD3 antibody important for efficient antigen binding and T cell activation. J Immunol, 1995, 155, 1903-1910). In particular VH and VL domains derived from the UCHT1 variants UCHT1-V17, UCHT1-V17opt, UCHT1-V21 or UCHT1-V23 may be used. Alternatively, VH and VL domains derived from the antibody BMA031, which targets the TCRα/β CD3 complex, and humanized versions thereof (Shearman et al., Construction, expression and characterization of humanized antibodies directed against the human alpha/beta T cell receptor, J Immunol, 1991, 147, 4366-73) may be used, in particular VH and VL domains derived from BMA031 variants BMA031 (V36) or BMA031(V10). Suitable BMA031 antibody variant sequences are described in WO 2022/233957. As another alternative, VH and VL domains derived from the CD3-specific antibody H2C (described in EP 2155783) may be used.

Other suitable CD3-binding moieties may be derived from the anti-CD3 scFv referred to herein as "U0" (SEQ ID NO: 60) or "U28" (SEQ ID NO: 70). For example, the binding molecule may comprise an antibody antigen-binding moiety comprising a VH and a VL and which is capable of binding to CD3, wherein
(a) the VH comprises CDRs having the following sequences:

```
CDR1 -
                              (SEQ ID NO: 66)
GYSFTGYT
or
                              (SEQ ID NO: 71)
GYSFTGYA;
CDR2 -
                              (SEQ ID NO: 67)
INPYKGVS;
and
CDR3 -
                              (SEQ ID NO: 68)
ARSGYYGDSDWYFDV,
``` and
(b) the VL comprises CDRs having the following sequences:

```
CDR1 -
                              (SEQ ID NO: 62)
QDIRNY;
CDR2 -
YTS;
and
CDR3 -
                              (SEQ ID NO: 64)
QQGNTLPWT.
```

The binding molecule may comprise an antibody antigen-binding moiety comprising a VH and a VL and which is capable of binding to CD3, wherein
the VH comprises an amino acid sequence as set forth in SEQ ID NO: 65 or 69, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in SEQ ID NO: 65 or 69; and the VL comprises an amino acid sequence as set forth in SEQ ID NO: 61, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in SEQ ID NO: 61.

The binding molecule may comprise a scFv that is capable of binding to CD3. The scFv may preferably comprise a VH comprising the amino acid sequence as set forth in SEQ ID NO: 69, and a VL comprising the amino acid sequence as set forth in SEQ ID NO: 61. Such an scFv may comprise the amino acid sequence provided in SEQ ID NO: 70.

Alternatively, the scFv may comprise a VH comprising the amino acid sequence as set forth in SEQ ID NO: 65, and a VL comprising the amino acid sequence as set forth in SEQ ID NO: 61. Such an scFv may comprise the amino acid sequence provided in SEQ ID NO: 60.

For binding molecules comprising an antibody antigen-binding moiety, the VH or VL may be covalently linked to the C- or N-terminus of the TCR alpha chain or TCR beta chain, optionally via a linker sequence. Suitable linker sequences are known in the art. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. For example, the VH or VL may be covalently linked to the C- or N-terminus of the TCR alpha chain or TCR beta chain via a linker sequence selected from GGGGS (SEQ ID NO: 72), GGGSG (SEQ ID NO: 78), GGSGG (SEQ ID NO: 79), GSGGG (SEQ ID NO: 80), GSGGGP (SEQ ID NO: 81), GGEPS (SEQ ID NO: 82), GGEGGGP (SEQ ID NO: 83), GGEGGGSEGGGS (SEQ ID NO: 84), GGGSGGGG (SEQ ID NO: 85), GGGGSGGGGSGGGGSGGGGSGGGS (SEQ ID NO: 86), GGGGSGGGGSGGGGSGGGGS (SEQ ID NO: 87), EAAAK (SEQ ID NO: 88) and EAAAKEAAAKEAAAK (SEQ ID NO: 89).

For binding molecules comprising an antigen binding moiety of an antibody, preferably the C-terminus of the VH is covalently linked to the N-terminus of the TCR beta chain, optionally via a linker comprising the amino acid sequence provided in SEQ ID NO: 72. Preferably, such a binding molecule comprises a first polypeptide chain and a second polypeptide chain, wherein:

the first polypeptide chain comprises a TCR alpha chain (the alpha chain itself comprising a variable domain and optionally the extracellular region of a constant domain), and the second polypeptide chain (also referred to herein as a "beta chain-anti-CD3" chain) comprises a TCR beta chain (the beta chain itself comprising a variable domain and optionally the extracellular region of a constant domain) and an scFv comprising a VH and a VL, wherein the C-terminus of the VH is covalently linked to the N-terminus of the TCR beta chain, optionally via a linker comprising the amino acid sequence provided in SEQ ID NO: 72.

Binding molecules in the format described above include ImmTAC® molecules. Examples of such molecules include tebentafusp, which is sold under the brand name KIMMTRAK® as well as the binding molecules described in WO2010133828, WO2019012138 and WO2019012141, for example. Exemplary binding molecules of the invention in this format include a40b23U28 (consisting of SEQ ID NOs: 49 and 119), a36b38U28 (consisting of SEQ ID NOs: 51 and 73), a40b37U28 (consisting of SEQ ID NOs: 49 and 74), a58b63U28 (consisting of SEQ ID NOs: 54 and 75), a61b68U28 (consisting of SEQ ID NOs: 56 and 76) and a67b72U28 (consisting of SEQ ID NOs: 58 and 77).

A binding molecule in the format described above may comprise an alpha chain amino acid sequence as set forth in any one of SEQ ID NOs: 49, 51, 54, 56 and 58, or an alpha chain amino acid sequence that has at least 90% identity, such as at least 90%, at least 91%, at least 92%, at least 93%, at least 94%, at least 95%, at least 96%, at least 97%, at least 98%, at least 99% or 100% identity, to the amino acid sequences as set forth in any one of SEQ ID NOs: 49, 51, 54, 56 and 58, and a beta chain-anti-CD3 amino acid sequence as set forth in any one of SEQ ID NOs: 119, 73, 74, 75, 76 and 77, or a beta chain amino acid sequence that has at least 90% identity, such as at least 90%, at least 91%, at least 92%, at least 93%, at least 94%, at least 95%, at least 96%, at least 97%, at least 98%, at least 99% or 100% identity, to the amino acid sequences as set forth in any one of SEQ ID NOs: 119, 73, 74, 75, 76 and 77.

More particularly, a binding molecule in the format described above may comprise
(a) an alpha chain amino acid sequence as set forth in SEQ ID NO: 49 and a beta chain-anti-CD3 amino acid sequence as set forth in SEQ ID NO: 119;
(b) an alpha chain amino acid sequence as set forth in SEQ ID NO: 51 and a beta chain-anti-CD3 amino acid sequence as set forth in SEQ ID NO: 73;
I an alpha chain amino acid sequence as set forth in SEQ ID NO: 49 and a beta chain-anti-CD3 amino acid sequence as set forth in SEQ ID NO: 74;
(d) an alpha chain amino acid sequence as set forth in SEQ ID NO: 54 and a beta chain-anti-CD3 amino acid sequence as set forth in SEQ ID NO: 75;
(e) an alpha chain amino acid sequence as set forth in SEQ ID NO: 56 and a beta chain-anti-CD3 amino acid sequence as set forth in SEQ ID NO: 76; or
(f) an alpha chain amino acid sequence as set forth in SEQ ID NO: 58 and a beta chain-anti-CD3 amino acid sequence as set forth in SEQ ID NO: 77.

Preferably, the binding molecule comprises an alpha chain amino acid sequence as set forth in SEQ ID NO: 58 and a beta chain-anti-CD3 amino acid sequence as set forth in SEQ ID NO: 77. Thus, the invention provides a binding molecule having the property of binding to SLSNRLYYL (SEQ ID NO: 1) in complex with HLA-A*02, wherein the binding molecule comprises a TCR alpha chain and a TCR beta chain covalently linked to an anti-CD3 scFv, wherein the alpha chain comprises the amino acid sequence set forth in SEQ ID NO: 58 and the beta chain-antiCD3 chain comprises the amino acid sequence set forth in SEQ ID NO: 77.

The binding molecules may be bispecific T cell engaging receptors (TCER®) which are soluble Fc-containing bispecific antigen binding molecules comprising a TCR antigen binding moiety and an antibody antigen binding moiety. The antibody antigen binding moiety is formed by the heavy and light chain variable domains of an antibody. TCER®s comprise two polypeptide chains, wherein the antigen binding sites are formed by variable domains located on different polypeptide chains in a cross-over orientation. Thus, the binding molecule may comprise:

a first polypeptide chain which comprises the TCR alpha chain variable domain and the antibody VH or VL; and
a second polypeptide chain which comprises the TCR beta chain variable domain and the other of the antibody VH and VL,
wherein the respective polypeptide chains associate such that the binding molecule is capable of simultaneously binding the SLSNRLYYL (SEQ ID NO: 1) HLA-A*02 complex and the antigen of the antibody.

The binding molecules of the invention may be in the form of a multi-domain, single-chain binding molecule comprising:
  i) a peptide-major histocompatibility complex (pMHC) binding region comprising a first variable domain linked to a constant domain (VC1) and a second variable domain linked to a constant domain (VC2), wherein VC1 and VC2 dimerise to form the pMHC binding region;
  ii) an antigen binding region comprising an antibody light chain variable domain (VL) and an antibody heavy chain variable domain(VH); and
  iii) a half-life extending region comprising a first IgG Fc domain (FC1) and a second IgG Fc domain (FC2), wherein the FC1 domain and FC2 domain dimerise to form an Fc region;
  wherein the first variable domain comprises one of (a) the TCR alpha chain variable domain and (b) the TCR beta chain variable domain, and the second variable domain comprises the other of (a) the TCR alpha chain variable domain and (b) the TCR beta chain variable domain,
  the antigen binding region is linked to the N terminus of VC1, VC1 is linked via its C terminus to the N terminus of the FC1 domain, the FC1 domain is linked via its C terminus to the N terminus of VC2, and VC2 is linked via its C terminus to the N terminus of the FC2 domain; and
  the pMHC binding region and the antigen binding region are capable of binding to the SLSNRLYYL (SEQ ID NO: 1) HLA-A*02 complex and the antigen of the antibody respectively.

The antigen binding region may be a T cell engaging immune effector, which may be an ScFv. The antigen binding region may be a CD3 effector that activates a T cell through interaction with CD3 and/or a TCR/CD3 complex. The T cell engaging immune effector may be an anti-CD3 scFv.

VC1 may comprise either (a) the TCRα variable domain and a TCRα constant domain or (b) the TCRβ variable domain and a TCRβ constant domain, and VC2 may comprise the other of (a) and (b). It is preferred if VC1 comprises the TCRβ variable and constant domain and VC2 comprises the TCRα variable and constant domain.

The VL domain may be linked via its C terminus to the N terminus of the VH domain and the VH domain may be linked via its C terminus to the N terminus of VC1.

Two or more of the VH, VL, VC1, VC2, FC1 and FC2 domains may be linked to each other via linkers and/or IgG hinge sequences. The linker or linkers may have a sequence as described herein.

VC1 may be linked to the FC1 domain via a sequence comprising an IgG hinge sequence and/or VC2 may be linked to the FC2 domain via a sequence comprising an IgG hinge sequence. The IgG hinge sequence is preferably at least 80% identical to SEQ ID NO: 94.

The binding molecules of the invention preferably comprise a protein. The binding molecule may be glycosylated, amidated, carboxylated, phosphorylated, esterified, N-acylated, cyclized via, e.g., a disulfide bridge, or converted into an acid addition salt and/or optionally dimerized or polymerized, or conjugated. All such forms are encompassed by the present invention.

The binding molecules may be synthetic, recombinant, isolated, engineered and/or purified. By "purified" it is meant, when referring to a polypeptide, or nucleotide sequence, that the indicated molecule is present in the substantial absence of other biological macromolecules of the same type.

The term "purified" as used herein means that at least 75%, 85%, 95%, or 98% by weight, of biological macromolecules of the same type are the indicated molecule. A purified nucleic acid molecule that encodes a particular polypeptide refers to a nucleic acid molecule that is substantially free of other nucleic acid molecules that do not encode the subject polypeptide; however, the molecule may include some additional bases or moieties, which do not deleteriously affect the basic characteristics of the composition.

The term "isolated" means altered or removed from the natural state. For example, a nucleic acid or a polypeptide naturally present in a living animal is not "isolated," but the same nucleic acid or peptide partially or completely separated from the coexisting materials of its natural state is "isolated". An isolated nucleic acid or protein can exist in substantially purified form, or can exist in a non-native environment such as, for example, a host cell. An isolated binding molecule is substantially free of other binding molecules having different antigenic specificities. Moreover, an isolated binding molecule may be substantially free of other cellular material and/or chemicals.

A "recombinant" molecule is one that has been prepared, expressed, created, or isolated by recombinant means. In this regard, recombinant molecules do not exist in nature.

Amino Acid Sequences

Within the scope of the invention are phenotypically silent variants of any molecule disclosed herein.

As used herein the term "phenotypically silent variants" is understood to refer to a variant which incorporates one or more further amino acid changes, including substitutions, insertions and deletions, in addition to those set out above, and which variant has a similar phenotype to the corresponding molecule without said change(s). For the purposes of this invention, phenotype comprises binding affinity ($K_D$ and/or binding half-life) and/or specificity. The phenotype for a soluble binding molecule may include potency of immune activation and purification yield, in addition to binding affinity and specificity. A phenotypically silent variant may have a $K_D$ and/or binding half-life for the SLSNRLYYL (SEQ ID NO: 1) HLA-A*02 complex within 50%, or more preferably within 30%, 25% or 20%, of the measured $K_D$ and/or binding half-life of the corresponding binding molecule without said change(s), when measured under identical conditions (for example at 25° C. and/or on the same SPR chip). Suitable conditions are further provided in the Examples.

Furthermore, a phenotypically silent variant may retain the same, or substantially the same, therapeutic window between binding to the SLSNRLYYL (SEQ ID NO: 1) HLA-A*02 complex and binding to one or more alternative peptide-HLA complexes. A phenotypically silent variant may retain the same, or substantially the same, therapeutic window between potency of immune cell activation in response to cells presenting to the SLSNRLYYL (SEQ ID NO: 1) HLA-A*02 complex and cells presenting one or more alternative off-target peptide-HLA complexes. The therapeutic window may be calculated based on lowest effective concentrations ("LOEL") observed for normal cells and the indication relevant cell line. The therapeutic window may be at least 10 fold different; at least 100 fold difference, at least 1000 fold difference, or more. A phenotypic variant may share the same, or substantially the same recognition motif as determined by sequential mutagenesis techniques discussed further below As is known to those skilled in the art, it may be possible to produce binding molecules that incorporate changes in the variable domains thereof compared to those detailed above without significantly altering the affinity of the interaction with the SLSNRLYYL (SEQ ID NO: 1) HLA-A*02 complex, and or other functional characteristics. In particular, such silent mutations may be incorporated within parts of the sequence that are known not to be directly involved in antigen binding (e.g. the framework regions and or parts of the CDRs that do not contact the antigen). Such variants are included in the scope of this invention.

Phenotypically silent variants may contain one or more conservative substitutions and/or one or more tolerated substitutions. By tolerated substitutions it is meant those substitutions which do not fall under the definition of conservative as provided below but are nonetheless phenotypically silent. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); cysteine and methionine (amino acids having sulphur containing side chains); and serine and threonine (amino acids having hydroxyl-containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

Substitutions of this nature are often referred to as "conservative" or "semi-conservative" amino acid substitutions. The present invention therefore extends to use of a molecule comprising any of the amino acid sequences described above but with one or more conservative substitutions and or one or more tolerated substitutions in the sequence, such that the amino acid sequence of the molecule, or any domain or region thereof, has at least 90% identity, such as 90%, 91%, 92%, 93%, 94%, 95%, 96%, 97%, 98%, 99% or 100% identity, to the sequences disclosed herein.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The BLASTn and BLASTp programs of Altschul, et al. (1990) J. Mol. Biol. 215:403-410 have incorporated such an algorithm. Determination of percent identity between two nucleotide sequences can be performed with the BLASTn program. Determination of percent identity between two protein sequences can be performed with the BLASTp program. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., BLASTp and BLASTp) can be used. See http://www.ncbi.nlm.nih.gov. Default general parameters may include for example, Word Size=3, Expect Threshold=10. Parameters may be selected to automatically adjust for short input sequences. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search. For the purposes of evaluating percent identity in the present disclosure, BLASTp with the default parameters is used as the comparison methodology. In addition, when the recited percent identity provides a non-whole number value for amino acids (i.e., a sequence of 25 amino acids having 90% sequence identity provides a value of "22.5", the obtained value is rounded down to the next whole number, thus "22"). Accordingly, in the example provided, a sequence having 22 matches out of 25 amino acids is within 90% sequence identity.

As used herein, where a sequence is referred to as having sequence identity to another sequence, that sequence retains the function, e.g. the general binding characteristics in the case of a peptide, of the other sequence.

As will be obvious to those skilled in the art, it may be possible to truncate, or extend, the sequences provided at the C-terminus and/or N-terminus thereof, by 1, 2, 3, 4, 5 or more residues, without substantially affecting the functional characteristics of the molecule, for example a TCR portion. The sequences provided at the C-terminus and/or N-terminus thereof may be truncated or extended by 1, 2, 3, 4 or 5 residues. All such variants are encompassed by the present invention.

Mutations, including conservative and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual ($3^{rd}$ Ed.) CSHL Press. Further information on ligation independent cloning (LIC) procedures can be found in Rashtchian, (1995) Curr Opin Biotechnol 6(1): 30-6. The protein sequences provided herein may be obtained from recombinant expression, solid state synthesis, or any other appropriate method known in the art.

Assessing Binding Characteristics and Activity of Binding Molecules

Methods to determine binding affinity (inversely proportional to the equilibrium constant $K_D$) and binding half-life (expressed as T1/2) are known to those skilled in the art. Binding affinity and binding half-life may be determined using Surface Plasmon Resonance (SPR) or Bio-Layer Interferometry (BLI), for example using a BIAcore instrument or Octet instrument, respectively. For example, binding affinity of a binding molecule for a peptide-HLA complex may be determined using SPR at 25° C., wherein the peptide-HLA complex is immobilised on a solid support (e.g., a sensor chip) and is contacted with a solution comprising the binding molecule. Suitable experimental conditions and methods for determining binding parameters are described in Examples 2 and 3.

It will be appreciated by those skilled in the art that a higher affinity refers to a lower numerical value for $K_D$ and indicates stronger binding In other words, a doubling of affinity refers to halving the numerical value of the $K_D$. T½ is calculated as ln2 divided by the off-rate ($k_{off}$). Therefore, doubling of T1/2 results in a halving in $k_{off}$. $K_D$ and $k_{off}$ values for TCRs are usually measured for soluble forms of the TCR, i.e. those forms which are truncated to remove cytoplasmic and transmembrane domain residues. To account for variation between independent measurements, and particularly for interactions with dissociation times in excess of 20 hours, the binding affinity and or binding half-life of a given protein may be measured several times, for example 3 or more times, using the same assay protocol, and an average of the results taken. To compare binding data between two samples (i.e. two different proteins and or two preparations of the same protein) it is preferable that measurements are made using the same assay conditions (e.g. temperature). Measurement methods described in relation to TCRs may also be applied to the binding molecules described herein.

Certain binding molecules of the invention are able to generate a highly potent T cell response in vitro against antigen positive cells, in particular those cells presenting low levels of antigen typical of cancer cells (i.e. in the order of 5-100, for example 50, antigens per cell (Bossi et al., (2013) Oncoimmunol. 1; 2 (11):e26840; Purbhoo et al., (2006). J Immunol 176(12): 7308-7316.). Such TCRs may be suitable for incorporation into the binding molecules described herein. The T cell response that is measured may be the release of T cell activation markers such as Interferon γ or Granzyme B, or target cell killing, or other measure of T cell activation, such as T cell proliferation. A highly potent response may be one with an $EC_{50}$ value in the nM-pM range, for example 500 nM or lower, preferably 1 nM or lower, or 500 pM or lower.

Molecules encompassed by the present invention may have an improved half-life. Methods for determining whether a protein has an improved half-life will be apparent to the skilled person. For example, the ability of a protein to bind to a neonatal Fc receptor (FcRn) is assessed. In this regard, increased binding affinity for FcRn increases the serum half-life of the protein (see for example, Kim et al. Eur J Immunol., 24:2429, 1994).

The half-life of a protein disclosed herein can also be measured by pharmacokinetic studies, e.g., according to the method described by Kim et al. Eur J of Immunol 24: 542, 1994. According to this method radiolabeled protein is injected intravenously into mice and its plasma concentration is periodically measured as a function of time, for example at 3 minutes to 72 hours after the injection. Alternatively, unlabelled protein of the disclosure can be injected and its plasma concentration periodically measured using an ELISA. The clearance curve thus obtained should be biphasic, that is, an alpha phase and beta phase. For the determination of the in vivo half-life of the protein, the clearance rate in beta-phase is calculated and compared with that of the wild type or unmodified protein.

Structural characteristics of a binding molecule described herein, such as crossing angle, tilt angle, roll angle, and peptide residue binding contacts may be determined. Methods to determine such structural characteristics may comprise determining, for example, a three-dimensional atomic structure of a binding molecule bound to SLSNRLYYL (SEQ ID NO: 1) in complex with HLA-A*02.

As used herein, the term "three-dimensional atomic structure" refers to a model of the three-dimensional arrangement of atoms of a protein or protein complex. The three-dimensional atomic structure may be based on a set of atomic coordinates. As used herein, the term "atomic coordinates" or "set of coordinates" refers to a set of values which define the position of one or more atoms in a protein with reference to a system of axes. The atomic coordinates may be used in a computer to generate a representation, e.g. an image of the three-dimensional structure of proteins which can be displayed by the computer and/or represented in an electronic file. Such atomic structures may be determined using techniques well known in the art, including x-ray crystallography, nuclear magnetic resonance (NMR) or cryo-electron microscopy (cryo-EM). For example, the three-dimensional atomic structure may be an x-ray crystal structure. An x-ray crystal structure is a three-dimensional atomic structure of a protein or protein complex that is obtained using x-ray crystallography. X-ray crystallography techniques are well known in the art. A suitable technique is described in Example 7 under the heading "X-ray crystallography".

The X-ray crystal structure may be obtained by an x-ray crystallography technique known as molecular replacement. Methods of molecular replacement are generally known by those skilled in the art and can be performed using publicly available software packages. Generally, molecular replacement involves the following steps: i) X-ray diffraction data are collected from a crystal of a crystallized target protein complex, then ii) the X-ray diffraction data are transformed to calculate a Patterson function, then iii) the Patterson function of the crystallized target structure is compared with a Patterson function calculated from one or more known structures (referred to in the art as a "search structure" or "search model"), iv) the Patterson function of the search structure is rotated on the target structure Patterson function to determine the correct orientation of the search structure in the crystal to obtain a rotation function, v) a translation function is then calculated to determine the location of the search structure with respect to the crystal axes. Alternatively, likelihood-based molecular replacement methods can be used to determine the location of the search structure. Once the search structure has been correctly positioned in the unit cell, initial phases for the experimental data can be calculated. These phases are necessary for calculation of an electron density map from which an initial three-dimensional atomic structure is determined and refined. Preferably, the structural features (e.g., amino acid sequence, conserved disulfide bonds, and beta-strands or beta-sheets) of the search models are related to the crystallized target complex. Suitable search models can be obtained from a protein structure database such as the RCSB Protein Data Bank (RCSB PDB). Suitable search models for determining the three-dimensional atomic structure of a complex formed by the pHLA and a binding molecule include the atomic coordinates of known TCR and pHLA structures. The electron density map can, in turn, be subjected to any well-known model building and structure refinement techniques to provide a final, accurate structure of the unknown (i.e. target) crystallized molecular structure.

Once a three-dimensional atomic structure of the binding molecule bound to the pHLA complex is obtained, structural characteristics such as the binding geometry (e.g., crossing, roll and tilt angles) and peptide residue binding contacts can be determined, based on the positions of the atoms in the structure.

The "pHLA crossing angle" or "crossing angle" (also known in the art as "docking angle") is a parameter known in the art for TCRs (see Rudolph et al. (2006) Annu. Rev. Immunol. 24:419). Specifically, the crossing angle is the angle formed between two vectors: a HLA groove vector and a TCR interdomain vector (also referred to herein as the "TCR cystine vector").

The HLA groove vector (also referred to as the "HLA peptide-binding groove vector") is the directed line segment (or vector) corresponding to the peptide positioned across the HLA peptide binding groove, i.e., from N to C-terminus of the peptide. In this regard, the HLA groove vector follows the two parallel HLA groove helices with the direction N-terminus to C-terminus of HLA helix 1 and passing through the HLA centroid. The TCR interdomain vector is the directed line segment (or vector) connecting the intrachain disulfide bond in the TCR alpha chain variable domain to the intrachain disulfide bond in the TCR beta chain variable domain (in the direction of alpha chain to beta chain).

Similarly the "tilt angle" of a binding molecule is the angle between a "TCR symmetry vector" and the HLA groove vector. The TCR symmetry vector represents the pseudo-two-fold symmetry axis of the TCR variable subunits and points in direction of its CDRs and passes through the TCR centroid.

The "roll angle" of a binding molecule is the angle formed between a "second HLA vector" or "HLA v2 vector" and the TCR symmetry vector. The second HLA vector (HLA v2 vector) is generated perpendicular to the HLA groove vector and points from HLA helix 1 to HLA helix 2. The two vectors meet at the centroid of the HLA helices.

Methods for calculating the above angles are known in the art and include those described by Rudolph et al. (2006) Annu. Rev. Immunol. 24:419 and Mareeva et al. (2006) JBC 283:29053.

A binding molecule of the invention may be assessed to determine its peptide residue binding contacts. The phrase "peptide residue binding contacts" refers to binding interactions formed between amino acid residues of the peptide within the peptide-HLA complex and amino acid residues of the binding molecule. Each peptide residue that is contacted by the binding molecule, when the binding molecule is bound to the pHLA complex, is considered to be a peptide residue binding contact. For example, there may be 4, 5, 6, 7, 8 or 9 or more, peptide residue binding contacts. Of these peptide reside binding contacts, there may be a minimum number (e.g., 4, 5, 6, 7, 8 or 9) that are sufficient for specific binding of the binding molecule to the pHLA complex.

Amino acid residue binding contacts can be determined using any method known in the art and may comprise measuring distances between atoms in a three-dimensional atomic structure of the binding molecule bound to the pHLA complex. For example, residues between the binding molecule and the peptide may be identified to be in binding contact if the distance between any atom from a binding molecule residue and any atom from a peptide residue is equal to 4.1 Å or less. Alternatively, or additionally, binding interactions (e.g., peptide residue binding contacts) can be identified from the three-dimensional atomic structure based on known atomic interaction geometry for different types of interactions, e.g., hydrogen bonds (H-bond), electrostatic interactions, van de Waals (vdW) interactions. For example, an H-bond binding contact can be defined as an interaction between donor atom and acceptor atom, where the donor-acceptor distance in the three-dimensional atomic structure is about 3.0 Å or less and the donor hydrogen acceptor angle is within 450 to 180°. A vdW binding contact can defined as an interaction between two heavy atoms which are within about 4 Å of one another in the three-dimensional atomic structure. Methods of identifying peptide residue binding contacts may comprise performing molecular dynamics simulations using publicly available software packages.

Nucleic Acids, Vectors and Host Cells

The present invention provides a nucleic acid encoding a binding molecule of the invention. The TCR alpha and beta chain variable domains of the binding molecule may be encoded within a single open reading frame, or within two distinct open reading frames. Alternatively, the TCR alpha and beta chain variable domains of the binding molecule may be encoded on separate nucleic acids. The term "nucleic acid" includes but is not limited to ribonucleic acid (RNA) and deoxyribonucleic acid (DNA) molecules, which may be single or double stranded. The nucleic acid may be present in whole cells, in a cell lysate, or may be in an isolated, partially purified or substantially pure form. A nucleic acid is "isolated" or "rendered substantially pure" when purified away from other cellular components or other contaminants, e.g., other cellular nucleic acids or proteins, by standard techniques. The nucleic acid may be recombinant and/or non-naturally occurring and/or engineered. The nucleic acid sequence may be codon optimised, in accordance with the expression system utilised. As is known to those skilled in the art, expression systems may include bacterial cells such as E. coli, or yeast cells, or mammalian cells, or insect cells, or they may be cell free expression systems.

The present invention also provides constructs in the form of plasmids, vectors, transcription or expression cassettes which comprise at least one nucleic acid as described above. In particular, the invention provides an expression vector comprising the nucleic acid of the invention. The terms "vector", "cloning vector" and "expression vector" refer to a vehicle by which a DNA or RNA sequence (e.g. a foreign gene) can be introduced into a host cell, so as to transform the host and optionally promote expression (e.g. transcription and translation) of the introduced sequence. The present invention also provides a recombinant host cell which comprises one or more the constructs as above. As mentioned, a nucleic acid encoding a binding molecule of the invention forms an aspect of the present invention, as does a method of production of the binding molecule comprising expression from a nucleic acid encoding a binding molecule of the invention. Expression may conveniently be achieved by culturing recombinant host cells containing the nucleic acid under appropriate conditions. Following production by expression, a binding molecule may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art. For a review, see for example Pluckthun, Bio/Technology 9:545-551 (1991). Expression in eukaryotic cells in culture is also available to those skilled in the art as an option for production of a binding molecule, see for recent review, for example Reff, Curr. Opinion Biotech. 4:573-576 (1993); Trill et al., Curr. Opinion Biotech. 6:553-560 (1995).

Suitable vectors can be chosen or constructed, containing appropriate regulatory sequences, including promoter sequences, terminator sequences, polyadenylation sequences, enhancer sequences, marker genes and other sequences as appropriate. Vectors may be any suitable vectors known in the art, including plasmids or viral vectors (e.g. 'phage, or phagemid), as appropriate. For further details see, for example, Sambrook et al., Molecular Cloning: A Laboratory Manual: 2nd Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., Short Protocols in Molecular Biology, 2nd Edition, John Wiley & Sons (1992).

The present invention also provides a host cell containing a nucleic acid as disclosed herein. The invention also provides a cell harbouring
(a) an expression vector of the invention; or
(b) a first expression vector comprising a nucleic acid encoding a first polypeptide comprising the TCR alpha chain variable domain of a binding molecule of the invention and a second expression vector comprising a nucleic acid encoding a second polypeptide comprising the TCR beta chain variable domain of a binding molecule of the invention. Also provided is a non-naturally occurring and/or purified and/or engineered cell, preferably a T-cell, presenting the binding molecule of the invention.

Further, the invention provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene.

Suitable host cells for cloning or expression of polynucleotides and/or vectors of the present invention are known in the art. Suitable host cells for the expression of (glycosylated) proteins are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse Sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumour (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for protein production, see, e.g., Yazaki, P. and Wu, A. M., Methods in Molecular Biology, Vol. 248, Lo, B. K. C. (ed.), Humana Press, Totowa, NJ (2004), pp. 255-268. The host cell may be eukaryotic, e.g., a Chinese Hamster Ovary (CHO) cell or lymphoid cell (e.g., Y0, NS0, Sp20 cell). Alternatively, the host cell may be prokaryotic, e.g., an *E. coli* cell.

The nucleic acid of the invention may be integrated into the genome (e.g. chromosome) of the host cell. Integration may be promoted by inclusion of sequences which promote recombination with the genome, in accordance with standard techniques.

Methods of Making Binding Molecules

Further provided herein are methods for producing a binding molecule of the invention. In one aspect, the methods comprise a) maintaining a cell of the invention under conditions suitable for expression of the binding molecule, and b) isolating the binding molecule. In another aspect, the methods comprise
a) providing a first cell capable of expressing a first polypeptide comprising the TCR alpha chain variable domain of a binding molecule of the invention and a second cell capable of expressing a second polypeptide comprising the TCR beta chain variable domain of a binding molecule of the invention;
b) maintaining the first cell under conditions suitable for expression of the first polypeptide and maintaining the second cell under conditions suitable for expression of the second polypeptide;
c) isolating the first and second polypeptides from the cells; and
d) complexing the first and second polypeptides to form the binding molecule of the invention.

Methods of producing recombinant proteins are well known in the art. Nucleic acids encoding the protein can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary mammalian cells used for expressing a protein are CHO cells, myeloma cells or HEK cells. Preferred cells for producing the binding molecules of the invention are *E. coli* cells. Molecular cloning techniques to achieve these ends are known in the art and described, for example in Ausubel et al. (editors), Current Protocols in Molecular Biology, Greene Pub. Associates and Wiley-Interscience (1988, including all updates until present) or Sambrook et al. Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

The nucleic acid may be inserted operably linked to a promoter in an expression construct or expression vector for further cloning (amplification of the DNA) or for expression in a cell-free system or in cells. As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid. As used herein, the term "operably linked to" means positioning a promoter relative to a nucleic acid such that expression of the nucleic acid is controlled by the promoter.

Many vectors for expression in cells are commercially available. The vector components generally include, but are not limited to, one or more of the following: a signal sequence, a sequence encoding a protein (e.g., derived from the information provided herein), an enhancer element, a promoter, and a transcription termination sequence. The skilled person will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-a promoter (EF1), small nuclear RNA promoters (Ula and Ulb), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or an active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GALA promoter, the CUP1 promoter, the PH05 promoter, the nmt promoter, the RPR1 promoter, or the TEF1 promoter.

The host cells used to produce the protein may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Methods for isolating a protein are known in the art. Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing.

These methods are known in the art and described, for example in WO99/57134 or Ed Harlow and David Lane (editors) Antibodies: A Laboratory Manual, Cold Spring Harbor Laboratory, (1988). The skilled person will also be aware that a protein can be modified to include a tag to facilitate purification or detection, e.g., a poly-histidine tag, a hexa-histidine tag, an influenza virus hemagglutinin (HA) tag, a Simian Virus 5 (V5) tag, a LLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Molecules of the invention may be amenable to high yield purification. Yield may be determined based on the amount of material retained during the purification process (i.e. the amount of correctly folded material obtained at the end of the purification process relative to the amount of solubilised material obtained prior to refolding), and or yield may be based on the amount of correctly folded material obtained at the end of the purification process, relative to the original culture volume. High yield means greater than 1%, or greater than 5%, or higher yield. High yield means greater than 1 mg/ml, or greater than 3 mg/ml, or greater than 5 mg/ml, or higher yield.

Pharmaceutical Compositions and Medical Methods

For administration to patients, the molecules, nucleic acids, expression vectors and/or cells of the invention may be provided as part of a pharmaceutical composition together with one or more pharmaceutically acceptable carriers or excipients (for example a buffering agent, also known as a "buffer"). This pharmaceutical composition may be in any suitable form, (e.g. depending upon the desired method of administering it to a patient). It may be provided in unit dosage form, and will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, intrathecal or intravenous), enteral (including oral or rectal), inhalation or intranasal routes. Such compositions may be prepared by any method known in the art of pharmacy, for example by mixing the active ingredient with the carrier(s) or excipient(s) under sterile conditions. Methods for preparing a protein into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions will commonly comprise a solution of the binding molecule of the invention (or the nucleic acid, cell, or vector of the invention) dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of molecules of the present invention in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Binding molecules, pharmaceutical compositions, vectors, nucleic acids and cells of the invention may be provided in substantially pure form, for example, at least 80%, at least 85%, at least 90%, at least 91%, at least 92%, at least 93%, at least 94%, at least 95%, at least 96%, at least 97%, at least 98%, at least 99% or 100% pure.

Binding molecules of the invention may have an ideal safety profile for use as therapeutic reagents. "Safety profile", as used herein, refers to the capacity to distinguish a tumour cell, in particular a SLSNRLYYL (SEQ ID NO: 1)-HLA-A*02 complex presenting tumour cell, from a healthy cell. This capacity is often expressed by indication of the safety window. In this case the binding molecules may be in soluble form and may preferably be fused to an immune effector. Suitable immune effectors are described herein and include but are not limited to, cytokines, such as IL-2 and IFN-γ; superantigens and mutants thereof; chemokines such as IL-8, platelet factor 4, melanoma growth stimulatory protein; antibodies and antibody like scaffolds, including fragments, derivatives and variants thereof that bind to antigens on immune cells such as T cells or NK cell (e.g. anti-CD3, anti-CD28 or anti-CD16); and Fc receptor or complement activators. An ideal safety profile means that in addition to demonstrating good specificity, the binding molecules of the invention may have passed further preclinical safety tests. Examples of such tests include whole blood assays to confirm minimal cytokine release in the presence of whole blood and thus low risk of causing a potential cytokine release syndrome in vivo, and alloreactivity tests to confirm low potential for recognition of alternative HLA types.

Suitable dosages of the molecules of the present invention can vary between wide limits, depending upon the disease or disorder to be treated, the age and condition of the subject to be treated, etc. Preferably, the subject is a human. A physician may ultimately determine appropriate dosages to be used. Administration of the TCR anti-CD3 fusion molecule may be in a "therapeutically effective amount," this being an amount sufficient to show benefit to the patient.

The binding molecule of the invention may be further associated with a therapeutic agent. Therapeutic agents which may be associated with the molecules of the invention include immune-modulators and effectors, radioactive compounds, enzymes (perforin for example) or chemotherapeutic agents (cis-platin for example). To ensure that toxic effects are exercised in the desired location the toxin could be inside a liposome linked to the binding molecule described herein so that the compound is released slowly. This will prevent damaging effects during the transport in the body and ensure that the toxin has maximum effect after binding of the binding molecule described herein to the relevant antigen presenting cells.

The binding molecule, nucleic acid, vector, pharmaceutical composition and cell of the invention may be used for treating diseases such as cancer. The cancer to be treated may be a cancer associated with PIWIL1 expression. By "associated with PIWIL1 expression" it is meant that the cancer comprises cancer cells that express PIWIL1. In this regard, the cancer may be a PIWIL1-positive cancer. The cancer may be known to be associated with expression of PIWIL1. For example, it may be known that the prevalence of PIWIL1 expression is elevated in the cancer and thus PIWIL1 expression may not be assessed, or may be assessed retrospectively. Alternatively, PIWIL1 expression can be assessed using any method known in the art, including, for example, histological methods or other quantitative or qualitative measurements, including PCR, RNA expression analysis, and/or kits or sequence panels designed to measure the expression level of PIWIL1. The invention is not intended to be limited to the treatment of cancers for which PIWIL1 expression can be detected by histological methods. Rather, the binding molecules of the invention may be useful for the treatment of cancers and tumour types which are considered to be associated with PIWIL1 expression.

PIWIL1 expression, when detected by histological methods like immunohistochemistry (IHC), can be quantified using an H-score. Expression of PIWIL1 in individual cells or their sub-cellular compartments within a tumour are first detected and classified as either positive or negative. The positive cells can be further classified into high, medium, or low based on the IHC signal intensity. The H-score captures both the intensity and the proportion of the biomarker of interest from the IHC image and comprises values between 0 and 300, thereby offering a dynamic range to quantify abundance or a particular marker or gene.

Cancers associated with PIWIL1 expression include, but are not limited to, gastric cancer, pancreatic cancer, colorectal cancer, or oesophageal cancer, or thyroid cancer. For example, the cancer associated with PIWIL1 expression may be colorectal cancer. Alternatively or additionally, the cancer associated with PIWIL1 expression may be pancreatic cancer, such as pancreatic adenocarcinoma. The oesophageal cancer may be gastroesophageal junction (GEJ) adenocarcinoma. The cancer may be microsatellite instability high (MSI-high).

The antigen PIWIL1 constitutes a cancer marker and, therefore, has the potential to be used to indicate the effectiveness of an anti-cancer therapy or detecting recurrence of the disease. Thus, in another aspect, the invention provides the binding molecule, the nucleic acid, the vector, the host cell, or the pharmaceutical composition of the invention, for use as a diagnostic agent or in a diagnostic method, in particular for use as an in vivo diagnostic agent or in an in vivo diagnostic method. In preferred embodiments, the diagnostic agent/method is for the diagnosis of a proliferative disease. In more preferred embodiments, the diagnostic agent/method is for the diagnosis of a cancer that presents a peptide comprising or consisting of the amino acid sequence of SLSNRLYYL (SEQ ID NO: 1) in complex with HLA-A*02.

Also provided by the invention are:
  a binding molecule, nucleic acid, vector, pharmaceutical composition or cell of the invention for use in medicine, preferably for use in a human subject and/or preferably for use in a method of treating cancer or a tumour;

use of a binding molecule, nucleic acid, vector, pharmaceutical composition or cell of the invention in the manufacture of a medicament for treating cancer or a tumour;

a method of treating cancer or a tumour in a patient, comprising administering to the patient a binding molecule, nucleic acid, vector, pharmaceutical composition or cell of the invention;

an injectable formulation for administering to a human subject comprising a binding molecule, nucleic acid, vector pharmaceutical composition or cell of the invention.

Kits and Articles of Manufacture

In another aspect, a kit or an article of manufacture containing materials useful for the treatment and/or prevention of the diseases described above is provided.

The kit may comprise (a) a container comprising the binding molecule, nucleic acid, vector or cell of the invention, optionally in a pharmaceutically acceptable carrier or diluent; and (b) a package insert with instructions for treating a disease (e.g., cancer) in a subject. The kit may further comprise (c) at least one further therapeutically active compound or drug.

The package insert may be on or associated with the container. Suitable containers include, for example, bottles, vials, syringes, etc. The containers may be formed from a variety of materials such as glass or plastic. The container holds or contains a composition that comprises the molecule, nucleic acid, vector or cell of the invention and may have a sterile access port (for example, the container may be an intravenous solution bag or a vial having a stopper pierceable by a hypodermic injection needle). At least one active agent in the composition is the binding molecule, nucleic acid, vector or cell of the invention. The label or package insert indicates that the composition is used for treating a subject eligible for treatment, e.g., one having or predisposed to developing a disease described herein, with specific guidance regarding dosing amounts and intervals of the composition and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The invention also includes particles displaying binding molecules of the invention and the inclusion of said particles within a library of particles. Such particles include but are not limited to phage, yeast cells, ribosomes, or mammalian cells. Method of producing such particles and libraries are known in the art (for example see WO2004/044004; WO01/48145, Chervin et al. (2008) J. Immuno. Methods 339.2: 175-184).

Various modifications of the invention in addition to those shown and described herein will become apparent to those skilled in the art from the foregoing description and fall within the scope of the appended claims. Preferred features of each aspect of the invention are as for each of the other aspects mutatis mutandis. The documents referred to herein are incorporated by reference to the fullest extent permitted by law.

DESCRIPTION OF THE DRAWINGS

FIG. 4.

FIG. 5: schematic diagram of an exemplary multi-domain, single-chain binding molecule of the invention. (FIG. 5A) shows a representation of the domain arrangement from the N- to C-terminus and (FIG. 5B) shows a hypothetical representation of the folded structure of the molecule.

DESCRIPTION OF THE SEQUENCES

Figure 1:
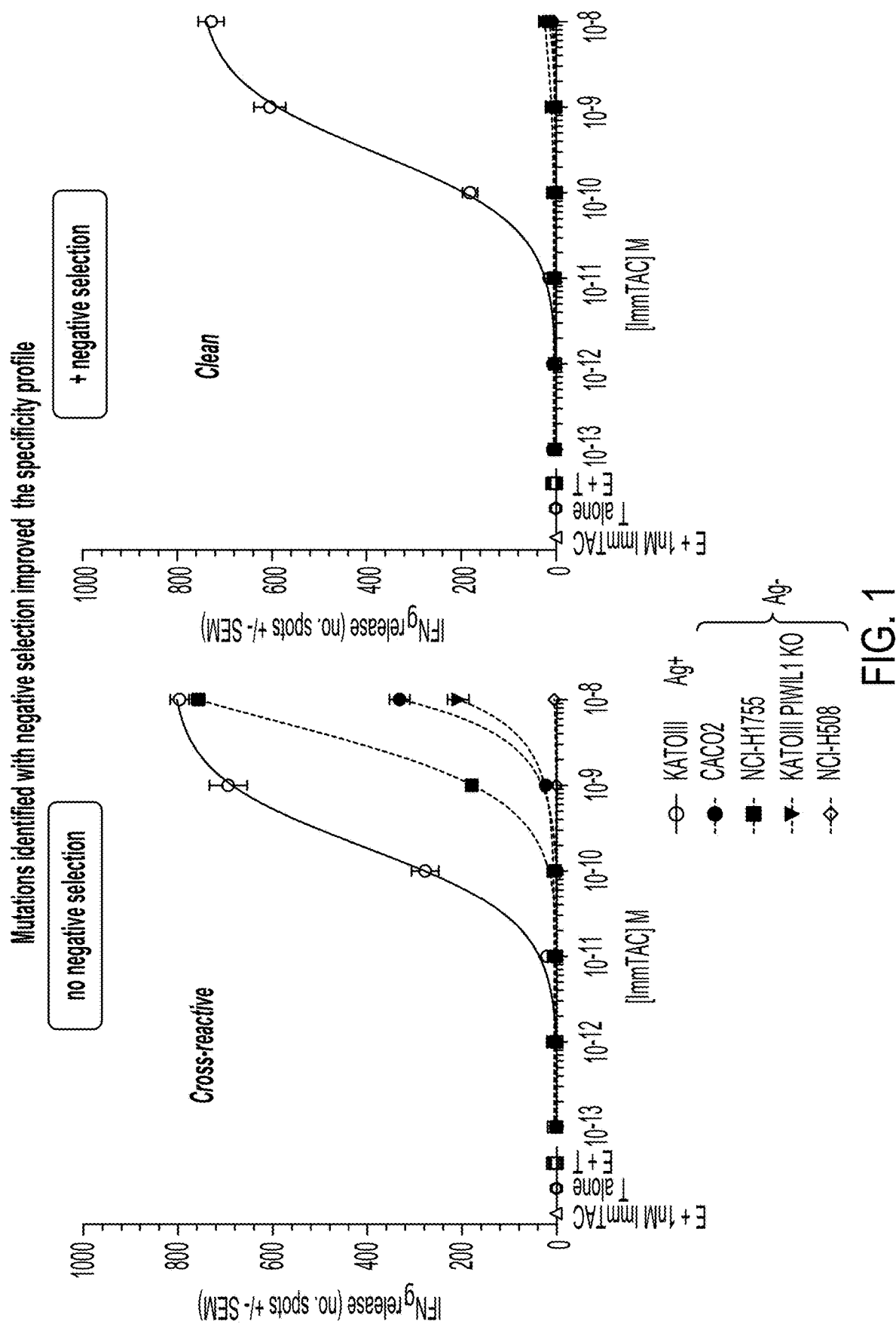
FIG. 1: T cell activation measured by IFNγ release against antigen positive and antigen negative cancer call lines using selected TCR variants ("a6b3" for left hand graph and "a6b6" for right hand graph) obtained in the presence or absence of negative selection during affinity maturation.

HLA-A*02 Restricted Peptides
    Source protein gene is indicated in brackets below.

```
                (PIWIL1):
                                SEQ ID NO: 1
                SLSNRLYYL (DOCK11):
                                SEQ ID NO: 97
                MLDKYSHYL
```

Alpha Chain of an Exemplary Scaffold TCR (SEQ ID NO: 2)

```
LAKTTQPISM DSYEGQEVNI TCSHNNIATN DYITWYQQFP

SQGPRFIIQG YKTKVTNEVA SLFIPADRKS STLSLPRVSL
```

-continued
```
SDTAVYYCLA WGGTDKLIFG TGTRLQVFPN IQNPDPAVYQ

LRDSKSSDKS VCLFTDFDSQ TNVSQSKDSD VYITDKCVLD

MRSMDFKSNS AVAWSNKSDF ACANAFNNSI IPEDT
```

SEQ ID NO: 2 is an amino acid sequence of the alpha chain of an exemplary wild type (e.g., "scaffold") TCR (comprising the alpha chain of SEQ ID NO: 2 and the beta chain of SEQ ID NO: 12) that binds to SLSNRLYYL (SEQ ID NO: 1) in complex with HLA-A2. This TCR is referred to as "S8" herein. The alpha chain comprises a variable domain (SEQ ID NO: 3) and a constant domain (SEQ ID NO: 4, italics). CDRs (CDR1, CDR2 and CDR3) are underlined and are designated SEQ ID NO: 5, 6 and 7 respectively, framework regions (FR1, FR2, FR3 and FR4) are in regular text and are designated SEQ ID NO: 8, 9, 10 and 11 respectively. The constant domain includes a T48C (numbered according to SEQ ID NO: 4) mutation (relative to a wild type constant domain), in bold text, to introduce a non-native covalent disulfide bond between the alpha and beta chains.

Beta Chain of an Exemplary Scaffold TCR (SEQ ID NO: 12)

```
EAGVAQSPRY KIIEKRQSVA FWCNPISGHA TLYWYQQILG

QGPKLLIQFQ NNGVVDDSQL PKDRFSAERL KGVDSTLKIQ

PAKLEDSAVY LCASSLDWVG SGETQYFGPG TRLLVLEDLK

NVFPPEVAVF EPSEAEISHT QKATLVCLAT GFYPDHVELS

WWVNGKEVHS GVCTDPQPLK EQPALNDSRY ALSSRLRVSA

TEWQDPRNHF RCQVQFYGLS ENDEWTQDRA KPVTQIVSAE

AWGRAD
```

SEQ ID NO: 12 is an amino acid sequence of the beta chain of an exemplary wild type (e.g., "scaffold") TCR (comprising the alpha chain of SEQ ID NO: 2 and the beta chain of SEQ ID NO: 12) that binds to SLSNRLYYL (SEQ ID NO: 1) in complex with HLA-A2. This TCR is referred to as "S8" herein. The beta chain comprises a variable domain (SEQ ID NO: 13) and a constant domain (SEQ ID NO: 14, italics). CDRs (CDR1, CDR2 and CDR3) are underlined and are designated SEQ ID NO: 15, 16 and 17 respectively, framework regions (FR1, FR2, FR3 and FR4) are in regular text and are designated SEQ ID NO: 18, 19, 20 and 21 respectively. The constant domain includes a S57C (numbered according to SEQ ID NO: 14) mutation (relative to a wild type constant domain), in bold text, to introduce a non-native covalent disulfide bond between the alpha and beta chains. Also in bold text is a C75A mutations (numbered according to SEQ ID NO: 14) which removes a native cysteine to decrease incorrect disulphide formation Exemplary Mutated TCR Alpha Chain Variable Domains The following sequences are exemplary alpha chain variable domains which contain mutations relative to the wild type sequence in SEQ ID NO: 3. The CDRs are underlined and the mutations are shown in bold.

Alpha chain variable domain "a36" (SEQ ID NO: 22) comprising CDRs (CDR1, CDR2 and CDR3-underlined) designated SEQ ID NO: 23, 24 and 25, respectively, and framework regions (FR1, FR2, FR3 and FR4—regular text) designated SEQ ID NO: 8, 26, 27 and 11, respectively:

```
LAKTTQPISM DSYEGQEVNI TCSHNYIAAN DFITWYQQFP

SQGPRFFIQG YKTNVQNEVA SLFIPADRKS STLSLPRVSL

SDTAVYYCLA WGGTDVLPFG TGTRLQVFP
```

Alpha chain variable domain "a40" (SEQ ID NO: 28) comprising CDRs (CDR1, CDR2 and CDR3-underlined) designated SEQ ID NO: 23, 24 and 29, respectively, and framework regions (FR1, FR2, FR3 and FR4—regular text) designated SEQ ID NO: 8, 26, 27 and 11, respectively:

```
LAKTTQPISM DSYEGQEVNI TCSHNYIAAN DFITWYQQFP

SQGPRFFIQG YKTNVQNEVA SLFIPADRKS STLSLPRVSL

SDTAVYYCLA WGGTDLLPFG TGTRLQVFP
```

Alpha chain variable domain "a58" (SEQ ID NO: 30) comprising CDRs (CDR1, CDR2 and CDR3-underlined) designated SEQ ID NO: 23, 24 and 29, respectively, and framework regions (FR1, FR2, FR3 and FR4—regular text) designated SEQ ID NO: 31, 26, 27 and 11, respectively

```
AAKTTQPISM DSYEGQEVNI TCSHNYIAAN DFITWYQQFP

SQGPRFFIQG YKTNVQNEVA SLFIPADRKS STLSLPRVSL

SDTAVYYCLA WGGTDLLPFG TGTRLQVFP
```

Alpha chain variable domain "a61" (SEQ ID NO: 32) comprising CDRs (CDR1, CDR2 and CDR3-underlined) designated SEQ ID NO: 23, 24 and 29, respectively, and framework regions (FR1, FR2, FR3 and FR4—regular text) designated SEQ ID NO: 33, 26, 118 and 11, respectively:

```
LAKTTQPISM DSYEGQEVNI PCSHNYIAAN DFITWYQQFP

SQGPRFFIQG YKTNVQNEVA SLFISADRKS STLSLPRVSL

SDTAVYYCLA WGGTDLLPFG TGTRLQVFP
```

Alpha chain variable domain "a67" (SEQ ID NO: 34) comprising CDRs (CDR1, CDR2 and CDR3-underlined) designated SEQ ID NO: 23, 24 and 29, respectively, and framework regions (FR1, FR2, FR3 and FR4—regular text) designated SEQ ID NO: 35, 26, 118 and 11, respectively:

```
AAKTTQPISM DSYEGQEVNI PCSHNYIAAN DFITWYQQFP

SQGPRFFIQG YKTNVQNEVA SLFISADRKS STLSLPRVSL

SDTAVYYCLA WGGTDLLPFG TGTRLQVFP
```

Exemplary Mutated TCR Beta Chain Variable Domains

The following sequences are exemplary beta chain variable domains which contain mutations relative to the wild type sequence in SEQ ID NO: 12. The CDRs are underlined and the mutations are shown in bold.

Beta chain variable domain "b23" (SEQ ID NO: 36) comprising CDRs (CDR1, CDR2 and CDR3-underlined) designated SEQ ID NO: 37, 38 and 41 respectively, framework regions (FR1, FR2, FR3 and FR4—regular text) designated SEQ ID NO: 18, 19, 20 and 21 respectively:

```
EAGVAQSPRY KIIEKRQSVA FWCNPISGHG TLYWYQQILG

QGPKLLIQFH ENGVVDDSQL PKDRFSAERL KGVDSTLKIQ

PAKLEDSAVY LCASSVDWVG DGERQYFGPG TRLLVL
```

Beta chain variable domain "b37" (SEQ ID NO: 40) comprising CDRs (CDR1, CDR2 and CDR3-underlined) designated SEQ ID NO: 37, 38 and 39, respectively, and framework regions (FR1, FR2,

```
EAGVAQSPRY KIIEKRQSVA FWCNPISGHG TLYWYQQILG

QGPKLLIQFH ENGVVDDSQL PKDRFSAERL KGVDSTLKIQ

PAKLEDSAVY LCASSWDWVG DGERQYFGPG TRLLVL
```

Beta chain variable domain "b38" (SEQ ID NO: 42) comprising CDRs (CDR1, CDR2 and CDR3-underlined) designated SEQ ID NO: 43, 38 and 41, respectively, and framework regions (FR1, FR2, FR3 and FR4—regular text) designated SEQ ID NO: 18, 19, 20 and 21, respectively:

```
EAGVAQSPRY KIIEKRQSVA FWCNPITGHG TLYWYQQILG

QGPKLLIQFH ENGVVDDSQL PKDRFSAERL KGVDSTLKIQ

PAKLEDSAVY LCASSVDWVG DGERQYFGPG TRLLVL
```

Beta chain variable domain "b63" (SEQ ID NO: 44) comprising CDRs (CDR1, CDR2 and CDR3-underlined) designated SEQ ID NO: 37, 45 and 41, respectively, and framework regions (FR1, FR2, FR3 and FR4—regular text) designated SEQ ID NO: 18, 19, 20 and 21, respectively:

```
EAGVAQSPRY KIIEKRQSVA FWCNPISGHG TLYWYQQILG

QGPKLLIQFH EEGVVDDSQL PKDRFSAERL KGVDSTLKIQ

PAKLEDSAVY LCASSVDWVG DGERQYFGPG TRLLVL
```

Beta chain variable domain "b68" (SEQ ID NO: 46) comprising CDRs (CDR1, CDR2 and CDR3-underlined) designated SEQ ID NO: 37, 38 and 41, respectively, and framework regions (FR1, FR2, FR3 and FR4—regular text) designated SEQ ID NO: 47, 19, 20 and 21, respectively:

```
EAGVAQSPRY KIIEKGQSVA FWCNPISGHG TLYWYQQILG

QGPKLLIQFH ENGVVDDSQL PKDRFSAERL KGVDSTLKIQ

PAKLEDSAVY LCASSVDWVG DGERQYFGPG TRLLVL
```

Beta chain variable domain "b72" (SEQ ID NO: 48) comprising CDRs (CDR1, CDR2 and CDR3-underlined) designated SEQ ID NO: 37, 45 and 41, respectively, and framework regions (FR1, FR2, FR3 and FR4—regular text) designated SEQ ID NO: 47, 19, 20 and 21, respectively:

```
EAGVAQSPRY KIIEKGQSVA FWCNPISGHG TLYWYQQILG

QGPKLLIQFH EEGVVDDSQL PKDRFSAERL KGVDSTLKIQ

PAKLEDSAVY LCASSVDWVG DGERQYFGPG TRLLVL
```

Exemplary TCRs

The following sequences are TCRs comprising exemplary combinations of the alpha and beta chain variable domains provided above. Constant domains are shown in italics. The CDRs are underlined and the mutations relative to the scaffold TCR sequence (i.e., SEQ ID NO: 2 or 12) are shown in bold.

a40b23 TCR

TCR "a40b23" alpha chain sequence (SEQ ID NO: 49), comprising the a40 variable domain (SEQ ID NO: 28—regular text) described above and the constant domain (SEQ ID NO: 4—italics) from the scaffold TCR described above:

```
LAKTTQPISM DSYEGQEVNI TCSHNYIAAN DFITWYQQFP

SQGPRFFIQG YKTNVQNEVA SLFIPADRKS STLSLPRVSL

SDTAVYYCLA WGGTDLLPFG TGTRLQVFPN IQNPDPAVYQ

LRDSKSSDKS VCLFTDFDSQ TNVSQSKDSD VYITDKCVLD

MRSMDFKSNS AVAWSNKSDF ACANAFNNSI IPEDT
```

TCR "a40b23" beta chain sequence (SEQ ID NO: 50), comprising the b23 variable domain (SEQ ID NO: 36—regular text) and the constant domain (SEQ ID NO: 14—italics) from the scaffold TCR described above:

```
EA GVAQSPRYKI IEKRQSVAFW CNPISGHGTL YWYQQILGQG

PKLLIQFHEN GVVDDSQLPK DRESAERLKG VDSTLKIQPA

KLEDSAVYLC ASSVDWVGDG ERQYFGPGTR LLVLEDLKNV

FPPEVAVFEP SEAEISHTQK ATLVCLATGF YPDHVELSWW

VNGKEVHSGV CTDPQPLKEQ PALNDSRYAL SSRLRVSATF

WQDPRNHERC QVQFYGLSEN DEWTQDRAKP VTQIVSAEAW

GRAD
``` a36b38 TCR

TCR "a36b38" alpha chain sequence (SEQ ID NO: 51), comprising the a36 variable domain (SEQ ID NO: 22—regular text) described above and the constant domain (SEQ ID NO: 4—italics) from the scaffold TCR described above:

```
LAKTTQPISM DSYEGQEVNI TCSHNYIAAN DFITWYQQFP

SQGPRFFIQG YKTNVQNEVA SLFIPADRKS STLSLPRVSL

SDTAVYYCLA WGGTDVLPFG TGTRLQVFPN IQNPDPAVYQ

LRDSKSSDKS VCLFTDFDSQ TNVSQSKDSD VYITDKCVLD

MRSMDFKSNS AVAWSNKSDF ACANAFNNSI IPEDT
```

TCR "a36b38" beta chain sequence (SEQ ID NO: 52), comprising the b38 variable domain (SEQ ID NO: 42—regular text) and the constant domain (SEQ ID NO: 14—italics) from the scaffold TCR described above:

```
EA GVAQSPRYKI IEKRQSVAFW CNPITGHGTL

YWYQQILGQG PKLLIQFHEN GVVDDSQLPK

DRFSAERLKG VDSTLKIQPA KLEDSAVYLC

ASSVDWVGDG ERQYFGPGTR LLVLEDLKNV

FPPEVAVFEP SEAEISHTQK ATLVCLATGF
```

```
YPDHVELSWW VNGKEVHSGV CTDPQPLKEQ

PALNDSRYAL SSRLRVSATF WQDPRNHFRC

QVQFYGLSEN DEWTQDRAKP VTQIVSAEAW

GRAD
``` a40b37 TCR

TCR "a40b23" alpha chain sequence (SEQ ID NO: 49), comprising the a40 variable domain (SEQ ID NO: 28—regular text) described above and the constant domain (SEQ ID NO: 4—italics) from the scaffold TCR described above:

```
LAKTTQPISM DSYEGQEVNI TCSHNYIAAN DFITWYQQFP

SQGPRFFIQG YKTNVQNEVA SLFIPADRKS STLSLPRVSL

SDTAVYYCLA WGGTDLLPFG TGTRLQVEPN IQNPDPAVYQ

LRDSKSSDKS VCLFTDFDSQ TNVSQSKDSD VYITDKCVLD

MRSMDFKSNS AVAWSNKSDF ACANAFNNSI IPEDT
```

TCR "a40b37" beta chain sequence (SEQ ID NO: 53), comprising the b37 variable domain (SEQ ID NO: 40—regular text) and the constant domain (SEQ ID NO: 14—italics) from the scaffold TCR described above:

```
EA GVAQSPRYKI IEKRQSVAFW CNPISGHGTL YWYQQILGQG

PKLLIQFHEN GVVDDSQLPK DRESAERLKG VDSTLKIQPA

KLEDSAVYLC ASSWDWVGDG ERQYFGPGTR LLVLEDLKNV

FPPEVAVFEP SEAEISHTQK ATLVCLATGF YPDHVELSWW

VNGKEVHSGV CTDPQPLKEQ PALNDSRYAL SSRLRVSATF

WQDPRNHFRC QVQFYGLSEN DEWTQDRAKP VTQIVSAEAW

GRAD
``` a58b63 TCR

TCR "a58b63" alpha chain sequence (SEQ ID NO: 54), comprising the a58 variable domain (SEQ ID NO: 30—regular text) described above and the constant domain (SEQ ID NO: 4—italics) from the scaffold TCR described above:

```
AAKTTQPISM DSYEGQEVNI TCSHNYIAAN DFITWYQQFP

SQGPRFFIQG YKTNVQNEVA SLFIPADRKS STLSLPRVSL

SDTAVYYCLA WGGTDLLPFG TGTRLQVFPN IQNPDPAVYQ

LRDSKSSDKS VCLFTDFDSQ TNVSQSKDSD VYITDKCVLD

MRSMDFKSNS AVAWSNKSDF ACANAFNNSI IPEDT
```

TCR "a58b63" beta chain sequence (SEQ ID NO: 55), comprising the b63 variable domain (SEQ ID NO: 44—regular text) and the constant domain (SEQ ID NO: 14—italics) from the scaffold TCR described above:

```
EA GVAQSPRYKI IEKRQSVAFW CNPISGHGTL YWYQQILGQG

PKLLIQFHEE GVVDDSQLPK DRFSAERLKG VDSTLKIQPA

KLEDSAVYLC ASSVDWVGDG ERQYFGPGTR LLVLEDLKNV

FPPEVAVFEP SEAEISHTQK ATLVCLATGF YPDHVELSWW

VNGKEVHSGV CTDPQPLKEQ PALNDSRYAL SSRLRVSATF

WQDPRNHFRC QVQFYGLSEN DEWTQDRAKP VTQIVSAEAW

GRAD
``` a61b68 TCR

TCR "a61b68" alpha chain sequence (SEQ ID NO: 56), comprising the a61 variable domain (SEQ ID NO: 32—regular text) described above and the constant domain (SEQ ID NO: 4—italics) from the scaffold TCR described above:

```
LAKTTQPISM DSYEGQEVNI PCSHNYIAAN

DFITWYQQFP SQGPRFFIQG YKTNVQNEVA

SLFISADRKS STLSLPRVSL SDTAVYYCLA

WGGTDLLPFG TGTRLQVFPN IQNPDPAVYQ

LRDSKSSDKS VCLFTDFDSQ TNVSQSKDSD

VYITDKCVLD MRSMDFKSNS AVAWSNKSDF

ACANAFNNSI IPEDT
```

TCR "a61 b68" beta chain sequence (SEQ ID NO: 57), comprising the b68 variable domain (SEQ ID NO: 46—regular text) and the constant domain (SEQ ID NO: 14—italics) from the scaffold TCR described above:

```
EA GVAQSPRYKI IEKGQSVAFW CNPISGHGTL YWYQQILGQG

PKLLIQFHEN GVVDDSQLPK DRFSAERLKG VDSTLKIQPA

KLEDSAVYLC ASSVDWVGDG ERQYFGPGTR LLVLEDLKNV

FPPEVAVFEP SEAEISHTQK ATLVCLATGF YPDHVELSWW

VNGKEVHSGV CTDPQPLKEQ PALNDSRYAL SSRLRVSATF

WQDPRNHERC QVQFYGLSEN DEWTQDRAKP VTQIVSAEAW

GRAD
``` a67b72

TCR "a67b72" alpha chain sequence (SEQ ID NO: 58), comprising the a67 variable domain (SEQ ID NO: 34—regular text) described above and the constant domain (SEQ ID NO: 4—italics) from the scaffold TCR described above:

```
AAKTTQPISM DSYEGQEVNI PCSHNYIAAN DFITWYQQFP

SQGPRFFIQG YKTNVQNEVA SLFISADRKS STLSLPRVSL

SDTAVYYCLA WGGTDLLPFG TGTRLQVFPN IQNPDPAVYQ

LRDSKSSDKS VCLFTDFDSQ TNVSQSKDSD VYITDKCVLD

MRSMDFKSNS AVAWSNKSDF ACANAFNNSI IPEDT
```

TCR "a67b72" beta chain sequence (SEQ ID NO: 59), comprising the b72 variable domain (SEQ ID NO: 48) and the constant domain (SEQ ID NO: 14) from the scaffold TCR described above:

```
EA GVAQSPRYKI IEKGQSVAFW CNPISGHGTL YWYQQILGQG

PKLLIQFHEE GVVDDSQLPK DRFSAERLKG VDSTLKIQPA

KLEDSAVYLC ASSVDWVGDG ERQYFGPGTR LLVLEDLKNV

FPPEVAVFEP SEAEISHTQK ATLVCLATGF YPDHVELSWW

VNGKEVHSGV CTDPQPLKEQ PALNDSRYAL SSRLRVSATF

WQDPRNHERC QVQFYGLSEN DEWTQDRAKP VTQIVSAEAW

GRAD
```

Exemplary Anti-CD3 Antibody Sequences
Anti-CD3 scFv: U0

SEQ ID NO: 60 is the amino acid sequence of an exemplary anti-CD3 scFv referred to herein as "U0". The light chain variable domain (VL) is in italics and is designated SEQ ID NO: 61. The light chain CDRs (CDR1, CDR2 and CDR3) are underlined and are designated SEQ ID NO: 62, YTS and SEQ ID NO: 64. The heavy chain variable domain (VH) is shown in bold and is designated SEQ ID NO: 65. The heavy chain CDRs (CDR1, CDR2 and CDR3) are underlined and are designated SEQ ID NO: 66, 67 and 68. A glycine-serine linker, linking the VL and VH, is shown in plain text and is designated SEQ ID NO: 86.

```
SEQ ID NO: 60:
AIQMTQSPSS LSASVGDRVT ITCRASQDIR NYLNWYQQKP

GKAPKLLIYY TSRLESGVPS RFSGSGSGTD YTLTISSLQP

EDFATYYCQQ GNTLPWTFGQ GTKVEIKGGG GSGGGGSGGG

GSGGGGSGGG SEVQLVESGG GLVQPGGSLR LSCAASGYSF

TGYTMNWVRQ APGKGLEWVA LINPYKGVST YNQKFKDRFT

ISVDKSKNTA YLQMNSLRAE DTAVYYCARS GYYGDSDWYF

DVWGQGTLVTVSS
```

Anti-CD3 scFv: U28

SEQ ID NO: 70 is the amino acid sequence of another exemplary anti-CD3 scFv referred to herein as "U28". This sequence is the same as SEQ ID NO: 60 above, except for two substitutions double-underlined (T164A and I201F). The light chain variable domain (VL) is in italics and is designated SEQ ID NO: 61. The light chain CDRs (CDR1, CDR2 and CDR3) are underlined and are designated SEQ ID NO: 62, YTS and SEQ ID NO: 64. The heavy chain variable domain (VH) is shown in bold and is designated SEQ ID NO: 69. The heavy chain CDRs (CDR1, CDR2 and CDR3) are underlined (CDR1 includes the double underlined alanine residue) and are designated SEQ ID NO: 71, 67 and 68. A glycine-serine linker, linking the VL and VH, is shown in plain text and is designated SEQ ID NO: 86.

```
SEQ ID NO: 70:
AIQMTQSPSS LSASVGDRVT ITCRASQDIR

NYLNWYQQKP GKAPKLLIYY TSRLESGVPS

RFSGSGSGTD YTLTISSLQP EDFATYYCQQ

GNTLPWTFGQ GTKVEIKGGG GSGGGGSGGG

GSGGGGSGGG SEVQLVESGG GLVQPGGSLR

LSCAASGYSF TGYAMNWVRQ APGKGLEWVA

LINPYKGVST YNQKFKDRFT FSVDKSKNTA

YLQMNSLRAE DTAVYYCARS GYYGDSDWYF

DVWGQGTLVTVSS
```

Exemplary TCR-Anti-CD3 Fusion Sequences
a40b23U28

"a40b23U28" is a binding molecule comprising the TCR "a40" alpha chain (SEQ ID NO: 49) described above and a TCR beta chain-anti-CD3 fusion (SEQ ID NO: 119). The beta chain-anti-CD3 fusion sequence (SEQ ID NO: 119) is shown below and comprises the U28 anti-CD3 scFv (SEQ ID NO: 70, italics) described above fused to the TCR "b23" beta chain (SEQ ID NO: 50) described above. The TCR beta chain and anti-CD3 scFv sequences are linked via a glycine-serine linker (underlined), designated SEQ ID NO: 72.

```
SEQ ID NO: 119:
AIQMTQSPSS LSASVGDRVT ITCRASQDIR

NYLNWYQQKP GKAPKLLIYY TSRLESGVPS

RFSGSGSGTD YTLTISSLQP EDFATYYCQQ

GNTLPWTFGQ GTKVEIKGGG GSGGGGSGGG

GSGGGGSGGG SEVQLVESGG GLVQPGGSLR

LSCAASGYSF TGYAMNWVRQ APGKGLEWVA

LINPYKGVST YNQKFKDRFT FSVDKSKNTA

YLQMNSLRAE DTAVYYCARS GYYGDSDWYF

DVWGQGTLVT VSSGGGGSEA GVAQSPRYKI

IEKRQSVAFW CNPISGHGTL YWYQQILGQG

PKLLIQFHEN GVVDDSQLPK DRFSAERLKG

VDSTLKIQPA KLEDSAVYLC ASSVDWVGDG

ERQYFGPGTR LLVLEDLKNV FPPEVAVFEP

SEAEISHTQK ATLVCLATGF YPDHVELSWW

VNGKEVHSGV CTDPQPLKEQ PALNDSRYAL

SSRLRVSATF WQDPRNHERC QVQFYGLSEN

DEWTQDRAKP VTQIVSAEAW GRAD
``` a36b38U28

"a36b38U280" is a binding molecule comprising the TCR "a36b38" alpha chain (SEQ ID NO: 51) described above and a TCR beta chain-anti-CD3 fusion (SEQ ID NO: 73). The beta chain-anti-CD3 fusion sequence (SEQ ID NO: 73) is shown below and comprises the U28 anti-CD3 scFv (SEQ ID NO: 70, italics) described above fused to the TCR "a36b38" beta chain (SEQ ID NO: 52) described above. The TCR beta chain and anti-CD3 scFv sequences are covalently linked via a glycine-serine linker (underlined), designated SEQ ID NO: 72.

```
SEQ ID NO: 73:
AIQMTQSPSS LSASVGDRVT ITCRASQDIR

NYLNWYQQKP GKAPKLLIYY TSRLESGVPS

RFSGSGSGTD YTLTISSLQP EDFATYYCQQ
```

```
GNTLPWTFGQ GTKVEIKGGG GSGGGGSGGG

GSGGGGSGGG SEVQLVESGG GLVQPGGSLR

LSCAASGYSF TGYAMNWVRQ APGKGLEWVA

LINPYKGVST YNQKFKDRFT FSVDKSKNTA

YLQMNSLRAE DTAVYYCARS GYYGDSDWYF

DVWGQGTLVT VSSGGGGSEA GVAQSPRYKI

IEKRQSVAFW CNPITGHGTL YWYQQILGQG

PKLLIQFHEN GVVDDSQLPK DRFSAERLKG

VDSTLKIQPA KLEDSAVYLC ASSVDWVGDG

ERQYFGPGTR LLVLEDLKNV FPPEVAVFEP

SEAEISHTQK ATLVCLATGF YPDHVELSWW

VNGKEVHSGV CTDPQPLKEQ PALNDSRYAL

SSRLRVSATF WQDPRNHFRC QVQFYGLSEN

DEWTQDRAKP VTQIVSAEAW GRAD
``` a40b37U28

"a40b37U28" is a binding molecule comprising the TCR "a40b37" alpha chain (SEQ ID NO: 49) described above and a TCR beta chain-anti-CD3 fusion (SEQ ID NO: 74). The beta chain-anti-CD3 fusion sequence (SEQ ID NO: 74) is shown below and comprises the U28 anti-CD3 scFv (SEQ ID NO: 70, italics) described above fused to the TCR "a40b37" beta chain (SEQ ID NO: 53) described above. The TCR beta chain and anti-CD3 scFv sequences are covalently linked via a glycine-serine linker (underlined), designated SEQ ID NO: 72.

```
SEQ ID NO: 74:
AIQMTQSPSS LSASVGDRVT ITCRASQDIR

NYLNWYQQKP GKAPKLLIYY TSRLESGVPS

RFSGSGSGTD YTLTISSLQP EDFATYYCQQ

GNTLPWTFGQ GTKVEIKGGG GSGGGGSGGG

GSGGGGSGGG SEVQLVESGG GLVQPGGSLR

LSCAASGYSF TGYAMNWVRQ APGKGLEWVA

LINPYKGVST YNQKFKDRET FSVDKSKNTA

YLQMNSLRAE DTAVYYCARS GYYGDSDWYF

DVWGQGTLVT VSSGGGGSEA GVAQSPRYKI

IEKRQSVAFW CNPISGHGTL YWYQQILGQG

PKLLIQFHEN GVVDDSQLPK DRFSAERLKG

VDSTLKIQPA KLEDSAVYLC ASSWDWVGDG

ERQYFGPGTR LLVLEDLKNV FPPEVAVFEP

SEAEISHTQK ATLVCLATGF YPDHVELSWW

VNGKEVHSGV CTDPQPLKEQ PALNDSRYAL

SSRLRVSATF WQDPRNHERC QVQFYGLSEN

DEWTQDRAKP VTQIVSAEAW GRAD
``` a58b63U28

"a58b63U28" is a binding molecule comprising the TCR "a58b63" alpha chain (SEQ ID NO: 54) described above and a TCR beta chain-anti-CD3 fusion (SEQ ID NO: 75). The beta chain-anti-CD3 fusion sequence (SEQ ID NO: 75) is shown below and comprises the U28 anti-CD3 scFv (SEQ ID NO: 70, italics) described above fused to the TCR "a58b63" beta chain (SEQ ID NO: 55) described above. The TCR beta chain and anti-CD3 scFv sequences are covalently linked via a glycine-serine linker (underlined), designated SEQ ID NO: 72.

```
SEQ ID NO: 75:
AIQMTQSPSS LSASVGDRVT ITCRASQDIR NYLNWYQQKP

GKAPKLLIYY TSRLESGVPS RFSGSGSGTD YTLTISSLQP

EDFATYYCQQ GNTLPWTFGQ GTKVEIKGGG GSGGGGSGGG

GSGGGGSGGG SEVQLVESGG GLVQPGGSLR LSCAASGYSF

TGYAMNWVRQ APGKGLEWVA LINPYKGVST YNQKFKDRFT

FSVDKSKNTA YLQMNSLRAE DTAVYYCARS GYYGDSDWYF

DVWGQGTLVT VSSGGGGSEA GVAQSPRYKI IEKRQSVAFW

CNPISGHGTL YWYQQILGQG PKLLIQFHEE GVVDDSQLPK

DRFSAERLKG VDSTLKIQPA KLEDSAVYLC ASSVDWVGDG

ERQYFGPGTR LLVLEDLKNV FPPEVAVFEP SEAEISHTQK

ATLVCLATGF YPDHVELSWW VNGKEVHSGV CTDPQPLKEQ

PALNDSRYAL SSRLRVSATF WQDPRNHERC QVQFYGLSEN

DEWTQDRAKP VTQIVSAEAW GRAD
``` a61b68U28

"a61 b68U28" is a binding molecule comprising the TCR "a61 b68" alpha chain (SEQ ID NO: 56) described above and a TCR beta chain-anti-CD3 fusion (SEQ ID NO: 75). The beta chain-anti-CD3 fusion sequence (SEQ ID NO: 76) is shown below and comprises the U28 anti-CD3 scFv (SEQ ID NO: 70, italics) described above fused to the TCR "a61b68" beta chain (SEQ ID NO: 57) described above. The TCR beta chain and anti-CD3 scFv sequences are covalently linked via a glycine-serine linker (underlined), designated SEQ ID NO: 72.

```
SEQ ID NO: 76:
AIQMTQSPSS LSASVGDRVT ITCRASQDIR

NYLNWYQQKP GKAPKLLIYY TSRLESGVPS

RFSGSGSGTD YTLTISSLQP EDFATYYCQQ

GNTLPWTFGQ GTKVEIKGGG GSGGGGSGGG

GSGGGGSGGG SEVQLVESGG GLVQPGGSLR

LSCAASGYSF TGYAMNWVRQ APGKGLEWVA

LINPYKGVST YNQKFKDRFT FSVDKSKNTA

YLQMNSLRAE DTAVYYCARS GYYGDSDWYF

DVWGQGTLVT VSSGGGGSEA GVAQSPRYKI

IEKGQSVAFW CNPISGHGTL YWYQQILGQG

PKLLIQFHEN GVVDDSQLPK DRFSAERLKG

VDSTLKIQPA KLEDSAVYLC ASSVDWVGDG
```

```
             ERQYFGPGTR LLVLEDLKNV FPPEVAVFEP

SEAEISHTQK ATLVCLATGF YPDHVELSWW

VNGKEVHSGV CTDPQPLKEQ PALNDSRYAL

SSRLRVSATF WQDPRNHERC QVQFYGLSEN

DEWTQDRAKP VTQIVSAEAW GRAD
``` a67b72U28

"a67b72U28" is a binding molecule comprising the TCR "a67b72" alpha chain (SEQ ID NO: 58) described above and a TCR beta chain-anti-CD3 fusion (SEQ ID NO: 77). The beta chain-anti-CD3 fusion sequence (SEQ ID NO: 77) is shown below and comprises the U28 anti-CD3 scFv (SEQ ID NO: 70, italics) described above fused to the TCR "a67b72" beta chain (SEQ ID NO: 59) described above. The TCR beta chain and anti-CD3 scFv sequences are covalently linked via a glycine-serine linker (underlined), designated SEQ ID NO: 72.

```
SEQ ID NO: 77:
AIQMTQSPSS LSASVGDRVT ITCRASQDIR

NYLNWYQQKP GKAPKLLIYY TSRLESGVPS

RFSGSGSGTD YTLTISSLQP EDFATYYCQQ

GNTLPWTFGQ GTKVEIKGGG GSGGGGSGGG

GSGGGGSGGG SEVQLVESGG GLVQPGGSLR

LSCAASGYSF TGYAMNWVRQ APGKGLEWVA

LINPYKGVST YNQKFKDRFT FSVDKSKNTA
```

```
             YLQMNSLRAE DTAVYYCARS GYYGDSDWYF

DVWGQGTLVT VSSGGGGSEA GVAQSPRYKI

IEKGQSVAFW CNPISGHGTL YWYQQILGQG

PKLLIQFHEE GVVDDSQLPK DRFSAERLKG

VDSTLKIQPA KLEDSAVYLC ASSVDWVGDG

ERQYFGPGTR LLVLEDLKNV FPPEVAVFEP

SEAEISHTQK ATLVCLATGF YPDHVELSWW

VNGKEVHSGV CTDPQPLKEQ PALNDSRYAL

SSRLRVSATF WQDPRNHERC QVQFYGLSEN

DEWTQDRAKP VTQIVSAEAW GRAD
``` a40b23U28-mol93

"a40b23U28-mol93" is the a40b23U28 binding molecule in a single-chain format and with an Fc half-life extending domain. From the N- to the C-terminus, the molecule comprises the U28 anti-CD3 scFv (SEQ ID NO: 70, italics), a glycine-serine linker (SEQ ID NO: 72, underlined), the b23 TCRβ chain sequence (double underlined, plain text) comprising the b23 variable domain (SEQ ID NO: 36) described above and the constant domain with reduced glycosylation (SEQ ID NO: 117), a glycine-serine linker (SEQ ID NO: 85, underlined, italics), a Fc hinge region (SEQ ID NO: 94, bold italics), a first Fc domain (SEQ ID NO: 95, plain text), a glycine-serine linker (SEQ ID NO: 85, underlined, italics), the a40 TCRα chain sequence (double underlined, bold text) comprising the a40 variable domain (SEQ ID NO: 28) described above and the constant domain with reduced glycosylation (SEQ ID NO: 116), a glycine-serine linker (SEQ ID NO: 85, underlined, italics), a Fc hinge region (SEQ ID NO: 94, bold italics), and a second Fc domain (SEQ ID NO: 96, bold text).

```
SEQ ID NO: 93:
AIQMTQSPSS LSASVGDRVT ITCRASQDIR NYLNWYQQKP GKAPKLLIYY TSRLESGVPS

RFSGSGSGTD YTLTISSLQP EDFATYYCQQ GNTLPWTFGQ GTKVEIKGGG GSGGGGSGGG

GSGGGGSGGG SEVQLVESGG GLVQPGGSLR LSCAASGYSF TGYAMNWVRQ APGKGLEWVA

LINPYKGVST YNQKFKDRFT FSVDKSKNTA YLQMNSLRAE DTAVYYCARS GYYGDSDWYF

DVWGQGTLVT VSSGGGGSEA GVAQSPRYKI IEKRQSVAFW CNPISGHGTL YWYQQILGQG

PKLLIQFHEN GVVDDSQLPK DRFSAERLKG VDSTLKIQPA KLEDSAVYLC ASSVDWVGDG

ERQYFGPGTR LLVLEDLKNV FPPEVAVFEP SEAEISHTQK ATLVCLATGF YPDHVELSWW

VNGKEVHSGV CTDPQPLKEQ PALQDSRYAL SSRLRVSATF WQDPRNHERC QVQFYGLSEN

DEWTQDRAKP VTQIVSAEAW GRADGGGSGG GGEPKSSDKT HTCPPCPAPE LLGGPSVFLF

PPKPKDTLMI SRTPEVTCVV VDVSHEDPEV KFNWYVDGVE VHNAKTKPRE EQYGSTYRVV

SVLTVLHQDW LNGKEYKCKV SNKALPAPIE KTISKAKGQP REPQVYTLPP SRDELTKNQV

SLSCAVKGFY PSDIAVEWES NGQPENNYKT TPPVLDSDGS FFLVSKLTVD KSRWQQGNVF

SCSVMHEALH NHYTQKSLSL SPGKGGGSGG GGLAKTTQPI SMDSYEGQEV NITCSHNYIA

ANDFITWYQQ FPSQGPRFFI QGYKINVQNE VASLFIPADR KSSTLSLPRV SLSDTAVYYC

LAWGGTDLLP FGTGTRLQVF PNIQNPDPAV YQLRDSKSSD KSVCLFTDED SQTQVSQSKD

SDVYITDKCV LDMRSMDFKS NSAVAWSQKS DFACANAFQN SIIPEDTGGG SGGGGEPKSS

DKTHTCPPCP APELLGGPSV FLFPPKPKDT LMISRTPEVT CVVVDVSHED PEVKFNWYVD
```

-continued

```
GVEVHNAKTK PREEQYGSTY RVVSVLTVLH QDWLNGKEYK CKVSNKALPA PIEKTISKAK

GQPREPQVYT LPPSRDELTK NQVSLWCLVK GFYPSDIAVE WESNGQPENN YKTTPPVLDS

DGSFFLYSKL TVDKSRWQQG NVFSCSVMHE ALHNHYTQKS LSLSPGK
```

Exemplary Amino Acid Linker Sequences

```
                                              (SEQ ID NO: 72)
GGGGS, (SEQ ID NO: 78)
GGGSG, (SEQ ID NO: 79)
GGSGG, (SEQ ID NO: 80)
GSGGG, (SEQ ID NO: 81)
GSGGGP, (SEQ ID NO: 82)
GGEPS, (SEQ ID NO: 83)
GGEGGGP, (SEQ ID NO: 84)
GGEGGGSEGGGS, (SEQ ID NO: 85)
GGGSGGGG, (SEQ ID NO: 86)
GGGGSGGGGSGGGGSGGGGSGGGS, (SEQ ID NO: 87)
GGGGSGGGGSGGGGSGGGGS, (SEQ ID NO: 88)
EAAAK
and (SEQ ID NO: 89)
EAAAKEAAAKEAAAK.
```

Additional Mutated Alpha Chain Variable Domains

```
a6
                                              (SEQ ID NO: 90)
LAKTTQPISM DSYEGQEVNI TCSHNHIAAN

DFITWYQQFP SQGPRFFIQG YKTNVSNEVA

SLFIPADRKS STLSLPRVSL SDTAVYYCLA

WGGTDMLIFG TGTRLQVFP
```

Additional Mutated Beta Chain Variable Domains

```
b6
                                              (SEQ ID NO: 91)
EAGVAQSPRY KIIEKRQSVA FWCNPISGHG TLYWYQQILG

QGPKLLIQFH NNGVVDDSQL PKDRFSAERL KGVDSTLKIQ

PAKLEDSAVY LCASSLDWVG DGERQYFGPG TRLLVL
```

```
b3
                                              (SEQ ID NO: 92)
EAGVAQSPRY KIIEKRQSVA FWCNPIAGHG TLYWYQQILG

QGPKLLIQFH ENRVVDDSQL PKDRFSAERL KGVDSTLKIQ

PAKLEDSAVY LCASSLDWVG SGETQYFGPG TRLLVL
```

Constant Domain Sequences with Reduced Glycosylation

Alpha chain constant domain with three N to Q mutations

```
                                              (SEQ ID NO: 116)
NIQNPDPAVY QLRDSKSSDK SVCLFTDFDS QTQVSQSKDS

DVYITDKCVL DMRSMDFKSN SAVAWSQKSD FACANAFQNS IIPEDT
```

Beta Chain Constant Domain with One N to Q Mutation

```
                                              (SEQ ID NO: 117)
EDLKNVEPPE VAVFEPSEAE ISHTQKATLV CLATGFYPDH

VELSWWVNGK EVHSGVCTDP QPLKEQPALQ DSRYALSSRL

RVSATFWQDP RNHFRCQVQF YGLSENDEWT QDRAKPVTQI

VSAEAWGRAD
```

Figure 8:
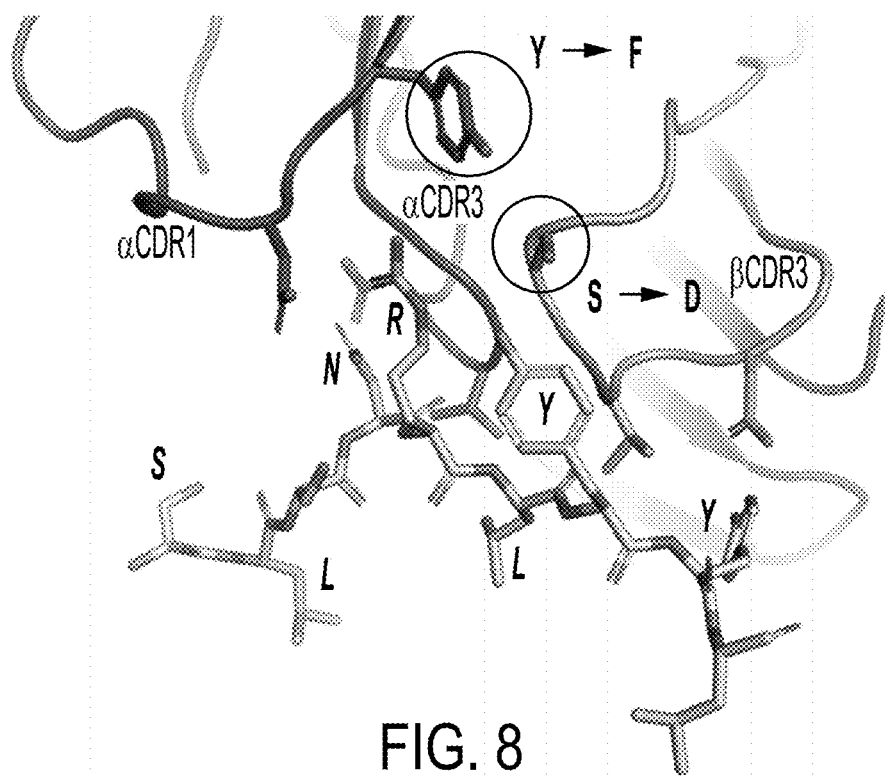
FIG. 8: image of an x-ray crystal structure model of the TCR-peptide interface formed by the TCR "S8" when bound to SLSNRLYYL (SEQ ID NO: 1) in complex with HLA-A*02. Key residue changes introduced during affinity maturation are indicated.

TCR CDR Amino Acid Residues Critical for Binding to the SLSNRLYYL (SEQ ID NO: 1) HLA-A*02 Complex The structure of the TCRs "S8" and variant "a67b72" bound to SLSNRLYYL (SEQ ID NO: 1) in complex with HLA-A*02 (described in Example 7 and shown in FIGS. 8 and 9) were used to determine amino acid sequences of CDRs that confer specific binding of the TCR to the pHLA complex based on the key CDR residues contacting the peptide in the complex. In the following tables, "X" represents any amino acid. The forward slash ("/") represents "or", e.g. "S/T" indicates that the amino acid can be S (Ser) or T (Thr) at the specified position in the sequence.

TCR Alpha Chain CDR 1 Sequences:

| | Sequence | | | | | | |
|---|---|---|---|---|---|---|---|
| SEQ ID NO | 1 | 2 | 3 | 4 | 5 | 6 | 7 |
| 98 | X | X | X | X | N | X | Y/F |
| 99 | Y/N | X | X | A/T | N | X | Y/F |
| 100 | Y/N | I/V/L | A/G | A/T | N | D/E | Y/F |
| 101 | Y | I/V/L | A/G | A | N | D/E | F |

TCR Alpha Chain CDR 2 Sequences:

| SEQ ID NO | 1 | 2 | 3 | 4 | 5 |
|---|---|---|---|---|---|
| 102 | G/A | Y/W/F | K/R/H | T/S | N/K |
| 103 | G/A | Y/W/F | K/R/H | T/S | N |

TCR Alpha Chain CDR 3 Sequences:

| SEQ ID NO | 1 | 2 | 3 | 4 | 5 | 6 | 7 | 8 | 9 | 10 |
|---|---|---|---|---|---|---|---|---|---|---|
| 104 | X | X | X | G | G | T | D | X | X | X |
| 105 | X | X | X | G | G | T | D | K/V/L | X | I/P |
| 106 | V/I/L | A/G | Y/W/F | G | G | T | D | K/V/L | V/I/L | I/P |
| 107 | V/I/L | A/G | Y/W/F | G | G | T | D | L | V/I/L | P |

TCR Beta Chain CDR 1 Sequences:

| SEQ ID NO | Sequence | | | | |
|---|---|---|---|---|---|
| | 1 | 2 | 3 | 4 | 5 |
| 108 | S/T | A/G | K/R/H | A/G | S/T |
| 109 | S | A/G | K/R/H | G | S/T |

| SEQ ID NO | Sequence | | | | | |
|---|---|---|---|---|---|---|
| | 1 | 2 | 3 | 4 | 5 | 6 |
| 110 | Y/W/F | H/Q | N/E | N/E | A/G | V/I/L |
| 111 | Y/W/F | H | E | E | A/G | V/I/L |

| SEQ ID | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 112 | X | X | X | X | D | X | V | G | S/D | X | X | X | X | X |
| 113 | A/G | S/T | S/T | V/L | D | Y/W/F | V | G | S/D | A/G | D/E | R/T | Q/N | Y/W/F |
| 114 | A/G | S/T | S/T | V | D | Y/W/F | V | G | S/D | A/G | D/E | R | Q/N | Y/W/F |
| 115 | A/G | S/T | S/T | V | D | Y/W/F | V | G | D | A/G | D/E | R | Q/N | Y/W/F |

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the purview of this application and scope of the appended claims.

Example 1—Expression of PIWIL in Cancers

PIWIL and PIWIL-like proteins are known to be involved in oncogenic processes, such as cell renewal, cell migration, and cell invasion, and in disease progression. Overexpression of PIWIL has been associated with various tumour types, and PIWIL expression has been linked to poor prognosis in colorectal and gastric cancers (Dong et al. (2021), Critical Roles of PIWIL1 in Human Tumours: Expression, Functions, Mechanisms, and Potential Clinical Implications, Front. Cell Dev. Biol., 9:1-11, doi.org/10.3389/fcell.2021.656993; Gao, et al. (2018) PIWI-like protein 1 upregulation promotes gastric cancer invasion and metastasis. Onco Targets Ther. 11, 8783-8789. doi: 10.2147/OTT.S186827).

Publicly available PIWIL1 mRNA expression data obtained from The Cancer Genome Atlas (TCGA; http://cancergenome.nih.gov/) showed a relatively higher frequency of PIWIL expression in colon cancer, particularly in the microsatellite instability high (MSI) subset, as well as in the BRAF mutation subset, with expression also shown in esophageal and gastric tumours. Gene expression values for the TCGA dataset are normalised by FPKM (Fragments Per Kilobase of transcript per Million mapped reads). PIWIL1 expression was also assessed in samples by routine quantitative reverse transcription PCR (RTqPCR) methods. The RTqPCR results demonstrate validation of frequencies observed from the TCGA dataset. Exemplary frequency values are shown in the Table below:

| Indications | TCGA n total | TCGA (RNA-seq) ≥ 1FPKM | TCGA (RNA-seq) ≥ 5FPKM | RTqPCR n total | RTqPCR ≥ 5000tr/100ng RNA |
|---|---|---|---|---|---|
| Colon | 471 | 28% | 12% | 109 | 39% |
| Colon, MSI high | 39 | 69% | 56% | 22 | 45% |
| Oesophageal | 89 | 33% | 8% | 21 | 38% |
| Gastric | 416 | 23% | 9% | 52 | 21% |

| Indications | TCGA n total | TCGA (RNA-seq) ≥ 1FPKM | TCGA (RNA-seq) ≥ 5FPKM | RTqPCR n total | RTqPCR ≥ 5000tr/100ng RNA |
|---|---|---|---|---|---|
| Gastric, MSI high | 78 | 38% | 18% | NA | NA |
| Pancreatic | 178 | 6% | 1% | 65 | 14% |

PIWIL1 gene expression data was complemented by analyses from a dataset corresponding to a 648-gene next generation sequencing (NGS) panel, TempusxT (https://www.tempus.com/oncology/genomic-profiling/) with full-transcriptome RNA-Seq data. PIWIL1 gene expression was observed within the top 25 most common solid tumour types in the Tempus dataset. Gene expression values are normalised by transcripts-per-million (TPM) and are in units of log 2 transformed (TPM+1). Each single unit increase in expression represents a doubling of gene expression. The Table below shows the frequencies of PIWIL expression in the 10 highest expression cancer types:

| Indications | n | PIWIL expression log2 (TPM + 1) |
|---|---|---|
| Colorectal adenocarcinoma | 15400 | 25.9% |
| Ovarian Serous carcinoma | 3982 | 17.3% |
| Thyroid cancers | 1697 | 28.5% |
| Endometrial carcinoma | 1550 | 10.6% |
| Esophageal carcinoma | 2875 | 23.2% |
| Gastric cancer | 1914 | 16.5% |
| Pancreatic adenocarcinoma | 8435 | 9.2% |
| Small Cell Lung carcinoma | 1208 | 4.6% |
| Cholangiocarcinoma | 3835 | 4% |
| Renal Clear Cell carcinoma | 1566 | 0.2% |

Further analysis of Tempus data showed enrichment of PIWIL expression in small patient subsets of MSI high and BRAF mutants, consistent with TCGA and RTqPCR data, as well as a slightly higher PIWIL1 expression in female patients, and increases of PIWIL1 expression with age. There was no significant correlation of PIWIL1 expression with disease progression.

Immunohistochemistry (IHC) on colon adenocarcinoma tumour samples was also performed. Results of these analyses demonstrated homogenous expression of PIWIL1 in colon adenocarcinoma samples, with expression being retained in metastatic samples. IHC analysis also confirmed enrichment of PIWIL1 expression in MSI-H (microsatellite instability-high) and BRAF mutant subsets.

Example 2—Identification of TCRs Specific for a PIWIL1 Peptide-HLA Complex

To generate soluble potent TCR-anti-CD3 fusion cancer therapeutic proteins (Immune Mobilizing Monoclonal TCRs Against Cancer, or ImmTAC®) targeting PIWIL1, TCR candidates capable of binding to a SLSNRLYYL (SEQ ID NO: 1)-HLA-A*02 complex with high affinity and specificity were first identified. In a first step, sixteen (16) native, or WT, TCR candidates with binding affinities in the low pM range were isolated from T cell clones obtained from human donors, or from native TCR phage libraries. The construction of native TCR phage libraries has been described previously (e.g., in WO 2015/136072, WO 2017/046198 and WO 2017/046201). Chain usage and CDR3 sequences of each native TCR was determined. Next, each native TCR was used as a template to identify TCR mutants with higher affinity binding. Affinity maturation was performed on sixteen (16) series, where each series represented an affinity optimization campaign that started with a native TCR.

Selection of higher affinity TCRs binding to the SLSNR-LYYL (SEQ ID NO: 1)-HLA-A*02 complex was conducted using TCR phage display libraries as previously described (Li et al. (2005), Nat. Biotechnol. 23, 349-354). For each affinity maturation campaign related to a single series, at least two rounds of affinity maturation were typically conducted to iteratively select higher affinity TCR variants. The amino acid sequences of alpha and beta variable domains were then determined.

Soluble versions of the TCRs were produced by fusing variable domains to truncated versions of the respective alpha and beta chain constant domains, and incorporating a non-native interchain disulphide bond between constant domain residues as previously described (WO 2003/020763). Alpha and beta chains were expressed separately in $E.\ coli$ inclusion bodies. Solubilised inclusion bodies containing alpha and beta chain were combined. Refolded TCRs were then purified by anion exchange and size exclusion chromatography using established methods Boulter, et al. (2003), Protein Eng. 16, 707-711; Liddy, et al. (2012), Nature Medicine vol. 18,6: 980-7).

To assess the ability of each native TCR of each series to recognise the target pHLA complex, binding parameters were obtained by Surface Plasmon Resonance (SPR). SPR measurements were carried out on a BIAcore 8K, BIAcore 3000 or BIAcore T200 instrument. Briefly, biotinylated class I HLA-A*02 molecules were refolded with the peptide of interest and purified using available methods (O'Callaghan et al. (1999), Anal Biochem 266(1): 9-15; Garboczi, et al. (1992), Proc Natl Acad Sci USA 89(8): 3429-3433). Biotinylated peptide-HLA monomers were immobilized on to streptavidin-coupled CM-5 sensor chips. Equilibrium binding constants were determined using serial dilutions of soluble TCR. $K_D$ values were obtained by non-linear curve fitting using Prism software and the Langmuir binding isotherm, bound=C*Max/(C+KD), where "bound" is the equilibrium binding in response units at injected TCR concentration C and Max is the maximum binding. Measurements were performed at 25° C., unless otherwise indicated, in Dulbecco's PBS buffer, supplemented with 0.005% P20.

From the sixteen series (16) analysed, TCRs identified from series 8 (S8), with chain pairing corresponding to TRAV4/TRVB11-2, were selected for further optimisation.

The affinity of the soluble native S8 TCR for peptide-HLA complex was determined as 225 nM. To determine the specificity of the native S8 TCR to the target pHLA complex, binding to alternative peptide-HLA-A*02 complexes was assessed by screening a peptide library. One particular peptide, from the protein DOCK11, was identified as a potential mimetic. Positions within DOCK11 that differ from the target PIWIL peptide are show below in bold and underlined.

| Gene | Peptide |
|------|---------|
| DOCK11 | M L D K Y S H Y L |
| PIWIL1 | S L S N R L Y Y L |

The interaction between each native TCR and mimetic peptide was carried out using SPR methods as described above.

The affinity of the native S8 TCR for the mimetic peptide-HLA complex was determined as 1540 nM, indicating an affinity window of 6.8 fold between binding to target and mimetic.

TCR S8 was then used as a template in the first round of affinity maturation to identify TCR variants with higher affinity as previously described (Li et al. (2005), Nat. Biotechnol. 23, 349-354). Briefly, TCR phage libraries were generated using NNK oligonucleotides to generate mutations in the complementarity-determining regions (CDRs). For S8 affinity maturation, negative selection was also incorporated in the first round of affinity maturation.

Negative selection with the mimetic peptide during affinity maturation improved the affinity window with the mimetic peptide. TCR variants identified using negative selection demonstrated an improved specificity profile against antigen negative cells, as determined by the ability of the TCR to drive T cell activation when fused to an anti-CD3 scFv. As shown in FIG. 1, a TCR variant fused to antiCD3 and having an additional mutation identified only with negative selection showed specific binding to an antigen positive cell (Ag+), whereas a TCR variant not having undergone negative selection showed cross-reactivity to antigen negative (Ag−) cells.

From the first round of affinity maturation of the S8 series, the highest affinity TCR variant selected using negative selection (a6b6U) corresponded to one having a $K_d$ of 365 μM. While other TCR variants were identified with comparatively higher binding affinities, they were not as specific and clean with respect to cross-reactivity against Ag-cells, a critical factor in selecting a TCR therapeutic candidate for development.

Figure 2:
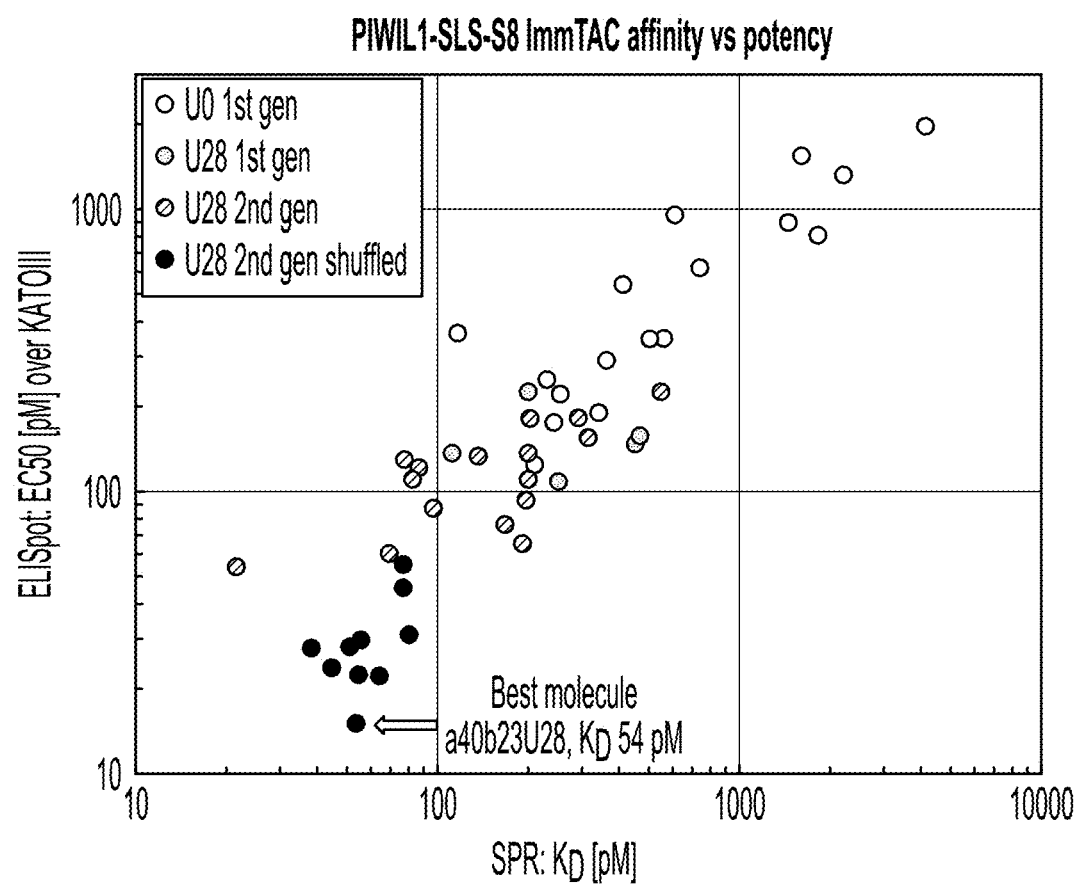
FIG. 2: Plot showing affinity as determined by SPR verses potency as determined by IFNγ release for selected TCR variants obtain during affinity maturation.

Example 3—Identification of Potent High Affinity TCRs Specific for a PIWIL Peptide Additional improvements in TCR affinities were achieved in a second round of affinity maturation where second-generation libraries prepared from TCRs isolated from the first round were used. Combinations of mutated alpha and beta chains from this second round were selected and identified. Subsequent to the second round of selection, an additional (third) round of selection was conducted with libraries generated by shuffling selected CDRs of interest. For example, alpha and beta chains were generated where the three CDRs of alpha chains of interest and three CDRs of beta chains of interest from the first two rounds of affinity maturation, were randomly shuffled to generate new alpha and beta chains. These new alpha and beta chains were utilized in TCR phage display library methods in an additional round of selection. Several of the resulting TCR variants obtained from this additional shuffled library selection generated TCR variants with further enhanced affinity and increased potency in cellular assays, as shown in FIG. 2. The a40b23U28 TCR variant highlighted with an arrow in FIG. 2 had the strongest potency combined with a very high affinity. The a40b23U28 TCR variant was selected for further characterization and optimization.

To assess binding of these TCR variants, soluble TCRs comprising mutated alpha and beta chains were first prepared as bispecific molecules, by fusing an antiCD3 scFv fragment to the N terminus of the TCR beta chain. Binding molecules in this format are ImmTAC® molecules including, for example, tebentafusp, sold under the brand name KIMMTRAK®. Such molecules are referred to as "TCR-anti-CD3 fusion" below. The TCR-anti-CD3 fusion molecules described herein comprise a variant antiCD3 sequence, termed U28 (SEQ ID NO: 70), which has been described previously (WO2020157210)

TCR-anti-CD3 fusion molecules comprising mutated alpha and beta chains were expressed in *E. coli* and purified as previously described. The yield was calculated from the concentration of purified material as determined by absorbance at 280 nm using a Nanodrop spectrophotometer.

Binding to target was assessed by SPR using a similar method as described above. For high affinity interactions, binding parameters were determined by single cycle kinetics analysis. Typically, 60-120 μl (or approx. 240 ul for Biacore 8K instrument) of TCR-anti-CD3 fusion was injected at a top concentration of between 50-100 nM (or 2-50 nM for Biacore 8K instrument), with successive 2 fold dilutions used for the other four injections. The lowest concentration was injected first. To measure the dissociation phase, buffer was injected until ≥10% dissociation occurred, typically after 1-3 hours. Kinetic parameters were calculated using BIAevaluation® software. The dissociation phase was fitted to a single exponential decay equation enabling calculation of half-life. The equilibrium constant KD was calculated from $k_{off}/k_{on}$.

A summary of the binding parameters for selected TCR-antiCD3 fusion molecules is provided in the table below:

| Molecule ID | TRAV (SEQ ID) | TRBV (SEQ ID) | Full alpha chain SEQ ID | Full beta chain SEQ ID | $K_D$ (pM) | $T_{1/2}$ (h) |
|---|---|---|---|---|---|---|
| a6b6U | 90 | 91 | | | 365 | 1.3 |
| a40b23U28 | 28 | 36 | 49 | 119 | 54.0 | 7.1 |
| a36b38U28 | 22 | 42 | 51 | 73 | 67.0 | 7.4 |
| a40b37U28 | 28 | 40 | 49 | 74 | 30.5 | 15.3 |

Binding of a40b23U28 to the mimetic peptide from DOCK11 was additionally assessed and the resulting affinity window was determined to be >5000 fold.

Example 4—Affinity Selected TCR-Anti-CD3 Fusion Molecules Demonstrate Potent and Specific T Cell Activation The TCR anti-CD3 fusion molecules selected and generated from the multiple rounds of affinity maturation as described above were assessed for potency. T cell activation was determined by measuring IFNγ secretion using an ELISpot assay. Assays were performed using a human IFN-γ ELISPOT kit (BD Biosciences) according to the manufacturer's instructions. Peripheral blood mononuclear cells (PBMC), isolated from fresh donor blood, were used as effector cells.

In this example, the following cancer cells lines were used as antigen positive target cells: KATOIII (gastric carcinoma), CL11 (colon carcinoma), COLO201 (colorectal adenocarcinoma), COL0205 (colorectal adenocarcinoma), COLO206F (colorectal adenocarcinoma) as compared to the antigen negative cell NCI-H1755. Data were plotted using PRISM software and $EC_{50}$ values were calculated from the curves.

Figure 3A:
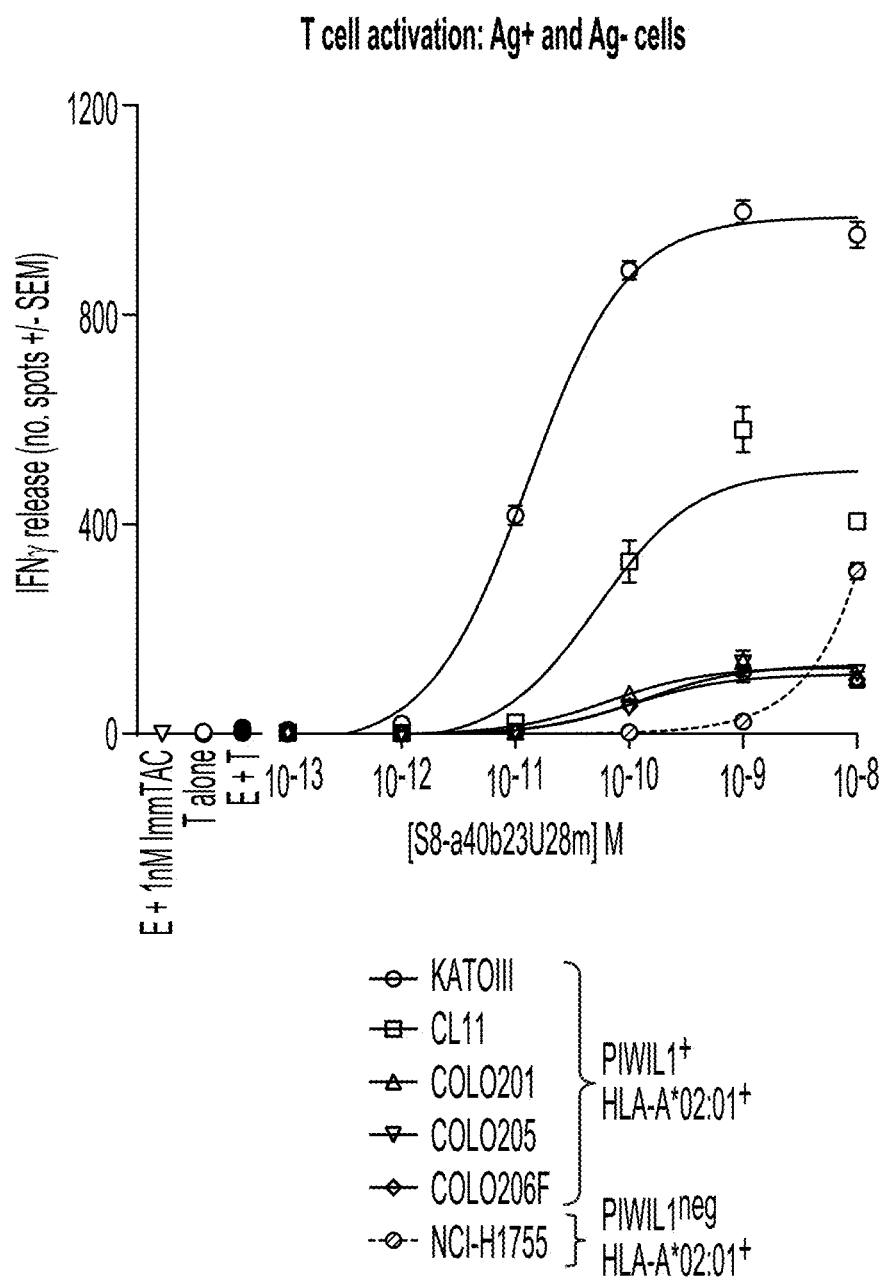
FIG. 3: T cell activation measured by IFNγ release for TCR anti-CD3 fusion molecule a40b23U28 in the presence of (FIG. 3A) antigen positive and antigen negative cancer call lines and (FIG. 3B) normal tissues.

As shown in FIG. 3A, a40b23U28 TCR-anti-CD3 fusion molecule demonstrated good potency in T cell activation assays with IFN-γ release where EC50 values for antigen positive target cells fell in the range between 10 and 200 pM.

EC50 values for three TCR-antiCD3 fusions molecules are provided in the table below:

| Molecule ID | TRAV (SEQ ID) | TRBV (SEQ ID) | Full alpha chain SEQ ID | Full beta chain SEQ ID | Reactivity against antigen positive cell lines (Ec50) | | | | |
|---|---|---|---|---|---|---|---|---|---|
| | | | | | KATOIII | CL11 | COLO201 | COLO205 | COLO206F |
| a40b23U28 | 28 | 36 | 49 | 119 | 12.91 | 52.66 | 65.81 | 130.90 | 102.80 |
| a36b38U28 | 22 | 42 | 51 | 73 | 7.95 | 37.42 | 133.10 | 197.50 | 164.20 |
| a40b37U28 | 28 | 40 | 49 | 74 | 11.47 | 35.75 | 171.10 | 167.70 | 123.90 |

Figure 3B:
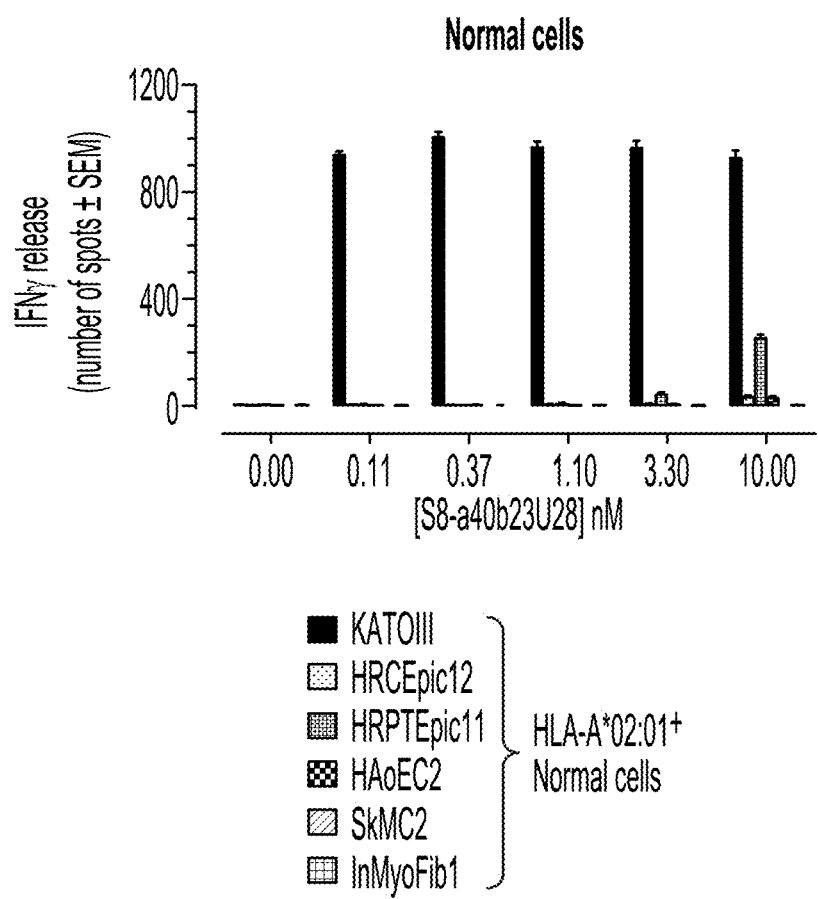

To further determine suitability for therapeutic use, the a40b23U28 TCR-anti-CD3 fusion molecule was tested for non-specific activation in the presence of normal cells derived from healthy human tissues using the same ELISPOT methodology as described above. The panel of normal cells used in this example were derived from pulmonary, cardiac and muscle tissues: (Pulmonary—bronchial epithelial cells $HRCE_{pic12}$ and $HRCE_{pic11}$); cardiac—aortic endothelial cells (HAoEC2); Muscle —skeletal muscle myoblasts (SkMC2) and pulmonary fibroblasts (InMyc-Fib1)). As shown in FIG. 3B, reactivity against these normal cells was not detectable below 3 nM.

In additional studies, no broad release of pro-inflammatory cytokines was observed below 10 nM.

Example 5—Further Optimisations Enhance Manufacturing Yield and Stability while Retaining Other Desirable Therapeutic Properties Additional amino acid substitutions were made in the TCR alpha and beta chain variable domain of the a40 and b23 chains of the a40b23U28 TCR anti-CD3 fusion molecule to improve manufacturability and yield while maintaining affinity, potency and specificity. A methionine cleavage site and deamidation prone residues were identified; one in the alpha chain and one in the beta chain.

To improve cleavage of N term methionine when produced in *E. coli*, it was found that an L1A substitution in the a40 alpha chain was beneficial. In addition, it was found that an N52E substitution in the b23 beta chain reduced the deamidation risk. Incorporation of these mutations improved the yield of the a40b23U28 TCR anti-CD3 fusion molecule by 4-fold. The resulting TCR anti-CD3 fusion molecule was termed a58b63U28.

In parallel, amino acid substitutions were identified that served to increase the thermal stability of the molecule as determined by differential scanning fluorimetry (DSF). Three mutations were identified, two alpha chain mutations and one beta chain mutations which increased the Tm: T21 P and P65S in the alpha chain, based on numbering of a40 (SEQ ID NO: 28), and R16G in the beta chain, based on the numbering of b23 (SEQ ID NO: 36). These mutations were found to increase the Tm by more than 10° C. The resulting TCR anti-CD3 fusion molecule was termed a61 b68U28.

The combination of these mutations was introduced into a40b23U28 to generate a TCR-anti-CD3 fusion molecule referred to as a67b72U28.

Binding

Binding analyses by SPR as described above at both 25° C. and 37° C. with a67b72U28, and the two intermediates (a58b63U28 and a61 b68U28), confirmed that the a67b72U28 TCR anti-CD3 fusion molecule retained pM affinity.

The binding data is provided in the table below:

| | 25° C. | | 37° C. | |
|---|---|---|---|---|
| Molecule ID | $K_D$ | t½ | $K_D$ | t½ |
| a61b68U28 | 60 pM | 6.1 h | nt | nt |
| a58b63U28 | 26 pM | 7.1 h | nt | nt |
| a67b72U28 | 114 pM | 4.3 h | 464 pM | 24 min | nt = not tested

Potency—T Cell Activation

Potency of a67b72U28 was determined in cellular assays. T cell activation was determined by release of interferon-γ (IFNγ) or Granzyme B (GrB) using ELISPOT assays as described above. In each case, peripheral blood mononuclear cells (PBMC), isolated from fresh donor blood, were used as effector cells. The cancer cells lines KATOIII and C11 were used as antigen positive target cells in comparison to the antigen negative cell lines NCI-1755 and IM95. Data were plotted using PRISM software and $EC_{50}$ values were calculated from the curves.

Figure 4A:
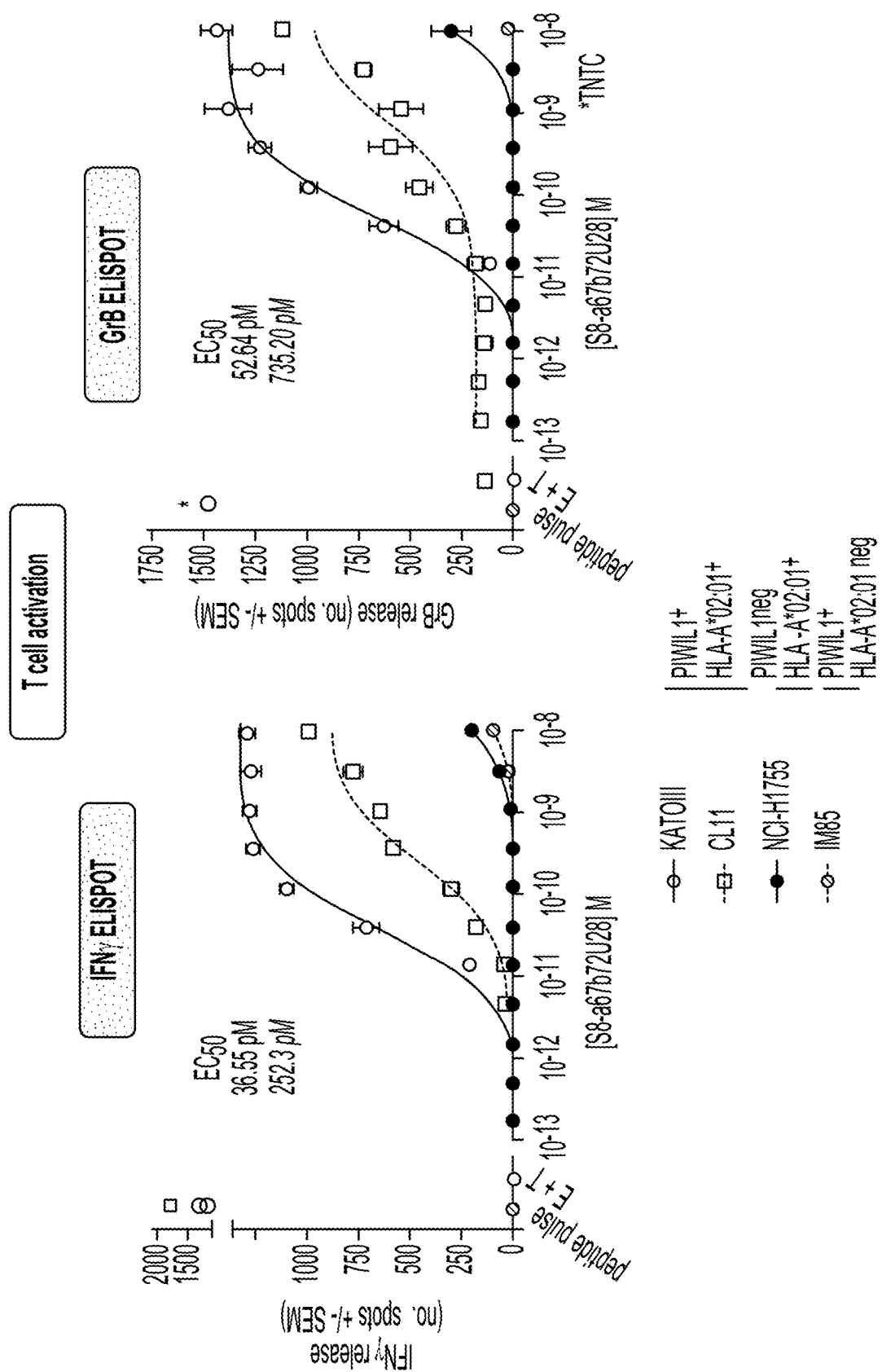
(FIG. 4A) T cell activation measured by IFNγ and GrB release for TCR anti-CD3 fusion molecule a67b72U28 in the presence of antigen positive and antigen negative cancer cell lines.

The resulting T cell activation data are shown in FIG. 4A.

Potency—Cell Killing

Figure 4B:
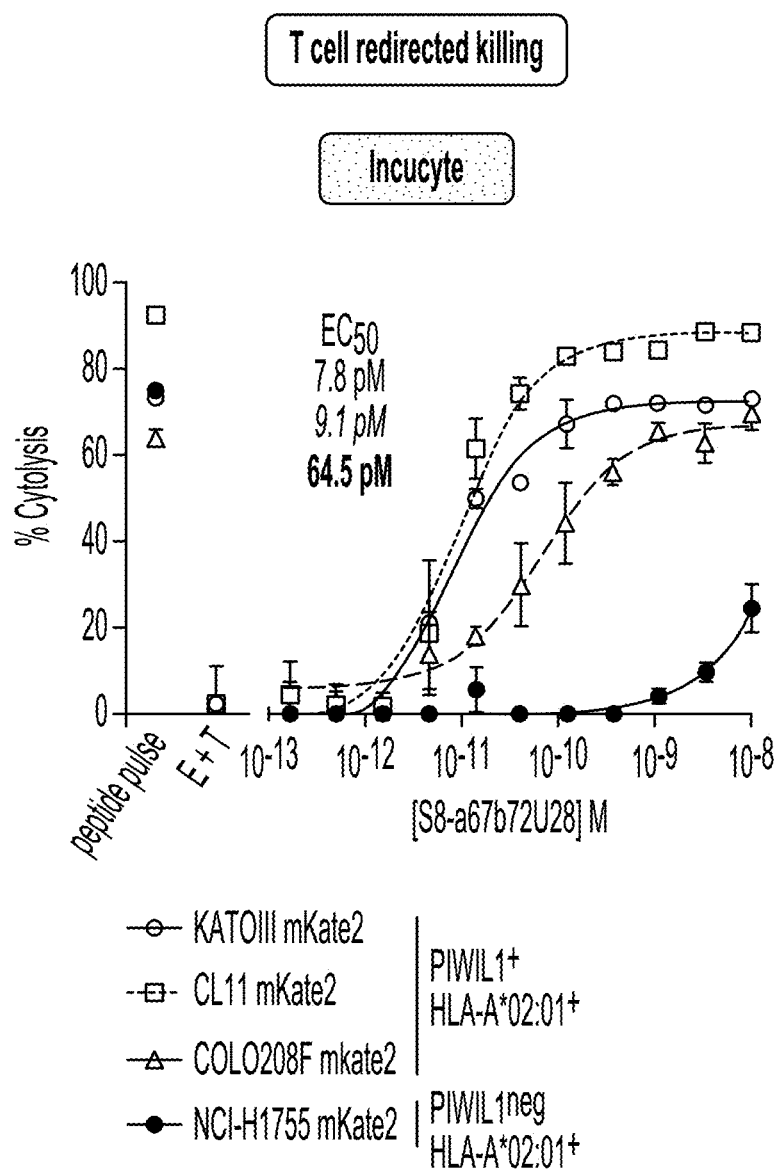
(FIG. 4B) Redirected T cell killing of antigen positive cancer cell lines in with TCR anti-CD3 fusion molecule a67b72U28 using the Incucyte live cell imagining platform with the CellPlayer 96-well Caspase-3/7 apoptosis assay kit.

To determine the ability of the TCR-anti-CD3 fusion molecule a67b72U28 to redirect T cells to kill antigen positive cancer cells, an immune cell killing assay was performed using the Incucyte live cell imagining platform with the CellPlayer 96-well Caspase-3/7 apoptosis assay kit (Essen BioScience, Cat. No. 4440) and carried out according to the manufacturer's instructions. PBMCs were used as effector cells. Tumour cell death was detected utilizing the manufacturer's protocols and reagents by measuring apoptosis with Incucyte® Caspase 3/7 reagent or counting nuclear-labeled cells. The number of apoptotic cells in each image was determined. In all cases, assays were performed in triplicate and measurements were taken every 2 hours over 96 hours. The % cytolysis was calculated at different concentrations of test molecule. In this example the KATOIII (gastric carcinoma), CL11 and COLO206F (colorectal adenocarcinoma) were used as target positive cancer cells. EC50 values were calculated from the curves and are shown in FIG. 4B.

These data demonstrate that the a67b72U28 TCR-anti-CD3 fusion molecule mediates potent activation of T cells and killing of cancer cells, with EC50 values in the low pM range.

Stability and Yield

For the a67b72U28 TCR-anti-CD3 fusion molecule, a representative refold yield of ~17.5 mg/L was obtained from 2×20 L batches. The $T_m$ onset was determined as 50.45° C.

In total, these data confirm that TCR-anti-CD3 fusion molecules of the invention have desirable therapeutic properties.

Example 6—Multidomain Single Chain Binding Molecules Targeting a PIWIL1 Peptide-MHC Complex Demonstrate Potent and Specific T Cell Activation A multi-domain single-chain binding molecule was designed comprising a pMHC binding domain targeting a PIWIL1 peptide (SLSNRLYYL, SEQ ID NO: 1)-MHC complex. The full sequence of the resulting molecule, termed "a40b23U28-mol93", is provided in SEQ ID NO: 93. The TCRα variable and TCRβ variable domains of a40b23U28-mol93 correspond to SEQ ID NOs: 28 ("a40") and 36 ("b23"), respectively.

In the format of the multi-domain binding molecule, as shown in FIG. 5a, the U28 scFv ("TCE-VL" & "TCE-VH") is linked, via a linker, to the N terminus of the TCRβ chain variable domain which is linked to the TCRβ chain constant domain (together "VC1"). The TCRβ chain constant domain is linked at its C terminus via a linker to the N terminus of a first IgG Fc domain ("FC1"), which is linked at its C terminus via a linker to the N terminus of TCRα chain variable domain. The TCRα chain constant domain is linked at its C terminus via a linker to the N terminus of a second IgG Fc domain ("FC2"). Each domain is linked covalently in a single polypeptide chain. The format—referred to a "Mol93"—is as disclosed in U.S. Patent Application No. 63/371,861 filed on 18 Aug. 2022, the contents of which are hereby incorporated by reference.

As shown in FIG. 5b, the variable light and variable heavy chains of U28 dimerise to form the anti-CD3 scFv, the TCRa and TCRb chains dimerise to form a pMHC binding region and the first second IgG Fc domains dimerise to form a half-life extending region.

Expression a40b23U28-mol93 was expressed in Cho cells using the Thermo ExpiCHO™ transient expression protocol. Briefly, cultured cells were diluted to a concentration of 6×10⁶ prior to transfection. Cells were harvested on day 14 post transfection, with temperature shift to 32° C. at day 1 post transfection. Feed additions were performed on day 1 and day 5 post transfection. Clarification was performed with two successive centrifugation steps, at 300×g and 17,500×g. The resulting supernatant was passed through 0.45 μm and 0.2 μm membrane filters.

Purification

Clarified supernatant was purified by Protein A followed by size exclusion chromatography steps. A 15 cm bed height MabSelect Extra Protein A resin column was prepared. The column was loaded with 50 column volumes of supernatant with elution using a sodium citrate buffer at pH 3.0. Eluted product was neutralised with the addition of 2M Tris after three column volumes had been collected and filtered through a 0.2 μm membrane filter. Protein A eluate was concentrated using tangential flow filtration (Pellicon® XL50 with Ultracel® 30 kDa Membrane) to at least 2 mg/mL before loading on to a HiLoad 26/600 Superdex SEC resin. The column was loaded at 5% column volume. Product was eluted into phosphate citrate buffer, with relevant fractions filtered through a 0.22 μm membrane filter.

Binding

Binding of a40b23U28-mol93 to the SLSNRLYYL (SEQ ID NO: 1)-HLA-A*02 complex was determined using SPR as described in Examples 2 and 3 above. The binding affinity ($K_D$) was 50 pM and the binding half life (t1/2) was 11.8 hours. These results were comparable to the equivalent a40b23U28 TCR-antiCD3 fusion molecule without the half-life extending (i.e. Fc) domain, which has binding affinity ($K_D$) of 54 pM and a binding half life (t1/2) of 7.1 hours.

The ability of a40b23U28-mol93 to drive T cell activation was determined by measuring IFNγ secretion using an ELISpot assay. Assays were performed using a human IFN-γ ELISPOT kit (BD Biosciences) according to the manufacturer's instructions. Peripheral blood mononuclear cells (PBMC), isolated from fresh donor blood, were used as effector cells. In this assay KATOIII (gastric carcinoma) and CL11 (colon carcinoma) were used as antigen positive target cells. NCI-H1755 was used as antigen negative cells. Data were plotted using PRISM software and $EC_{50}$ values were calculated from the curves.

Figure 6:
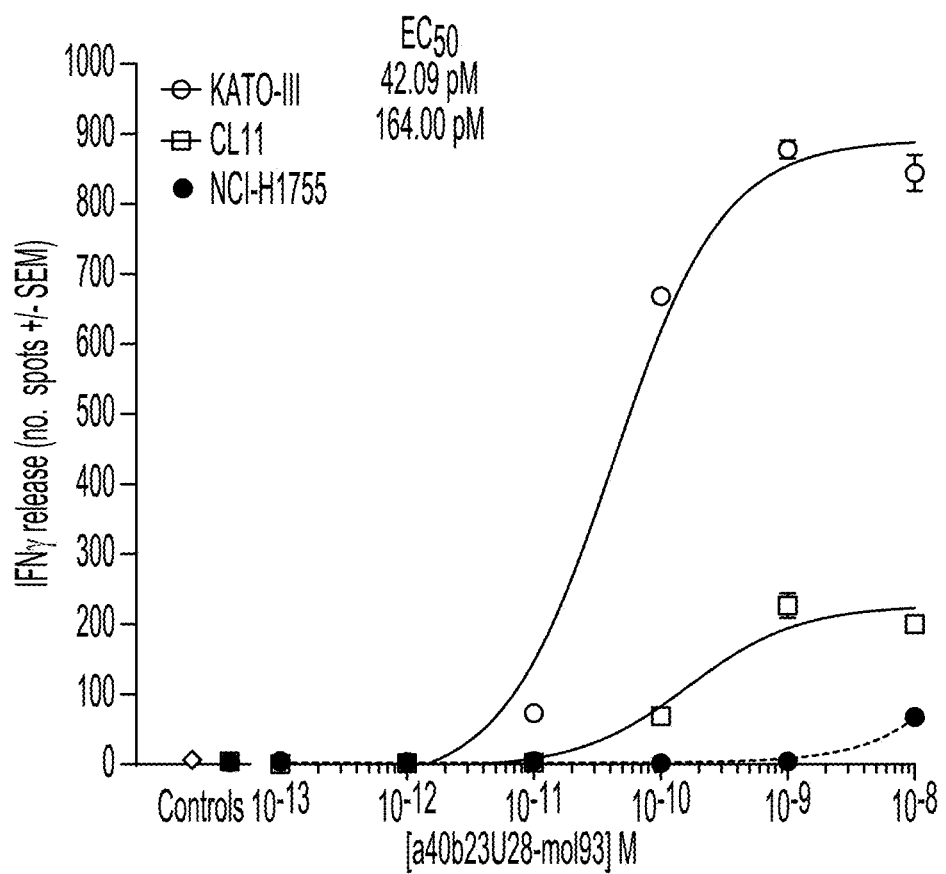
FIG. 6: T cell activation measured by IFNγ release for TCR anti-CD3 fusion molecule a40b23U28-mol93 in the presence of antigen positive and antigen negative cancer cell lines.

FIG. 6 shows that a40b23U28-mol93 gave an $EC_{50}$ value in the low pM range against the two antigen positive cells lines (42.1 μM for KATO-III and 164.0 μM for CL11), and little to no response (at concentrations of a40b23U28-mol93 less than 1 nM) in the presence of antigen negative cells. The equivalent TCR-antiCD3 fusion molecule without the half-life extending (i.e., Fc) domain (a40b23U28) had an EC50 of 12.9 pM and 52.7 pM for KATO-III and CL11 cells respectively, as shown in the table in Example 4.

These data demonstrate that multi-domain single-chain binding molecules of the invention comprising a pMHC binding region targeting a PIWIL1 peptide-MHC complex retain comparable high affinity and potency to the equivalent TCR-antiCD3 fusion molecule without the half-life extending (i.e. Fc) region and retain specificity towards antigen positive cells.

Figure 7:
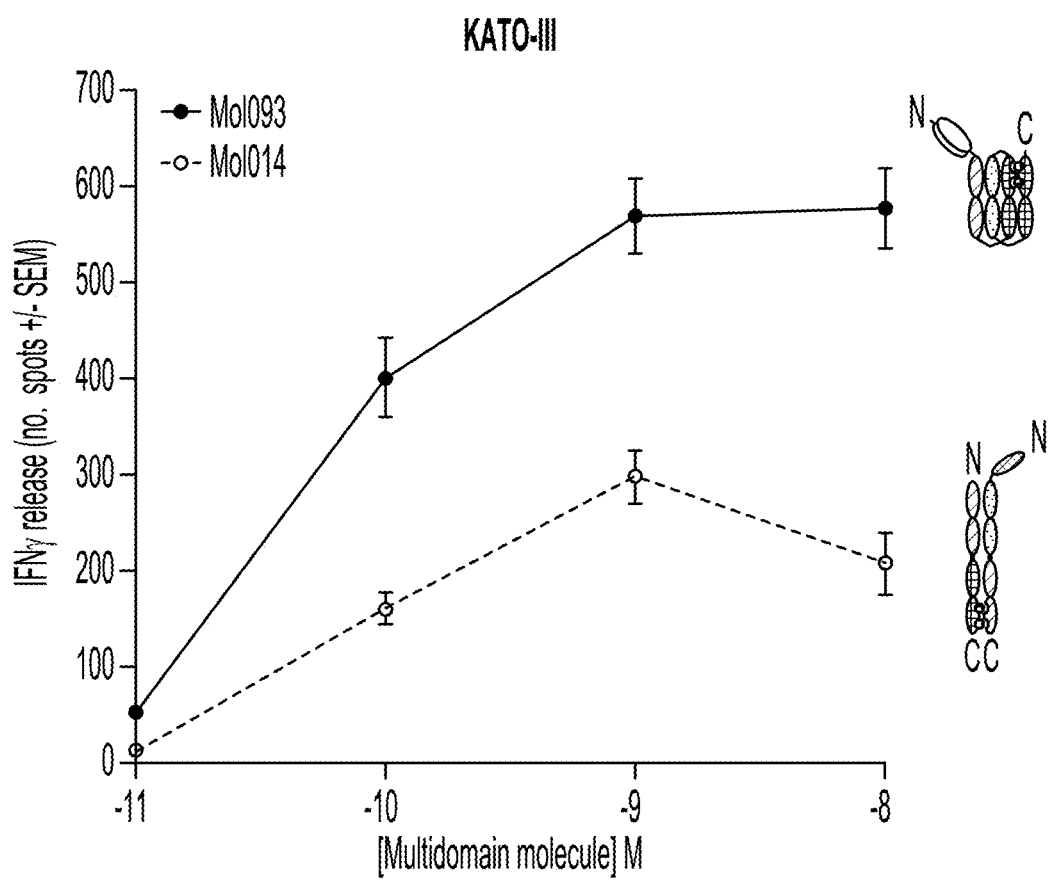
FIG. 7: T cell activation measured by IFNγ release for half-life extended TCR anti-CD3 fusion molecules a40b23U28-mol93 and a40b23U28-mol14 in the presence of antigen positive cells.

In a further experiment, a40b23U28-mol93 was compared to an alternative multi-domain molecule format, termed a40b23U28-mol14. a40b23U28-mol14 has the same individual domain amino acid sequences as a40b23U28-mol93, except it is arranged in a two-chain format as depicted in FIG. 7. In this two-chain format, the first (left hand chain in FIG. 7) comprises, in the N- to C-terminal direction, a TCR alpha chain variable domain, a TCR alpha chain constant domain and an Fc domain. The second chain (right hand chain in FIG. 7) comprises, in the N- to C-terminal direction, an anti-CD3 scFv, a TCR beta chain variable domain, a TCR beta chain constant domain and an Fc domain.

T cell activation against the KATOIII cell line was compared between the two molecules. As shown in FIG. 7, both molecules drive T cell activation. However, Mol93 gives a more potent response than Mol14.

The results described in this Example demonstrate that the multi-domain single-chain format was effective at extending half-life (via provision of the Fc region) without significantly affecting affinity for the target or potency of T cell activation.

Example 7—Structural Analysis of TCR-pHLA Binding Mode

Structural analysis of the S8 TCR bound to SLSNRLYYL (SEQ ID NO: 1) HLA-A*02 complex was performed using X-ray crystallography. Unique features that confer potency and specificity were identified.

Methods

X-ray crystallography. Crystals were grown by vapor diffusion via the sitting drop technique using the MRC 2-well crystallisation plates. 150 nL of 10 to 15 mg/mL TCR-pHLA complex (mixed at a 1:1.1 molar ratio) was added to 150 nL of reservoir solution using the Gryphon dispensing robot (Art Robbins). The plates were then incubated at 20° C. and imaged using ROCK IMAGER 1000 (Formulatrix). Crystals selected for further analysis were cryoprotected with 30% ethylene glycol and then flash-cooled in liquid nitrogen. Diffraction data were collected at several different beamlines at the Diamond Light Source (Didcot, UK) and processed through xia2 DIALS (Winter (2010). J Appl Crystallogr. 43, 186-190, Winter et al. (2018). Acta Crystallogr Sect D Struct Biology. 74, 85-97) or xia2 3dii (Kabsch (2010). Acta Crystallogr Sect D Biological Crystallogr. 66, 125-132) or autoPROC (Vonrhein et al. (2011). Acta Crystallogr Sect D Biological Crystallogr. 67, 293-302) automated pipelines. TCR-pHLA complex structures were solved by molecular replacement using Phaser (McCoy et al. (2007). J. Appl. Crystallogr. 40, 658-674), models built using Coot (Emsley et al. (2010). Acta Crystallogr Sect D Biological Crystallogr. 66, 486-501), and refined using refmac (Kovalevskiy et al. (2018). Acta Crystallogr. Sect. D, Struct. Biol. 74, 215-227), all within the CCβ4 suite (Agirre et al. (2023). Acta Crystallogr. Sect. D, Struct. Biol. 79, 449-461). Molecular replacement search models were identified as follows: for the different TCR molecules, the PDB was searched for structures of proteins with high sequence similarity to alpha and beta sequences separately and these were used as models. For HLA-A2-B2m, the PDB 6RPA (TCR removed) was used. For computational modelling of TCR referred to herein as "a67b72", Molecular Operating Environment (MOE) package (version 2022.02, Chemical Computing Group ULC, Canada) was used with "S8" TCR as template and refined using Quick-Prep.

TCR docking geometry angle calculations: The calculation of the following angles was adopted from Rudolph et al. (2006). Annu Rev Immunol. 24, 419-466.

a. Crossing angle. This angle was calculated by generating two vectors: an HLA groove vector and a TCR cystine vector (or "TCR interdomain vector"). The HLA groove vector follows the two parallel HLA helices with the direction N-terminus to C-terminus of HLA helix 1 and passing through the HLA centroid.

The TCR cystine vector (or "TCR interdomain vector") connects the characteristic cystines (i.e., the intrachain disulfide bonds) in the two variable regions and points from the intrachain disulfide bond in the alpha chain variable region to the intrachain disulfide bond in the beta chain variable region. The crossing angle was defined by the angle between the TCR cystine vector and the HLA groove vector.

b. Tilt angle. The TCR symmetry vector represents the pseudo-two-fold symmetry axis of the TCR variable subunits and points in direction of its CDRs and passes through the TCR centroid. The tilt angle was calculated between the TCR symmetry axis and the HLA groove vector.

c. Roll angle. A second HLA vector (HLA v2) was generated perpendicular to the HLA groove vector and points from HLA helix 1 to HLA helix 2. The two vectors meet at the centroid of the HLA helices. The roll angle was calculated between HLA v2 and the TCR symmetry vector.

Interaction analysis. Residues between TCR and pHLA were identified to be in contact if the distance measurement between any atom from a TCR residue was within or equal to 4.1 Å to any atom from a peptide or an HLA residue.

Results

The crystal structure showed that the S8 TCR bound to the cognate pHLA (i.e., a SLSNRLYYL (SEQ ID NO: 1) HLA-A*02 complex) with a crossing angle of approximately 63°. Three of the six CDRs (αCDR1 αCDR3 and βCDR3) directly interacted with the SLSNRLYYL (SEQ ID NO: 1) peptide and made contacts to the peptide residues in positions 4 to 8. The following tables provide a summary of buried surface area and binding geometry calculations for the interaction between the S8 TCR and SLSNRLYYL (SEQ ID NO: 1) HLA-A*02 complex.

| Buried surface area (BSA) | | | | |
|---|---|---|---|---|
| Chains | TCR on Peptide | TCR on HLA | TCR on HLA helix 1 | TCR on HLA helix2 |
| Alpha chain [%] | 44.8 | 43.8 | 31.3 | 80.5 |
| Beta chain [%] | 55.2 | 56.2 | 68.7 | 19.5 |
| Total BSA [Å$^2$] | 335.4 | 980.1 | 411.8 | 469.6 |

| Binding geometry angles | | |
|---|---|---|
| Crossing | Tilt | Roll |
| 63.6 | −28.3 | −15.2 |

Identification of Peptide and TCR CDR Residues Critical for Binding

Figure 9:
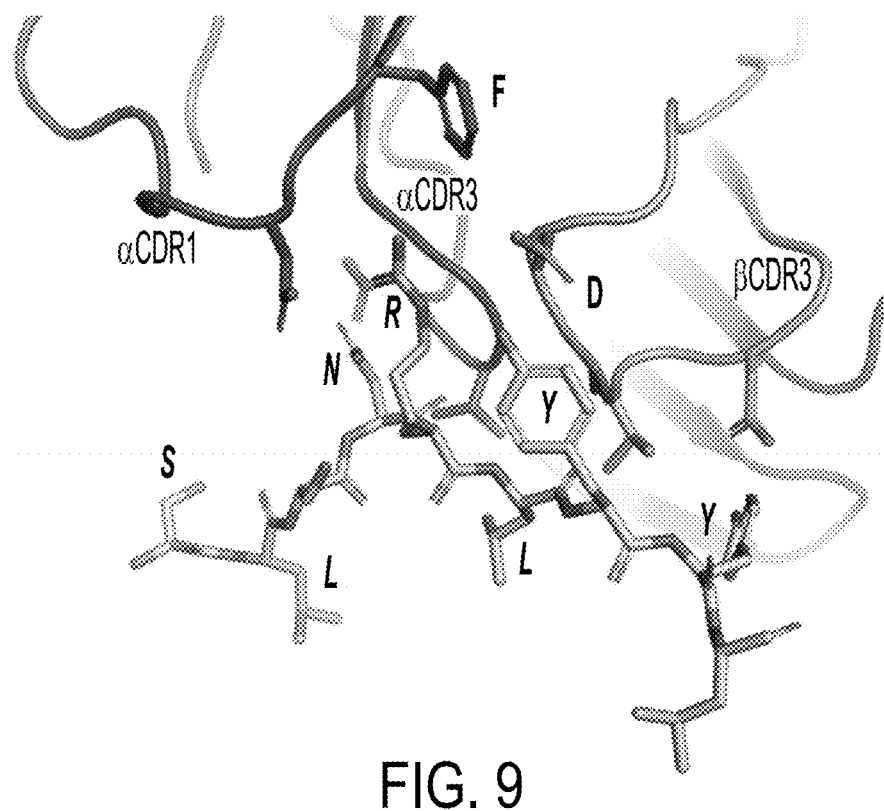
FIG. 9: image of the computationally modelled structure of TCR-peptide interface formed by the TCR variant a67b72 when bound to SLSNRLYYL (SEQ ID NO: 1) in complex with HLA-A*02. Key residue changes introduced during affinity maturation are labelled.

The crystal structure of the S8 TCR bound to SLSNR-LYYL (SEQ ID NO: 1) in complex with HLA-A*02 was further analyzed to identify critical residues within the interface between the peptide and the TCR CDRs. As can be seen in the crystal structure represented in FIG. 8, peptide side chains at positions N4, R5, Y7 and Y8 of SLSNRLYYL (SEQ ID NO: 1) formed the key antigenic contact points on the peptide, with the residues at these positions having exposed side chains facing the TCR interface. For the high affinity variants, described in the Examples above, the introduction of an S to D mutation in the CDR3β and a F to γ mutation in CDR1a together contributed to enhanced shape complementarity between the peptide and CDRs. In addition, the S to D mutation in the CDR3β improved specificity by increasing the window to mimetic peptide DOCK11. For example, the TCR variant referred to herein as "a67b72" includes both of these mutations and has an affinity for pHLA complex in the pM range and a wide affinity window to the mimetic peptide. The interface between the a67b72 and the SLSNRLYYL (SEQ ID NO: 1) peptide was computationally modelled based on the TCR crystal structure of S11 and is shown in FIG. 9.

The CDR residues of S8 TCR critical for binding to the SLSNRLYYL (SEQ ID NO: 1) peptide were also determined from the crystal structure based on proximity between the residues. The following table indicates these residues in bold and double underlined text:

| CDR1α | CDR2α | CDR3α | CDR1β | CDR2β | CDR3β |
|---|---|---|---|---|---|
| NIATND<u>Y</u> (SEQ ID NO: 5) | GYKTN (SEQ ID NO: 24) | LAWGGTDKLI (SEQ ID NO: 7) | SGHGT (SEQ ID NO: 37) | FQNNGV (SEQ ID NO: 16) | ASSLD<u>WVGS</u>GETQY (SEQ ID NO: 17) |

To demonstrate that high affinity TCR variants as described in Examples 1-6 maintain the same or similar peptide contacts as the S8 TCR, the peptide-contacting CDR residues of the TCR variant a67b72 SLSNRLYYL (SEQ ID NO: 1) were determined by computational modelling, using the crystal structure of the S8 TCR bound to SLSNRLYYL (SEQ ID NO: 1) in complex with HLA-A*02 as a template. The CDR positions of a67b72 that were critical for binding to SLSNRLYYL (SEQ ID NO: 1) were the same as for S8 and are shown in the table below.

| CDR1α | CDR2α | CDR3α | CDR1β | CDR2β | CDR3β |
|---|---|---|---|---|---|
| YIAAND<u>F</u> (SEQ ID NO: 23) | GYKTN (SEQ ID NO: 24) | LAWGGTDLLP (SEQ ID NO: 29) | SGHGT (SEQ ID NO: 37) | FHEEGV (SEQ ID NO: 45) | ASSVD<u>WVGD</u>GERQY (SEQ ID NO: 41) |

Comparison of S8 TCR Structure with TCRs Derived from Alternative Scaffolds

Figure 10:
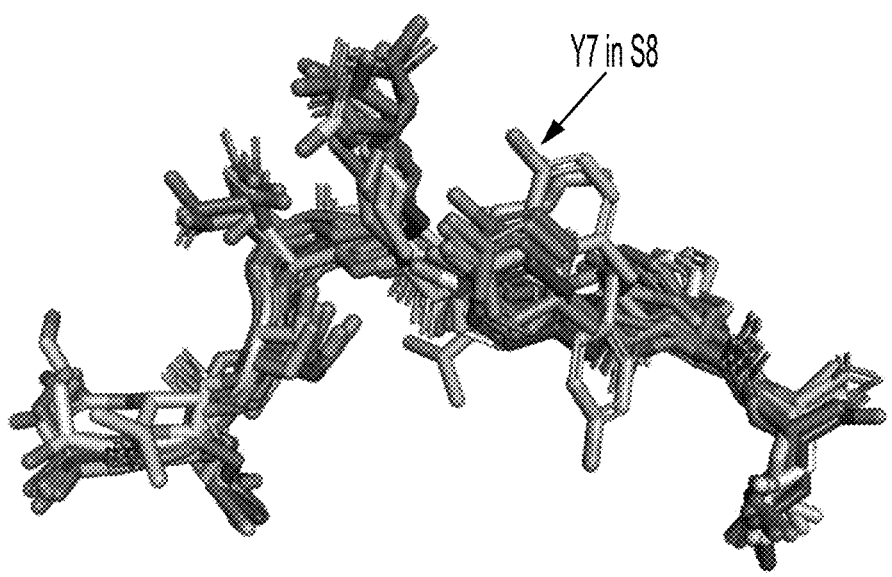
FIG. 10: overlay of x-ray crystal structures showing conformation of SLSNRLYYL (SEQ ID NO: 1) peptide when bound to different scaffold TCRs. The position of peptide residue Y7 when bound to S8 TCR is indicated.

Additional crystal structures were obtained for TCRs that bind to the same pHLA complex but were derived from different scaffold TCRs. Of the 10 TCRs analysed, only S8 TCR (and its high affinity variants described above) demonstrated hydrogen bond contacts to all the four exposed peptide residues and was the only TCR to show hydrogen bond contact to position Y7. With some alternative TCRs, the peptide Y7 side chain adopted a partially buried conformation and therefore was unable to make contacts with the TCR. An overlay of peptide conformations when bound to each TCR shows that for S8 TCR the peptide position Y7 was pulled upwards towards to make contact (FIG. 10).

These data provide the key antigenic features of the peptide and suggest that engaging Y7 directly contributes to both affinity and specificity of the interaction.

The invention claimed is:

1. A binding molecule comprising a TCR alpha chain variable a domain and a TCR beta chain variable domain, wherein the binding molecule has the property of binding to SLSNRLYYL (SEQ ID NO: 1) in complex with HLA-A*02, wherein each of the alpha chain variable domain and the beta chain variable domain comprises FR1-CDR1-FR2-CDR2-FR3-CDR3-FR4, where FR is a framework region and CDR is a complementarity determining region, comprising the following combination of alpha chain CDRs and beta chain CDRs:

| Alpha | | | Beta | | |
|---|---|---|---|---|---|
| CDR1 | CDR2 | CDR3 | CDR1 | CDR2 | CDR3 |
| YIAANDF (SEQ ID NO: 23) | GYKTN (SEQ ID NO: 24) | LAWGGT DLLP (SEQ ID NO: 29) | SGHGT (SEQ ID NO: 37) | FHEEGV (SEQ ID NO: 45) | ASSVDWV GDGERQY (SEQ ID NO: 41). |

2. The binding molecule of claim 1, wherein the alpha chain variable domain framework regions comprise the following sequences:
FR1—LAKTTQPISMDSYEGQEVNITCSHN (SEQ ID NO: 8), or SEQ ID NO: 8 with one, two or three mutations therein,
FR2—ITWYQQFPSQGPRFIIQ (SEQ ID NO: 9), or SEQ ID NO: 9 with one, two or three mutations therein,
FR3—VTNEVASLFIPADRKSSTLSLPRVSLSDTAVYYC (SEQ ID NO: 10), or SEQ ID NO: 10 with one, two or three mutations therein,
FR4—FGTGTRLQVFP (SEQ ID NO: 11), or SEQ ID NO: 11 with one, two or three mutations therein,
and/or
the beta chain variable domain framework regions comprise the following sequences:
FR1—EAGVAQSPRYKIIEKRQSVAFWCNPI (SEQ ID NO: 18), or SEQ ID NO: 18 with one, two or three mutations therein,
FR2—LYWYQQILGQGPKLLIQ (SEQ ID NO: 19), or SEQ ID NO: 19 with one, two or three mutations therein,
FR3—VDDSQLPKDRFSAERLKGVDSTLKIQPAKLEDSAVYLC (SEQ ID NO: 20), or SEQ ID NO: 20 with one, two or three mutations therein,
FR4—FGPGTRLLVL (SEQ ID NO: 21), or SEQ ID NO: 21 with one, two or three mutations therein.

3. The binding molecule of claim 2, wherein the alpha chain variable domain framework region comprises one or more of the following mutations:

| L1 | A |
|---|---|
| T21 | P |
| I47 | F |
| T56 | Q |
| P65 | S | numbered according to SEQ ID NO: 3.

4. The binding molecule of claim 3, wherein the alpha chain variable domain framework region comprises one of the following combinations of mutations:
(a) I47F, T56Q
(b) L1A, I47F, T56Q
(c) T21P, I47F, T56Q, P65S
(d) L1A, T21P, I47F, T56Q, P65S
numbered according to SEQ ID NO: 3.

5. The binding molecule of claim 2, wherein the beta chain variable domain framework region comprises the following mutation:

| R16 | G |
|---|---| numbered according to SEQ ID NO: 13.

6. The binding molecule of claim 1, wherein the alpha chain variable domain comprises the amino acid sequence of SEQ ID NO: 34 and the beta chain variable domain comprises the amino acid sequence of SEQ ID NO: 48.

7. The binding molecule of claim 1, comprises at least part of a TCR alpha chain constant domain and/or at least part of a TCR beta chain constant domain.

8. The binding molecule of claim 1, is an alpha-beta heterodimer, having an alpha chain TRAC constant domain sequence and a beta chain TRBC1 or TRBC2 constant domain sequence.

9. The binding molecule of claim 8, wherein a non-native covalent disulphide bond links a residue of the constant domain of the alpha chain to a residue of the constant domain of the beta chain.

10. The binding molecule of claim 1, is in single chain format of the type V Vα-L-Vβ, Vβ-L-Vα, Vα-Cα-L-Vβ, or Vα-L-Vβ-Cβ, wherein Vα and Vβ are TCR α and β variable domains respectively, Cα and Cβ are TCR α and β constant domains respectively, and L is a linker sequence.

11. The binding molecule of claim 1, comprises or consists of a TCR comprising the alpha chain variable domain and the beta chain variable domain.

12. The binding molecule of claim 1, further comprising an immunoglobulin heavy chain variable domain (VH) and an immunoglobulin light chain variable domain (VL), which associate to form an antigen binding moiety site that is capable of binding to an antigen.

13. The binding molecule of claim 12, wherein the antigen is a T cell surface antigen.

14. The binding molecule of claim 12, wherein the antigen is CD3.

15. The binding molecule of claim 12, wherein
(a) the VH comprises CDRs having the following sequences:

```
CDR1 -
                        (SEQ ID NO: 66)
GYSFTGYT
or
                        (SEQ ID NO: 71)
GYSFTGYA;

CDR2 -
                        (SEQ ID NO: 67)
INPYKGVS;
and

CDR3 -
                        (SEQ ID NO: 68
ARSGYYGDSDWYFDV,
``` and
(b) the VL comprises CDRs having the following sequences:

```
CDR1 -
                        (SEQ ID NO: 62)
QDIRNY;

CDR2 -
YTS;
and

CDR3 -
                        (SEQ ID NO: 64)
QQGNTLPWT.
```

16. The binding molecule of claim 15, wherein
the VH comprises an amino acid sequence as set forth in SEQ ID NO: 65 or 69, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in SEQ ID NO: 65 or 69; and
the VL comprises an amino acid sequence as set forth in SEQ ID NO: 61, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in SEQ ID NO: 61.

17. The binding molecule of claim 12, wherein the VH or VL is covalently linked to the C- or N-terminus of the alpha or beta chain of the TCR, or wherein the VH or VL is covalently linked to the C- or N-terminus of the alpha or beta chain of the TCR via a linker sequence, or wherein the VH or VL is covalently linked to the C- or N-terminus of the alpha or beta chain of the TCR via a linker sequence wherein the linker sequence is selected from SEQ ID NOs: 72 and 78-89.

18. The binding molecule of claim 1, comprising an alpha chain amino acid sequence corresponding to SEQ ID NO: 58 and a beta chain-anti-CD3 amino acid sequence corresponding to SEQ ID NO: 77.

19. The binding molecule of claim 12, comprising:
a first polypeptide chain which comprises the alpha chain variable domain and a first binding domain of a variable region of an antibody; and
a second polypeptide chain which comprises the beta chain variable domain and a second binding domain of a variable region of said antibody,
wherein the respective polypeptide chains associate such that the specific binding molecule is capable of simultaneously binding SLSNRLYYL (SEQ ID NO: 1) in complex with HLA-A*02 and an antigen of the antibody.

20. The binding molecule of claim 1 associated with an Fc domain.

21. A pharmaceutical composition comprising the binding molecule of claim 1, together with one or more pharmaceutically acceptable carriers or excipients.

22. A method of treating cancer comprising administering the binding molecule of claim 1 or a pharmaceutical composition thereof.

* * * * *

UNITED STATES PATENT AND TRADEMARK OFFICE
CERTIFICATE OF CORRECTION

PATENT NO. : 12,195,534 B2
APPLICATION NO. : 18/405977
DATED : January 14, 2025
INVENTOR(S) : Nicole Mai et al.

Page 1 of 1

It is certified that error appears in the above-identified patent and that said Letters Patent is hereby corrected as shown below:

In the Claims

Column 111 Line 56 Claim 2:
Replace "SEQ ID NO:9with" with --SEQ ID NO:9 with--

Column 113 Line 3 Claim 7:
Replace "The binding molecule of claim 1, comprises" with --The binding molecule of claim 1, which comprises--

Column 113 Line 6 Claim 8:
Replace "The binding molecule of claim 1, is an alpha-beta" with --The binding molecule of claim 1, which is an alpha-beta--

Column 113 Line 16 Claim 10:
Replace "The binding molecule of claim 1, is in single chain" with --The binding molecule of claim 1, which is in single chain--

Column 113 Line 23 Claim 11:
Replace "The binding molecule of claim 1, comprises or consists of" with --The binding molecule of claim 1, which comprises or consists of--

Signed and Sealed this
Twenty-fifth Day of March, 2025

Coke Morgan Stewart
*Acting Director of the United States Patent and Trademark Office*